United States Patent [19]

Paoletti et al.

[11] Patent Number: 5,766,598
[45] Date of Patent: Jun. 16, 1998

[54] RECOMBINANT ATTENUATED ALVAC CANARYPOXVIRUS EXPRESSION VECTORS CONTAINING HETEROLOGOUS DNA SEGMENTS ENCODING LENTIVIRAL GENE PRODUCTS

[75] Inventors: Enzo Paoletti, Delmar; James Tartaglia, Schenectady; William Irvin Cox, Troy, all of N.Y.

[73] Assignee: Virogenetics Corporation, Troy, N.Y.

[21] Appl. No.: 303,275

[22] Filed: Sep. 7, 1994

Related U.S. Application Data

[63] Continuation of Ser. No. 897,382, Jun. 11, 1992, abandoned, which is a continuation-in-part of Ser. No. 715,921, Jun. 14, 1991, abandoned, and Ser. No. 847,951, Mar. 6, 1992, which is a continuation-in-part of Ser. No. 713,967, Jun. 11, 1991, which is a continuation-in-part of Ser. No. 666,056, Mar. 7, 1991.

[51] Int. Cl.$^6$ .................. A61K 39/12; A61K 39/295; A61K 39/21; A61K 39/275
[52] U.S. Cl. ............. 424/199.1; 424/208.1; 424/232.1; 424/201.1; 435/320.1; 435/236; 435/172.3
[58] Field of Search ............. 435/69.1, 172.3, 435/235, 236, 237; 424/199.1, 202.1, 208.1, 209.1

[56] References Cited

U.S. PATENT DOCUMENTS

| 5,093,258 | 3/1992 | Cohen | 435/235.1 |
| 5,174,993 | 12/1992 | Paoletti | 424/89 |
| 5,180,675 | 1/1993 | Prillien | 435/235.1 |
| 5,185,146 | 2/1993 | Attenburger | 424/89 |

FOREIGN PATENT DOCUMENTS

| WO 89/03429 WO A | of 1989 | WIPO . |
| 89/03429 WO A | 4/1989 | WIPO . |
| 90/10693 WO A | 9/1990 | WIPO . |
| 90/12101 | 10/1990 | WIPO . |

OTHER PUBLICATIONS

Turner, P.C. et al. (90) Current topics in Microbiol. Immunol. 163: 125–151.
Lerner, R.A. et al. (83) in: The Biology of Immunologic Disease, eds. F.J. Dixon & D.W. Fisher, H.P. Publishing Co. New York, NY, pp. 331–338.
Wain–Hobson, S. et al. (85) Cell 40:9–17.
Cooney, E.L. et al. (91) Lancet 337:567–572.
Tartaglia, J. et al. (906) in: Immunochemistry of Viruses, eds. M.H.V. van Regenwortel and A.R. Newrath, Elsevier Science Publishers B.V. pp. 125–151.
Norley, S. et al. Immunobiology 184: 193–207 (1992).
Cohen, J. et al. Science 262: 980–81 (1993).
Moss, B., 1996, "Poxviridae: The Viruses and Their Replication"in Fields Virology, Third Edition, Fields et al., eds., Lippincott–Raven Publishers, Philadelphia, pp. 2637–2671.

Murphy, F., 1996, "Virus Taxonomy", in Fields Virology, Third Edition, Fields et al., eds., Lippincott–Raven Publishers, Philadelphia, pp. 15–57.
Taylor et al., 1991, Vaccine 9(3):190–193.
Berman et al., 1990, Nature 345:622–625.
Girard et al., 1991, Proc. Natl. Acad. Sci. USA 88:542–546.
Hu et al., 1986, Nature 320:537–540.
Ho et al., 1990, Eur. J. Immunol. 20:477–483.
Virology, vol. 173, No. 1, issued Nov. 1989, S. Dallo et al., "Humoral Immune Response Elicited by Highly Attenuated Variants of Vaccinia Virus and by an Attenuated Recombinant Expressing HIV-1 Envelope Protein", pp. 323–328 (entire document).
Virology, vol. 152, issued 1986, M.E. Perkus et al., "Insertion and Deletion Mutants of Vaccinia Virus", pp. 285–297 (entire document).
Nature, vol. 317, issued 31 Oct. 1985, R.M.L. Buller et al., "Decreased Virulence of Recombinant Vaccinia Virus Expression Vectors is Associated With a Thymidine Kinase–Negative Phenotype", pp. 813–815 (entire document).
Journal of Virology, vol. 62, No. 12, issued Dec. 1988, H. Shida et al., "Effects and Virulences of Recombinant Vaccinia Viruses Derived From Attenuated Strains That Express the Human T–Cell Leukemia Virus Type 1 Envelope Gene", pp. 4474–4480 (entire document).
Critical Reviews in Immunology, vol. 10, No. 1, issued 1990, J. Tartaglia et al., "Poxvirus–Based Vectors as Vaccine Candidates", pp. 13–30 (entire document). (Tartaglia 900).
Virology, vol. 188, No. 1, issued May 1992, J. Tartaglia et al., "NYVAC: A Highly Attenuated Strain of Vaccinia Virus", pp. 217–232 (entire document).
Hosmalin, A., Nara, P.L., Zweig, M., Lerche, N.W., Cease, K.B., Gard, E.A., Markham, P.D., Putney, S.D., Daniel, M.D., Desrosiers, R.C., and Berzofsky, J.A., J. Immunol. 146, 1667–1673 (1991).

(List continued on next page.)

Primary Examiner—Laurie Scheiner
Assistant Examiner—Jeffrey S. Parkin
Attorney, Agent, or Firm—Frommer Lawrence & Haug LLP; William S. Frommer; Thomas J. Kowalski

[57] ABSTRACT

This invention is directed toward recombinant attenuated canarypox virus expression vectors containing exogenous DNA segments encoding lentiviral gene products. A parental canarypox virus (Rentschler strain) was obtained and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination studies. This attenuated plaque purified canarypox isolate was designated ALVAC. A series of ALVAC recombinants were generated that are capable of expressing different HIV and SIV gene products including Gag, Pol, Env, and Nef. These recombinants provide useful reagents for the generation of viral-specific immune responses.

14 Claims, 9 Drawing Sheets

OTHER PUBLICATIONS

Letvin, N.L., and King, N.W., J. AIDS 3, 1023–1040 (1990).

McMichael, A.J., Gotch, F.M., Noble, G.R., and Beare, P.A.S., New Engl. J. Med. 309, 13–17 (1983).

Moss, D.J., Rickinson, A.B., and Pope, J.H., Int. J. Cancer 22, 662–668 (1978).

Schmaljohn et al., Virology 155, 633–643 (1986).

Schmitt et al., J. Virol. 62, 1889–1897 (1988).

Tartaglia, J., Winslow, J., Goebel, S., Johnson, G.P., Taylor, J., and Paoletti, E., J. Gen. Virol. 71, 1517–1524 (1990).

Tartaglia et al., Virology 188, 217–232 (1992).

Taylor et al., Virology 187, 321–328 (1992).

Vos et al., EMBO J. 7, 3487–3492 (1988).

Walker, B.D. and Plata, F., AIDS 4, 177–184 (1990).

Walker, B.D., Chakrabarti, S., Moss, B., Paradi, T.J., Flynn, T., Durno, A.G., Blumberg, R.S., Kaplan, J.C., Hirsch, M.S., and Schooley, R.T., Nature 328, 345–348 (1987).

Walker, B.D., Flexner, C., Birch–Limberger, K., Fisher, L., Paradis, T.J., Aldovini, A., Young, R., Moss, B., and Schooley, R.T., Proc. Natl. Acad. Sci. 86, 9514–9519 (1989).

Weiss, R.A., Clapham, P.R., Cheingsong–Popov, R., Dalgleish, G., Carne, C.A., Weller, I.V., and Tedder, R.S., Nature 316, 69–72 (1985).

Yuen, L., and Moss, B., Proc. Natl. Acad. Sci. USA 84, 6417–6421 (1987).

Zagury, D., Bernard, J., Cheynier, R., Desportes, I., Leonard, R., Fouchard, I., Reveil, B., Ittele, D., Lurhuma, Z., Mbayo, K., Wane, J., Salaun, J.–J., Goussard, B., Dechazal, L., Burny, A., Nara, P. and Gallo, R.C., Nature 332, 728–731 (1988).

Zarling, J.M., Morton, W., Moran, P.A., McClure, J., Kosowski, S.G., and Hu, S.–L., Nature 323, 344–346 (1986).

Autran, B., Plata, F., and Debre, P., J. AIDS 4, 361–367 (1991).

Borysiewicz, L., Graham, S., Hickling, J., Mason, P.D., and Sissons, J.P.G., Eur. J. Immunology 18, 269–275 (1988).

Good, M.F., Maloy, W.L., Lunde, M.N., Margalit, H., Cornette, J.L., Smith, G.L., Moss, B., Miller, L.H., and Berzofsky, J.A., Science 235, 1059–1062 (1987).

Guo, P., Goebel, S., Davis, S., Perkus, M.E., Taylor, J., Norton, E., Allen, G., Lanquet, B., Desmettre, P., and Paoletti, E., J. virol. 174, 217–214 (1990).

Ho, P.C., Mutch, D.A., Winkel, K.D., Saul, A.J., Jones, G.L., Doran, T.J., and Rzepczyk, C.M., Eur. J. Immunol. 20, 477–483 (1990).

Ruegg, C.L., Monell, C.R., and Strand, M., J. Virol. 63, 3257–3260 (1989b).

Sanchez–Pascador, R., Power, M.D., Barr, P.J., Steimer, K.S., Stampien, M.M., Brown–Shimer, S.L., Gee, W., Renard, A., RAndolph, A., Levy, J.A., Dina, D., and Luciw, P.A., Science 227, 484–492 (1985).

Sanger, F., Nickeln, S., and Coulson, A. R., Proc. Natl. Acad. Sci. 74, 5463–5467 (1977).

Shaffermann, A., Lennox, J., Grosfeld, H., Sadoff, J., Redfield, R.R., and Burke, D.S., AIDS Research and Human Retroviruses 5, 33–39 (1989).

Shapira, S.K., Chou, J., Richaud, F.V., and Casadaban, M.J., Gene 25, 71–82 (1983).

Shioda, T. and H. Shibuta, Virology 175, 139–148 (1990).

Starcich et al., Cell 45, 637–648 (1986).

Tabor, S., and Richardson, C.C., Proc. Natl. Acad. Sci. USA 84, 4767–4771 (1987).

Tartaglia, J. and Paoletti, E., In Immunochemistry of viruses, II, eds. van Regenmortel, M.H.V and Neurath, A.R., (Elsevier Science Publishers B.V., Amsterdam) pp. 125 (1990).

Taylor, J. et al., Vaccine 6, 466–467 (1988).

Taylor, J. et al., Vaccine 9, 190–193 (1991).

Taylor, J., Weinberg, R., Lanquet, B., Desmettre, P., and Paoletti, E., Vaccine 6, 497–503 (1988a).

Taylor, J., Weinberg, R., Kawaoka, Y., Webster, R.G., and Paoletti, E., Vaccine 6, 504–508 (1988b).

Walker, B.D., Flexner, C., Paradis, T.J., Fuller, T.C., Hirsch, M.S., Schooley, R.T. and Moss, B., Science 240, 64–66 (1988).

Nixon, D.F., Townsend, A.R.M., Elvin, J.G., Rizza, C.R., Gallwey, J., and McMichael, A.J., Nature 326, 484–487 (1988).

Panicali, D., and Paoletti, E., Proc. Natl. Acad. Sci. USA 79, 4927–4931 (1982).

Perkus, M.E., Piccini, A., Lipinskas, B.R., and Paoletti, E., Science 229, 981–984 (1985).

Perkus, M.E., Goebel, S.J., Davis, S.W., Johnson, G.P., Limbach, K., Norton, E.K., and Paoletti, E., Virology 179, 276–286 (1990).

Perkus, M.E., Limbach K., and Paoletti, E., J. Virol. 63, 3829–3836 (1989).

Piccini, A., Perkus, M.E., and Paoletti, E., Methods in Enzymology 153, 545–563 (1987).

Plata, F., Autran, B., Martins, L.P., Wain–Hobson, S., Raphael, M., Mayaud, C., Denis, M., Guillon, J.–M., Debre, P., Nature 328, 348–351 (1987).

Ratner, L., Hasseltine, W., Patarca, R., Livak, K.J., Starcich, B., Josephs, S.F., Doran, E.R., Rafalski, J.A., Whitehorn, E.A., Baumeister, K., Ivanoff, L., Petteway, Jr., S.R., Pearson, M.L., Lautenberger, J.A., Papas, T.S., Ghrayeb, J., Chang, N.T., Gallo., R.C., and Wong–Staal F., Nature 313, 277–284 (1985).

Rautmann, G., Kieny, M.–P., Brandely, R., Dott, K., Girard, M. Montagnier, L., and Lecocg, J.–P. AIDS Research and Human Retroviruses 5, 147–157 (1989).

Riviere Y., Tanneau–Salvadori, F., Regnault, A., Lopez, O., Sansonetti, P., Guy, B., Kieny, M.–P., Fournel, J.–J., and Montagnier, L., J. Virol. 63, 2270–2277 (1989).

Rodriguez, D. et al., Proc. Natl. Acad. Sci. USA 86, 1287–1291 (1989).

Ruegg, C.L., Monell, C.R., and Strand, M., J. Virol. 63, 3250–3256 (1989a).

Karacostas, V., Nagashima, K., Gonda, M.A., and Moss, B., Proc. Natl. Acad. Sci. USA 86, 8964–8968 (1989).

Klasse, P.J., Pipkorn, R., and Blomberg, J., Proc. Natl. Acad. Sci. USA 85, 5225–5229 (1988).

Kodama, T., Wooley, D.P., Naidu, Y.M., Kestler III, H.W., Daniel, M.D., Li, Y., and Derisiers, R.C., J. Virol. 63, 4709–4714 (1989).

Koff, W.C. and Fauci, A.S., AIDS 1, S125–S129 (1989).

Koup, R.A., Sullivan, J.L., Levine, P.H., Brettler, D., Mahr, A., Mazzara, G., McKenzie, S., and Panicali, D., Blood 73, 1909–1914 (1989).

Kunkel, T.A., Proc. Natl. Acad. Sci. USA 82, 488–492 (1985).

Laemmli, U.K., Nature (London) 227, 680–685 (1970).

Lane, J.M., Ruben, F.L., Neff, J.M., and Millar, J.D., New Eng. J. Med. 281 1201–1208 (1969).

LaRosa, G.J., Davide, J.P., Weinhold, K., Waterbury, J.A., Profy, A.T., Lewis, J.A., Langlois, A.J., Dressman, G.R., Boswell, R.N., Shadduck, P., Holley, L.H., Karpus, M., Bolognesi, D.P., Matthews, T.J., Emini, E.A., and Putney, S.D., Science 249, 932–935 (1990).

Mandecki, W., Proc. Natl. Acad. Sci. USA 83, 7177–7182 (1986).

Maniatis, T., Fritsch, E.F., and Sambrook, J. In Molecular cloning: a laboratory manual, (Cold Spring Harbor Laboratory, Cold Spring Harbor, NY) (1982).

Michel, F., Hoffenbach, A., Langlade–Demoyen, P., Guy, B., Lecocq, J.–P., Wain–Hobson, S., Kieny, M.–P. and Plata, F., Eur. J. Immunology 18, 1917–1927 (1988).

Murphy–Corb, M., Martin, L.N., Davison–Fairburn, B., Montelaro, R.C., Miller, M., West, M., Ohkawa, S., Baskin, G.B., Zhang, J.–Y., Putney, S.D., Allison, A.C. and Eppstein, D.A., Science 246, 1293–1297 (1989).

Franchini, G., Fargnoli, K.A., Giomnini, F., Jagodzinski, L., DeRossi, A., Bosch, M., Biberfield, G., Fenyo, E.M., Albert, J., Gallo, R.C., and Wong–Staal, F., Proc. Natl. Acad. Sci. USA 86, 2433–2437 (1989).

Gillard, S., Spehner, D., Drillien, R., and Kirn, A., Proc. Natl. Acad. Sci. USA 83, 5573–5577 (1986).

Goebel, S.J., Johnson, G.P., Perkus, M.E., Davis, S.W., Winslow, J.P., and Paoletti, E., Virology 179, 247–266 (1990a).

Goebel, S.J., Johnson, G.P., Perkus, M.E., Davis, S.W., Winslow, J.P., and Paoletti, E., Virology 179, 517–563 (1990b).

Guo, P., Goebel, S., Davis, S., Perkus, M.E., Taylor, M., Norton, E., Allen, G., Lanquet, B., Desmettre, P., and E. Paoletti, J. Virol. 64, 2399–2406 (1990).

Guo, P., Goebel, S., Davis, S., Perkus, M.E., Lanquet, B., Desmettre, P., Allen, G., and Paoletti, E., J. Virol. 63, 4189–4198 (1989).

Haffar, O., Garrigues, J., Travis, B., Moran, P., Zarling, J., and Hu, S.–L., J. Virol. 64, 2653–2659 (1990).

Hu, S.–L., Fultz, P., McClure, H., Eichberg, J., Thomas, E., Zarling, J., Singhal, M., Kosowski, S., Swenson, R., Anderson, D., and Todaro, G., Nature 328, 721–723 (1987).

Hu, S.–L. Travis, B.M., Garrigues, J., Zarling, J.M., Eichberg, J.W. and Alpers, C.E., In Vaccine 90, eds. Chanock, R.M., Lerner, R.A., Brown, F., and Ginsberg, H., (Cold Spring Harbor Press, Cold Spring Harbor, New York) pp. 231–236 (1990).

Hu, S.–L., Kosowski, S., and Dalrymple, J., Nature 320, 537–540, (1986).

Hu, S.L., Zarling, J.M., Chinn, J., Travis, B.M., Moran, P.A., Sias, J., Kuller, L., Morton, W.R., Heidecker, G., and Benveniste, R.E., Proc. Natl. Acad. Sci. USA 86, 7213–7217 (1989).

Javeherian, K., Langlois, A.J., McDanal, C., Ross, K.L., Eckler, L.I., Jellib, C.L., Profy, A.T., Rusche, J.R., Bolognesi, D.P., Putney, S.D., and Matthews, T.J., Proc. Natl. Acad. Sci. USA 86, 6768–6772 (1989).

Behbehani, A.M., Microbiological Reveiws 47, 455–509 (1983).

Bertholet, C., Drillien, R. and Wittek, R., Proc. Natl. Acad. Sci. 82, 2096–2100 (1985).

Chakrabarti, S., Robert–Guroff, M., Wong–Staal, F., Gallo, R.C., and Moss, B., Nature 320, 535–537 (1986).

Cianciolo, G.J., Copeland T.D., Oroszlan S., and Snyderman, R., Science 230, 453–456 (1985).

Clewell, D.B., and Helinski, D.R., Proc. Natl. Acad. Sci. USA 62, 1159–1166 (1969).

Clewell, D.B., J. Bacteriol 110, 667–676 (1972).

Colinas, R.J., Condit, R.C., and Paoletti, E., Virus Research 18, 49–70 (1990).

Desrosiers, R.C., M.S., Wyand, T., Kodama, T.J. Ringler, L.O. Arthur, P.K. Seghal, N.L. Letvin, N.W. King, and M.D. Daniel, Proc. Natl. Acad. Sci. USA 86, 6353–6357 (1989).

Dreyfuss, G., Adam, S.A., and Choi, Y.–D., Mol. Cell. Biol. 4, 415–423 (1984).

Engelke, D.R., Hoener, P.A., and Collins, F.S., Proc. Natl. Acad. Sci. USA 85, 544–548 (1988).

Franchini, G., Gurgo, C., Guo, H.–G., Gallo, R.C., Collati, E., Fargnoli, K.A., Hall, L.F., Wong–Staal, F., and Reitz, Jr., M.S., Nature (London) 328, 539–543 (1987).

5,766,598

1

RECOMBINANT ATTENUATED ALVAC CANARYPOXVIRUS EXPRESSION VECTORS CONTAINING HETEROLOGOUS DNA SEGMENTS ENCODING LENTIVIRAL GENE PRODUCTS

CROSS-REFERENCE TO RELATED APPLICATIONS

This application is a continuation of application Ser. No. 07/897,382, filed Jun. 11, 1992 now abandoned, which in turn is a continuation-in-part of application Ser. No. 07/715,921, filed Jun. 14, 1991, now abandoned. Application Ser. No. 07/897,382 is also a continuation-in-part of copending application Ser. No. 07/847,951, filed Mar. 6, 1992, also incorporated herein by reference application Ser. No. 07/847,951 is a continuation-in-part of application Ser. No. 07/713,967, filed Jun. 11, 1991, which in turn is a continuation-in-part of application Ser. No. 07/666,056, filed Mar. 7, 1991.

FIELD OF THE INVENTION

The present invention relates to a modified poxvirus and to methods of making and using the same. More in particular, the invention relates to recombinant poxvirus, which virus expresses gene products of an immunodeficiency virus gene, and to immunogenic compositions which induce an immunological response against immunodeficiency virus infections when administered to a host.

Several publications are referenced in this application. Full citation to these references is found at the end of the specification preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. Nos. 5,110,587, 4,769,330, 4,722,848 and 4,603,112, the disclosures of which are incorporated herein by reference. In this regard, reference is also made to copending U.S. applications Ser. Nos. 881,995 filed May 4, 1992 and 537,890, filed Jun. 14, 1990, also incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1986).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

In recent years much attention within the field of medical virology has been focused on the escalating incidence of acquired immunodeficiency syndrome (AIDS) caused by human immunodeficiency virus (HIV). HIV-1 is a member of the virus family, Retroviridae, and more specifically of the Lentivirus subfamily. This viral system along with other related viruses such as HIV-2 and simian immunodeficiency virus (SIV) have been scrutinized with respect to their molecular biology, immunology, and pathogenesis in an effort to develop safe and efficacious vaccines and antiviral therapies. Two major obstacles, however, have haunted the design of HIV vaccine candidates. For one, there exists considerable sequence heterogeneity among HIV isolates, and secondly, there exists a lack of information pertaining to protective immunity. Infected individuals develop antibody (Starcich et al., 1986; Weiss et al., 1985) and CD8$^+$-T cell (Walker et al., 1987; Plata et al., 1987) responses to HIV but are not protected since they eventually develop AIDS.

Vaccinia virus has been used extensively to express a number of HIV gene products to investigate their biochemical, functional and immunological properties, particularly cell-mediated responses. Using these specific reagents, cell-mediated cytotoxic activities have been demonstrated in seropositive individuals towards the envelope (Riviere et al., 1989; Walker et al., 1987; Koup et al., 1989), core proteins (gag) (Riviere et al., 1989; Koup et al., 1989, Nixon et al., 1988) pol (Walker et al., 1989; Walker et al., 1988), and the nef (Riviere et al., 1989) gene products. Additionally, vaccinia virus recombinants containing HIV genes have been shown to elicit both cell-mediated and humoral immune responses in small laboratory animals (Chakrabarti et al., 1986; Hu et al., 1986; Rautman et al., 1989; Michel et al., 1988), macaques (Zarling et al., 1986), chimpanzees (Hu et al., 1987) and, significantly, humans (Zagury et al., 1988; Koff et al., 1989). To date, limited vaccination/protection studies in primates have been reported with vaccinia virus recombinants expressing gene products from HIV and related viruses.

Vaccination of primates with a recombinant vaccinia virus expressing the envelope glycoprotein from AIDS-causing retroviruses have elicited humoral and cell-mediated immune responses and, more significantly, have protected against HIV infection (Zagury et al., 1988; Hu et al., 1989). In the results described by Hu et al., a vaccinia virus recombinant expressing the envelope glycoprotein from simian AIDS retrovirus (SRV-2) was used to vaccinate pig-tailed macaques (*Macaca nemestrina*). All immunized animals developed both SRV-specific cell-mediated and humoral immune responses, including neutralizing antibodies and antibodies which mediate ADCC towards SRV-2 infected cells. Animals were challenged intravenously with $5 \times 10^3$ TCID$_{50}$ of SRV-2/W. The challenged control animals (non-vaccinated) became viremic by two weeks post-challenge and those that did not seroconvert died by seven weeks post-challenge. Significantly, all of the challenged animals which were previously inoculated with the vaccinia virus-env recombinant remained healthy, virus-free and seropositive exclusively against the envelope antigen.

In a pilot experiment in humans, HIV seronegative individuals were vaccinated with a vaccinia virus/HIV-1 envelope recombinant. This primary inoculation resulted in weak immunological responses (Zagury et al., 1988). These primary responses were subsequently boosted with various protocols. The use of an intravenous injection of paraformaldehyde-fixed autologous cells infected in vitro with the vaccinia virus-HIV recombinant, however, provided the most significant booster effect. With this immunization protocol, anamnestic immune responses were achieved against the envelope antigen consisting of group-specific neutralizing antibodies, cytotoxic T-lymphocytes and delayed-type hypersensitivity (Zagury et al., 1988). In clinical trials performed in the United States using a recombinant vaccinia virus expressing the HIV env gene (HIVAV-le; Bristol-Meyers), individuals receiving the recombinant mounted T-cell proliferative responses to HIV (Koff et al., 1989). The intensity of these responses, however, was affected by prior exposure to vaccinia virus. Consequently, individuals immune to vaccinia virus mounted a weak and transient T-cell response whereas in individuals not immune to vaccinia virus, a strong response was observed towards the HIV envelope antigen (reviewed by Koff et al., 1989). These results are encouraging and have provided evidence that an immune state can be obtained in man prior to HIV exposure using a poxvirus-based immunization vehicle.

An intriguing potential in terms of HIV-1 vaccinology is provided by expression of the HIV-1 gag products by vaccinia virus either alone or in combination with the envelope glycoprotein. Several laboratories have demonstrated that expression of gag or gag/pol sequences by vaccinia virus results in the production of non-infectious particles (Hu et al., 1990; Shioda et al., 1990; Karacostas et al., 1989). Analysis of these vaccinia virus recombinant infected cells by electron microscopy revealed retrovirus-like particles budding from the plasma membrane and extracellular forms which were indistinguishable from particles observed in HIV-1 infected cells. Biochemically, these particles are also similar to native HIV-1 particles. Moreover, rodents and chimpanzees inoculated with a vaccinia virus-HIV gag recombinant generated both humoral and cell-mediated immune responses to the HIV-1 core antigens (Hu et al., 1990).

The co-expression of the HIV-1 envelope glycoprotein with the core proteins in mammalian cells by vaccinia virus also resulted in the assembly and release of HIV-1 particles (Haffar et al., 1990). These typical type C-retrovirus particles contained both the envelope glycoproteins (gp120 and gp41) and the gag proteins (p24, p17, p55, and p39). These proteins were also described as being present in these recombinant-made particles in the same ratio as observed in HIV-1 virions. The production of these non-infectious HIV particles either in purified form or synthesized in a vaccinee upon inoculation with a multivalent vaccinia virus recombinant may provide valuable "whole-virus" vaccinating agents against HIV. This is especially appealing since protection against the lentivirus, SIV, has been demonstrated using whole inactivated virus preparations (Murphy-Corb et al., 1989; Derosiers et al., 1989).

The above reviewed examples demonstrate the potential use of vaccinia virus recombinants expressing HIV antigens to induce pertinent immunological responses necessary for protection. A major concern, however, about the use of live viral vaccines is the issue of safety. Rare complications from immunization with vaccinia virus have been documented, particularly in immunocompromised individuals, and have raised some objections for their acceptance as vaccine candidates (Behbehani, 1983; Lane et al., 1969). Recently, however, significant strides have been made in understanding viral virulence factors with the hope of modifying strains for use as immunization vehicles (Tartaglia et al., 1990). With more relevance to the development of vaccinia virus-based HIV vaccine candidates for the immunoprophylaxis and immunotherapy of AIDS, the genes responsible for the productive replication of vaccinia virus in human cell systems have been identified (Gillard et al., 1986; Perkus et al., 1990). Potential use of vaccinia virus vectors devoid of these genes provide a non-replicating vector vaccine candidate that may present appropriate HIV antigens in a fashion that elicits a protective immune response.

Another approach towards the generation of safe and effective poxvirus based HIV vaccine candidates utilize avipoxvirus vectors (i.e. canarypoxvirus and fowlpoxvirus) to express pertinent HIV antigens. These viruses are naturally host-restricted and only productively replicate in avian species. Therefore, there exists a built-in safety factor for their use in humans, particularly immunocompromised individuals. In this regard, these viruses have been engineered to express the rabies G glycoprotein and have been demonstrated to protect various nonavian species from live rabies challenge (Taylor et al., 1988a; 1991).

It can thus be appreciated that provision of an immunodeficiency virus recombinant poxvirus, and of an immunogenic composition which induces an immunological response against immunodeficiency virus infections when administered to a host, particularly a composition having enhanced safety, would be a highly desirable advance over the current state of technology.

OBJECTS OF THE INVENTION

It is therefore an object of this invention to provide recombinant poxviruses, which viruses express gene products of an immunodeficiency virus, and to provide a method of making such recombinant poxviruses.

It is an additional object of this invention to provide for the cloning and expression of immunodeficiency virus coding sequences, particularly human immunodeficiency virus (HIV) and simian immunodeficiency virus (SIV) coding sequences in a poxvirus vector.

It is another object of this invention to provide an immunological composition having enhanced safety and which is capable of inducing an immunological response against immunodeficiency virus infections when administered to a host.

These and other objects and advantages of the present invention will become more readily apparent after consideration of the following.

STATEMENT OF THE INVENTION

In one aspect, the present invention relates to a recombinant poxvirus containing therein a DNA sequence from an immunodeficiency virus, particularly HIV or SIV, in a nonessential region of the poxvirus genome. The poxvirus is advantageously a vaccinia virus or an avipox virus, such as fowlpox virus or canarypox virus.

According to the present invention, the recombinant poxvirus expresses gene products of the foreign immunodeficiency virus gene, particularly an HIV or SIV gene.

In another aspect, the present invention relates to a vaccine for inducing an immunological response in a host animal inoculated with the vaccine, said vaccine including a carrier and a recombinant poxvirus containing, in a nonessential region thereof, DNA from an immunodeficiency virus, particularly HIV or SIV. The poxvirus used in the vaccine according to the present invention is advantageously a vaccinia virus or an avipox virus, such as fowlpox virus or canarypox virus.

BRIEF DESCRIPTION OF THE DRAWINGS

A better understanding of the present invention will be had by referring to the accompanying drawings, in which.

DETAILED DESCRIPTION OF THE INVENTION

Figure 1:
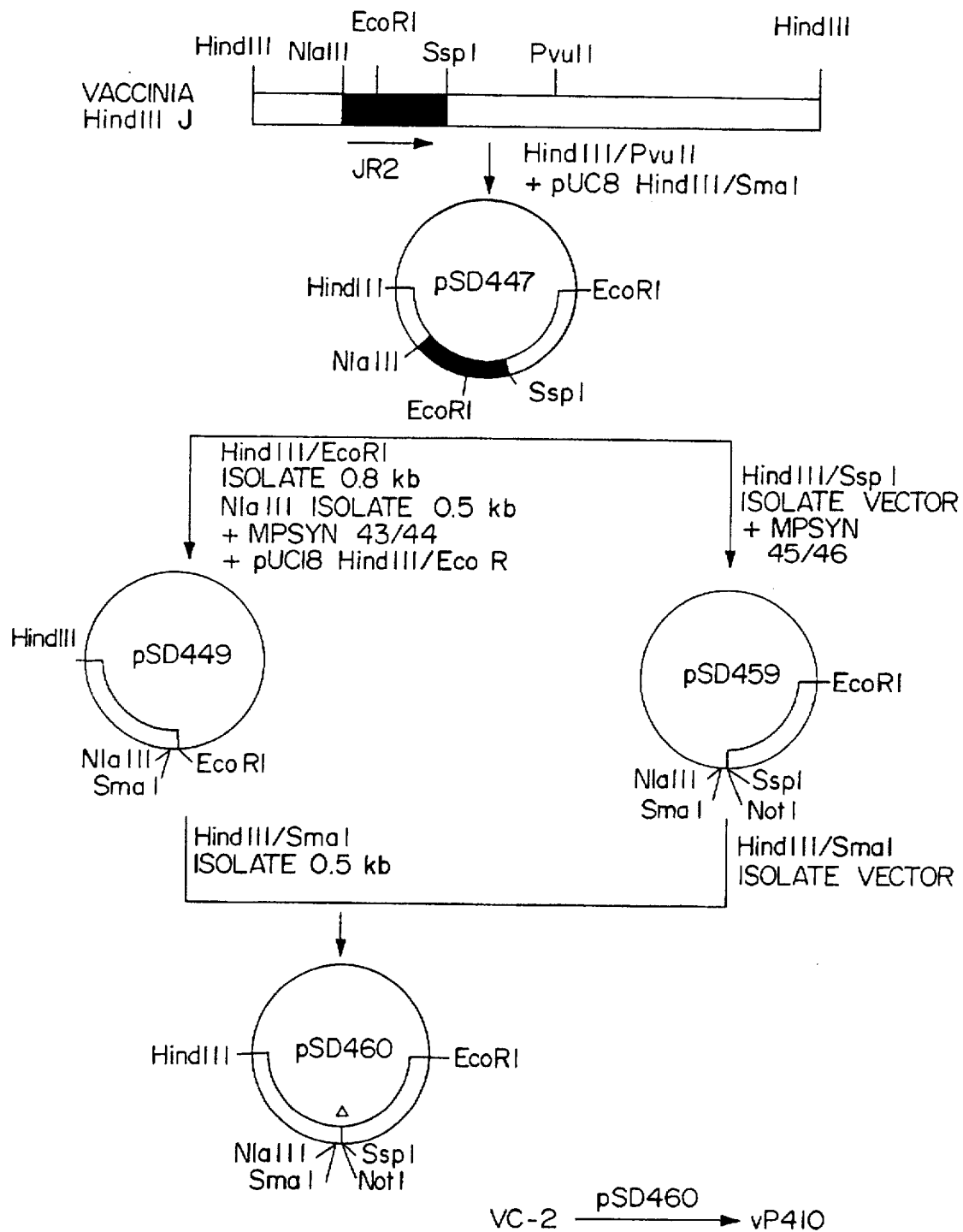
FIG. 1 schematically shows a method for the construction of plasmid pSD460 for deletion of thymidine kinase gene and generation of recombinant vaccinia virus vP410.

A better understanding of the present invention and of its many advantages will be had from the following examples, given by way of illustration.

In the Examples, the following methods and materials are employed.

DNA Cloning and Synthesis

Plasmids were constructed, screened and grown by standard procedures (Maniatis et al., 1982; Perkus et al., 1985; Piccini et al., 1987). Restriction endonucleases were obtained from GIBCO/BRL, Gaithersburg, Md.; New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection

The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC. ALVAC was deposited under the terms of the Budapest Treaty with the ATCC, accession number VR-2547.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scale from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b). P815 murine mastocytoma cells (H-$2^d$) were obtained from ATCC (#TIB64) and maintained in Eagles MEM supplemented with 10% fetal bovine serum CFBS and 100 IU/ml penicillin and 100 µg streptomycin per ml.

Mice

Female BALB/cJ (H-$2^d$) mice were purchased from The Jackson Laboratories (Bar Harbor, Me.) and maintained on mouse chow and water ad libitum. All mice were used between the ages of 6 and 15 weeks of age.

Media

Assay Medium for immunological assays was comprised of RPMI 1640 medium supplemented with 10% FBS, 4 mM L-glutamine, 20 mM HEPES (N-2-hydroxyethylpiperazine-N'-2-ethanesulfonate), $5 \times 10^{-5}$M 2-mercaptoethanol, 100 IU penicillin per ml, and 100 µg/ml streptomycin. Stim Medium was comprised of Eagle's Minimum Essential Medium supplemented with 10% FBS, 4 mM L-glutamine, $10^{-4}$M 2-mercaptoethanol, 100 IU penicillin per ml, and 100 µg streptomycin per ml.

Radioimmunoprecipitation Analysis

Cell monolayers were infected at 10 PFU/cell in modified Eagle's methionine-free medium (MEM met-). At 2 hours post-infection, 20 uCi/ml of [$^{35}$S]-methionine were added in MEM (-met) containing 2% dialysed fetal bovine serum (Flow). Cells were harvested at 15 hrs post-infection by resuspending them in lysis buffer (150 mM NaCl, 1 mM EDTA pH 8, 10 mM Tris-HCl (pH 7.4), 0.2 mg/ml PMSF, 1% NP40, 0.01% Na Azide) and 50 µl aprotinin, scraped into eppendorf tubes and the lysate was clarified by spinning 20 minutes at 4° C. One third of the supernatant of a 60 mm diameter Petri dish was incubated with 1 µl normal human serum and 100 µl of protein A-Seraphose CL-4B (SPA) (Pharmacia) for 2 hours at room temperature. After spinning for 1 minute, the supernatant was incubated for 90 min at 4° C. with immune sera specifically recognizing HIV-1, HIV-2, or SIV proteins and 100 µl SPA.

The pellet was washed four times with lysis buffer and two times with lithium chloride/urea buffer (0.2M LiCl, 2M urea, 10 mM Tris-HCl pH 8) and the precipitated proteins were dissolved in 60 µl Laemmli buffer (Laemmli, 1970). After heating for 5 minutes at 100° C. and spinning for 1 minute, proteins were resolved on a SDS 10% polyacrylamide gel and fluorographed.

Inoculations

Mice were intravenously inoculated with $5 \times 10^7$ plaque forming units (PFU) in 0.1 ml of phosphate-buffered saline via the lateral tail vein.

Spleen Cell Preparations

Following euthanasia by cervical dislocation, the spleens of mice were aseptically transferred to a sterile plastic bag containing Hank's Balanced Salt Solution. Individual spleens or pooled spleens from a single experimental group were processed to single cell suspensions by a 1 minute cycle in a Stomacher blender. The spleen cell suspensions were washed several times in either Assay Medium or Stim Medium, as appropriate. The spleen cells were enumerated by the use of a Coulter Counter or by trypan blue dye exclusion using a hemacytometer and microscope.

Sera

Mice were lightly anesthetized with ether and blood was collected from the retroorbital plexus. Blood from mice comprising an experimental group was pooled and allowed to clot. The serum was collected and stored at –70° C. until use.

In Vitro Stimulation for the Generation of Secondary Cytotoxic T Lymphocytes (CTL)

The pooled spleen cells from the various experimental groups (responders) were diluted to $5 \times 10^6$/ml in Stim Medium. The spleen cells from syngeneic, naive mice (stimulators) were diluted to $1 \times 10^7$ cells per ml and infected for 1 hour in tissue culture medium containing 2% FBS at 37° C. with the appropriate poxvirus at an m.o.i. of 25 PFU/cell. Following infection, the stimulator cells were washed several times in Stim Medium and diluted to $1 \times 10^6$ cells per ml with Stim Medium. Five mls of stimulator cells and 5 mls of responder cells were added to a 25 cm$^3$ tissue culture flask and incubated upright at 37° C., in 5% CO$_2$ for 5 days. On the day of the assay, the spleen cells were washed several times in Assay Medium and counted on a hemacytometer in trypan blue with the use of a microscope.

Target Cell Preparation

For poxvirus specific CTL activity, tissue culture cells were infected overnight by incubation at $1 \times 10^7$ cells per ml in tissue culture medium containing 2% FBS at an m.o.i. of 25 PFU/cell for 1 hour at 37° C. Following incubation, the cells were diluted to between $1-2 \times 10^6$ cells per ml with tissue culture medium containing 10% FBS and further incubated at 37° C., in 5% CO$_2$ until use. For HIV specific CTL activity, tissue culture cells were incubated overnight with 20 µg/ml of peptide HBX2 (American Biotechnologies, Cambridge, Mass.), SF2 (American Biotechnologies, Cambridge, Mass.) or MN, (American Biotechnologies, Cambridge, Mass.) corresponding to the V3 loop region of gp120 of HIV-1 isolates III$_B$, SF2, and MN, respectively. On the day of the assay, the targets were washed several times by centrifugation in Assay Medium. After the final wash, the cells were resuspended in approximately 100 µCi of Na$_2$$^{51}$CrO$_4$ ($^{51}$Cr). Following incubation at 37° C. for 1 hr, the cells were washed at least 3 times in Assay Medium by centrifugation, counted on a hemacytometer, and diluted to $1 \times 10^5$/ml in Assay Medium.

Cytotoxicity Assays

For primary CTL assays, freshly prepared spleen cells were diluted with Assay Medium to $1 \times 10^7$ cells per ml. For secondary CTL assays (following either in vivo inoculation or in vitro stimulation), the spleen cells were diluted to $2 \times 10^6$/ml in Assay Medium. One tenth ml of spleen cell suspension was added to $^{51}$Cr labelled target cells in the wells of a 96 well, round-bottom microtiter plate (EXP). In most cases, the spleen cells being assayed for primary CTL activity were further 2-fold diluted in the wells of the microtiter plate prior to the addition of the target cells. As a measure of spontaneous release of $^{51}$Cr (SR), target cells were incubated in only Assay Medium. To determine the maximum release of $^{51}$Cr (MAX), target cells were deliberately lysed at the beginning of the assay by adding 0.1 ml of 10% sodium dodecyl sulfate to the appropriate wells. To initiate the assay, the microtiter plates were centrifuged at 200×g for 2 min and incubated for 4 or 5 hrs at 37° C., in 5% $CO_2$. Following incubation, the culture supernatants of each well were collected using the Skatron Supernatant Collection System. Released $^{51}Cr$ was determined by a Beckman 5500B gamma counter. The percent specific cytotoxicity was determined from the counts by the following formula:

% CYTOTOXICITY=(EXP-MAX)/(MAX-SR)×100

Depletion of T Helper Cells and Cytotoxic T Lymphocytes Using Monoclonal Anti-CD4 and Monoclonal Anti-CD8

Spleen cell suspensions were diluted to a density of $10^7$/ml in cytotoxicity medium (RPMI 1640 containing 0.2% BSA and 5 mM HEPES) containing a 1:5 dilution of anti-CD4 (monoclonal antibody 172.4) or a 1:200 dilution of anti-CD8 (monoclonal antibody anti-Lyt 2.2) and a 1:16 dilution of Cedar Lane Low-Tox rabbit complement. Appropriate controls for the single components (complement, anti-CD4, anti-CD8) were included.

Anti-HIV-1 gp160 ELISA

The wells of ELISA plates (Immulon II) were coated overnight at 4° C. with 100 ng of purified HIV-1 gp160 (Immuno) in carbonate buffer, pH 9.6. The plates were then washed with phosphate-buffered saline containing 0.05% Tween 20 (PBST). The plates were then blocked for 2 hrs at 37° C. with PBST containing 1% bovine serum albumin (BSA). After washing with PBST, sera were initially diluted 1:20 with PBST containing 0.1% BSA (dilution buffer). The sera were further 2-fold serially diluted in the wells of the ELISA plate. The plates were incubated at 37° C. for 2 hrs and washed with PBST. Horseradish peroxidase conjugated rabbit anti-mouse immunoglobulins (DAKO) was diluted 1:2000 in dilution buffer and added to the wells of the ELISA plated and incubated at 37° C. for 1 hour. After washing with PBST, OPD (o-phenylenediamine dihydrochloride) in substrate buffer was added and the color was allowed to develop at ambient temperature for about 20 minutes. The reaction was extinguished by the addition of 2.5M $H_2SO_4$. The absorbance at 490 nm was determined on a Bio-Tek EL-309 ELISA reader. The serum endpoint was defined as the reciprocal of the dilution giving an absorbance value of 1.0.

Lymphocyte Proliferation Assays

Single cell suspensions of the spleen cells of individual mice were diluted to $2×10^6$/ml in Assay Medium and 0.1 ml were added to the wells of 96 well, flat-bottom microtiter plates containing Assay Medium alone, 1, 5, or 10 μg of HIV-1 peptide T1, 1, 5, or 10 μg of HIV-1 peptide T2, and 1 or 10 μg of purified HIV-1 gp160 (Immuno). The cells were incubated for 5 days at 37° C., in 5% $CO_2$. To each well was added 1.0 μCi of [$^3$H]-thymidine for the final 6 hrs of incubation and then harvested onto Beckman Ready Filters using a Cambridge PHD cell harvester. The filter disks were dry-counted in a liquid scintillation counter.

STIMULATION INDEX=$CPMs_{EXP}$/$CPMs_{MEDIUM}$

EXAMPLE 1

ATTENUATED VACCINIA VACCINE STRAIN NYVAC

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al. (1990a,b).

The deletion loci were also engineered as recipient loci for the insertion of foreign genes.

The regions sequentially deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R+B14R) vP553;

(3) A type inclusion body region (ATI; A26L) vP618;

(4) hemagglutinin gene (HA; A56R) vP723;

(5) host range gene region (C7L-K1L) vP804; and (6) large subunit, ribonucleotide reductase (I4L) vP866 (NYVAC).

As described in following Examples, any or any combination of these regions can be a site either alone or in combination with other sites for inserting exogenous DNA from an immunodeficiency virus, immunodeficiency viruses or from such virus or viruses and other exogenous DNA to obtain a useful recombinant.

(1) Construction of Plasmid pSD460 for Deletion of Thymidine Kinase Gene (J2R)

Referring now to FIG. 1, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

MPSYN43 5'     TAATTAACTAGCTACCCGGG         3'
MPSYN44 3' GTACATTAATTGATCGATGGGCCCTTAA 5'
              NlaIII                      EcoRI were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

```
                HindIII      SmaI
MPSYN45 5'  AGCTTCCCGGGTAAGTAATACGTCAAGGAGAAAACGAA
MPSYN46 3'      AGGGCCCATTCATTATGCAGTTCCTCTTTTGCTT NotI            SspI
      ACGATCTGTAGTTAGCGGCCGCCTAATTAACTAAT   3'MPSYN45
      TGCTAGACATCAATCGCCGGCGGATTAATTGATTA   5'MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus vP410 was identified by plaque hybridization.

pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
          ClaI               SacI      XhoI           HpaI
SD42mer 5' CGATTACTAGATCTGAGCTCCCCGGGCTCGAGGGATCCGTT  3'
SD40mer 3' TAATGATCTAGACTCGAGGGGCCCGAGCTCCCTAGGCAA    5'
               BglII          SmaI         BamHI
```

(2) Construction of Plasmid pSD486 for Deletion of Hemorrhagic Region (B13R+B14R)

Figure 2:
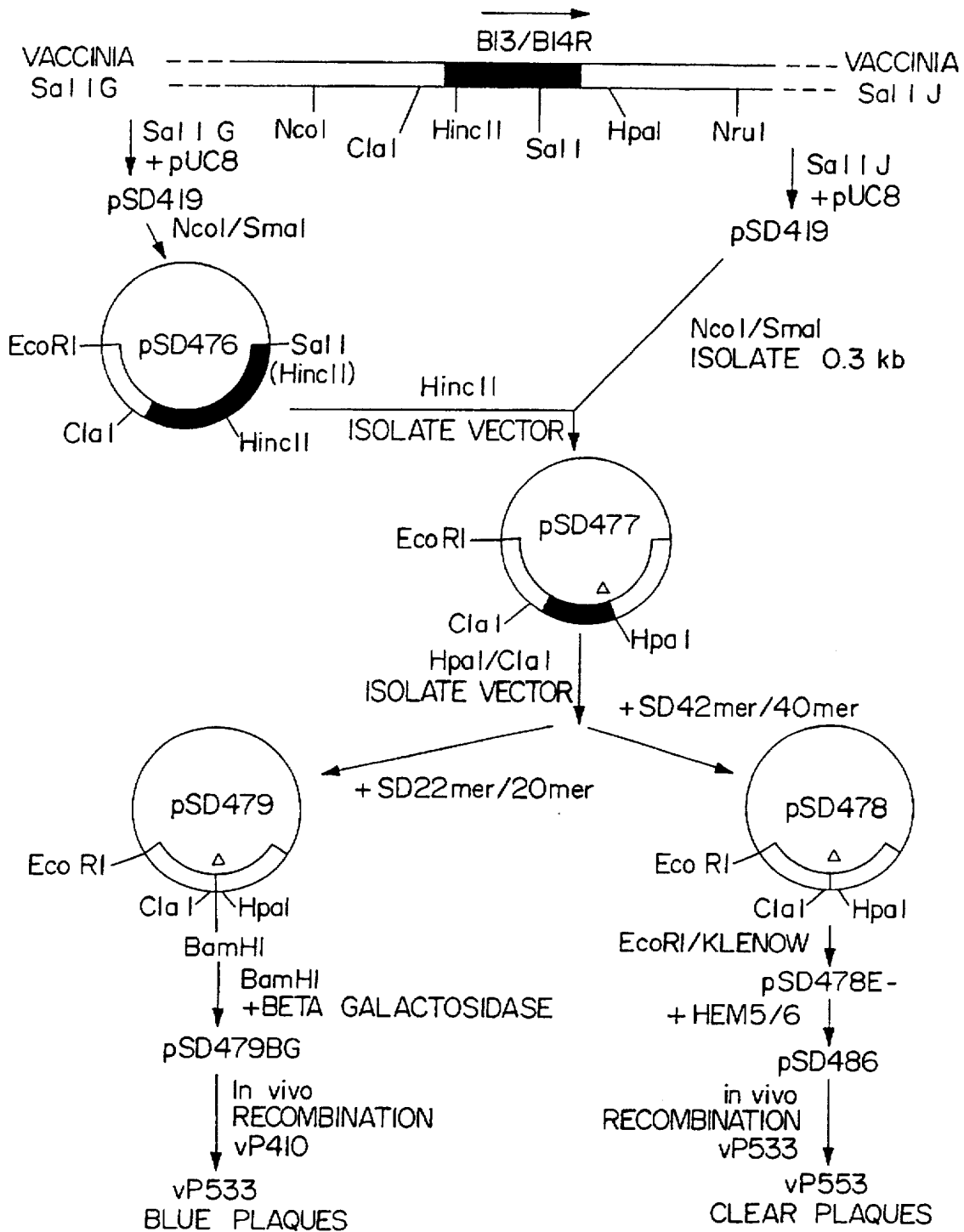
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NcoI/SmaI followed by blunt ending with Klenow fragment of *E. coli* polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7).

```
            ClaI              BamHI  HpaI
SD22mer 5' CGATTACTATGAAGGATCCGTT 3'
SD20mer 3'    TAATGATACTTCCTAGGCAA 5'
``` generating pSD479. pSD479 contains an initiation codon (underlined) followed by a BamHI site. To place *E. coli* Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E$^-$. pSD478E$^-$ was digested with BamHI and HpaI and ligated with annealed synthetic oligonucleotides HEM5/HEM6 (SEQ ID NO:10/SEQ ID NO:11)

```
          BamHI    EcoRI   HpaI
HEM5 5' GATCCGAATTCTAGCT 3'
HEM6 3'     GCTTAAGATCGA 5'
``` generating plasmid pSD486. pSD486 was used as donor plasmid for recombination with recombinant vaccinia virus vP533, generating vP553, which was isolated as a clear plaque in the presence of X-gal.

(3) Construction of Plasmid pMP494Δ for Deletion of ATI Region (A26L)

Figure 3:
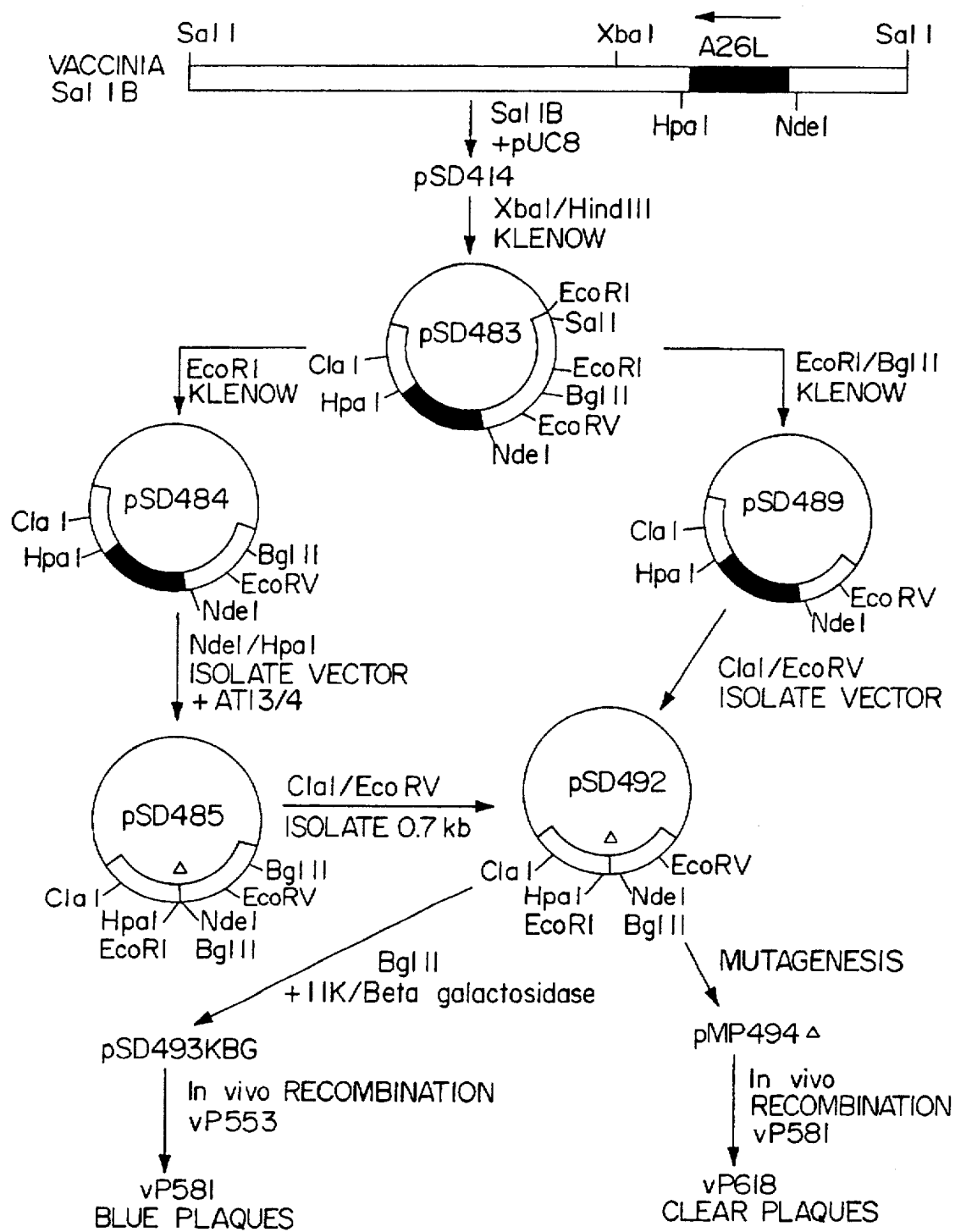
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of *E. coli* polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

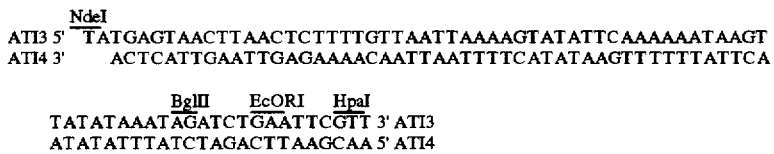

reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSY62 (SEQ ID NO:16), MPSYN60 (SEQ ID NO:17), and MPSYN 61 (SEQ ID NO:18)

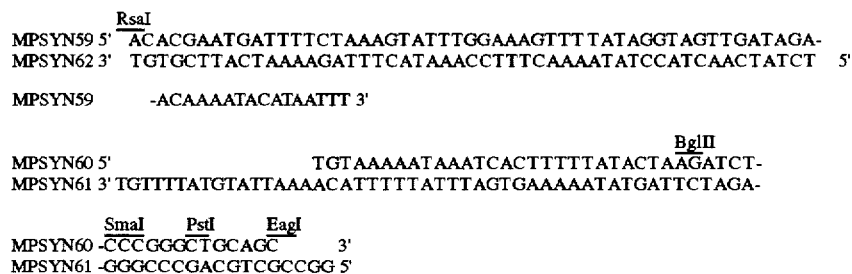

pSD492. The BglII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTT-TATATAACTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

(4) Construction of Plasmid pSD467 for Deletion of Hemagglutinin Gene (A56R)

Figure 4:
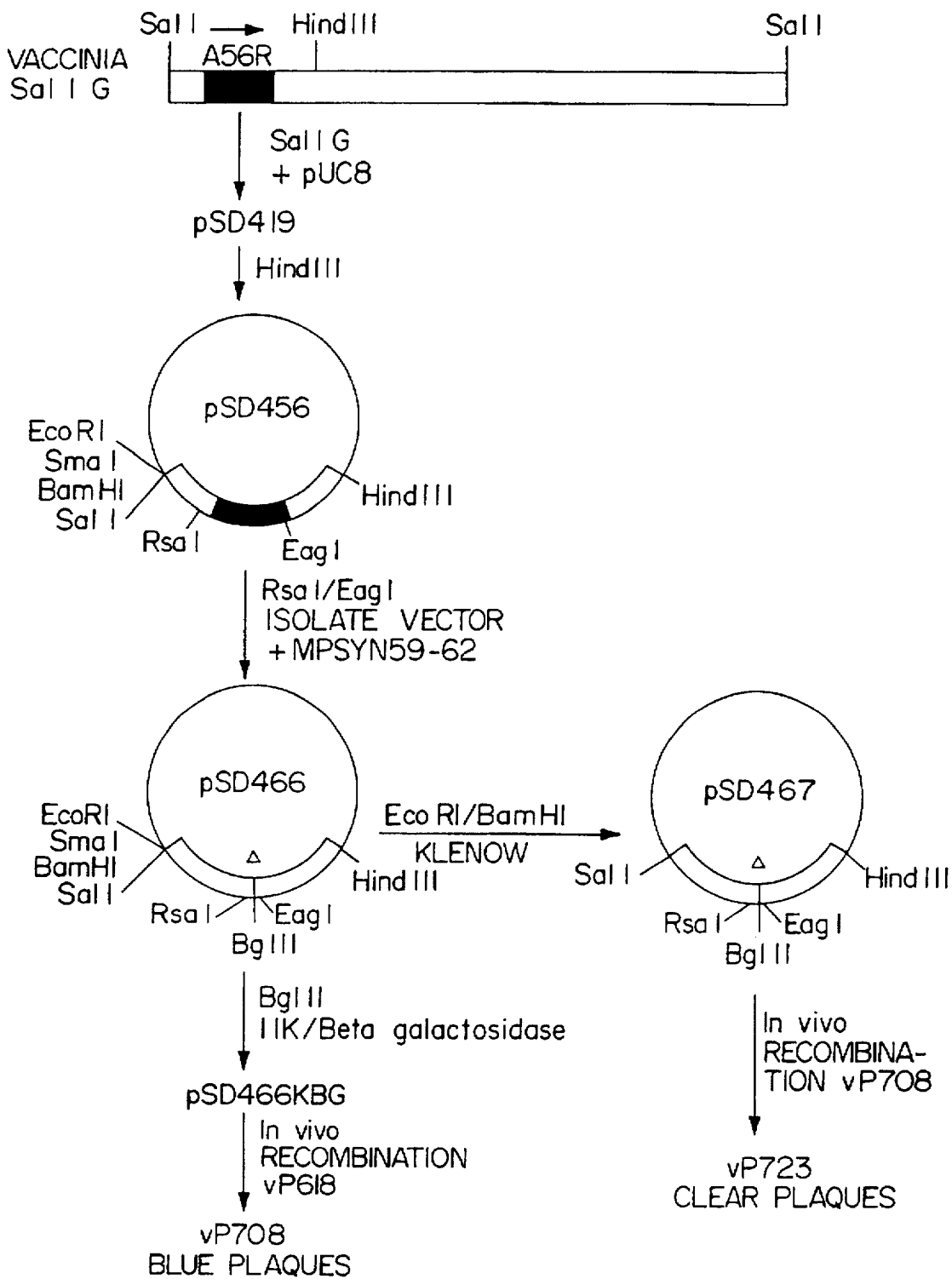
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG.

reconstructing the DNA sequences upstream from the A56R ORF and replacing the A56R ORF with a polylinker region as indicated above. The resulting plasmid is pSD466. The vaccinia deletion in pSD466 encompasses positions [161, 185–162,053]. The site of the deletion in pSD466 is indicated by a triangle in FIG. 4.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

(5) Construction of Plasmid pMPCSK1Δ for Deletion of Open Reading Frames [C7L–K1L]

Figure 5:
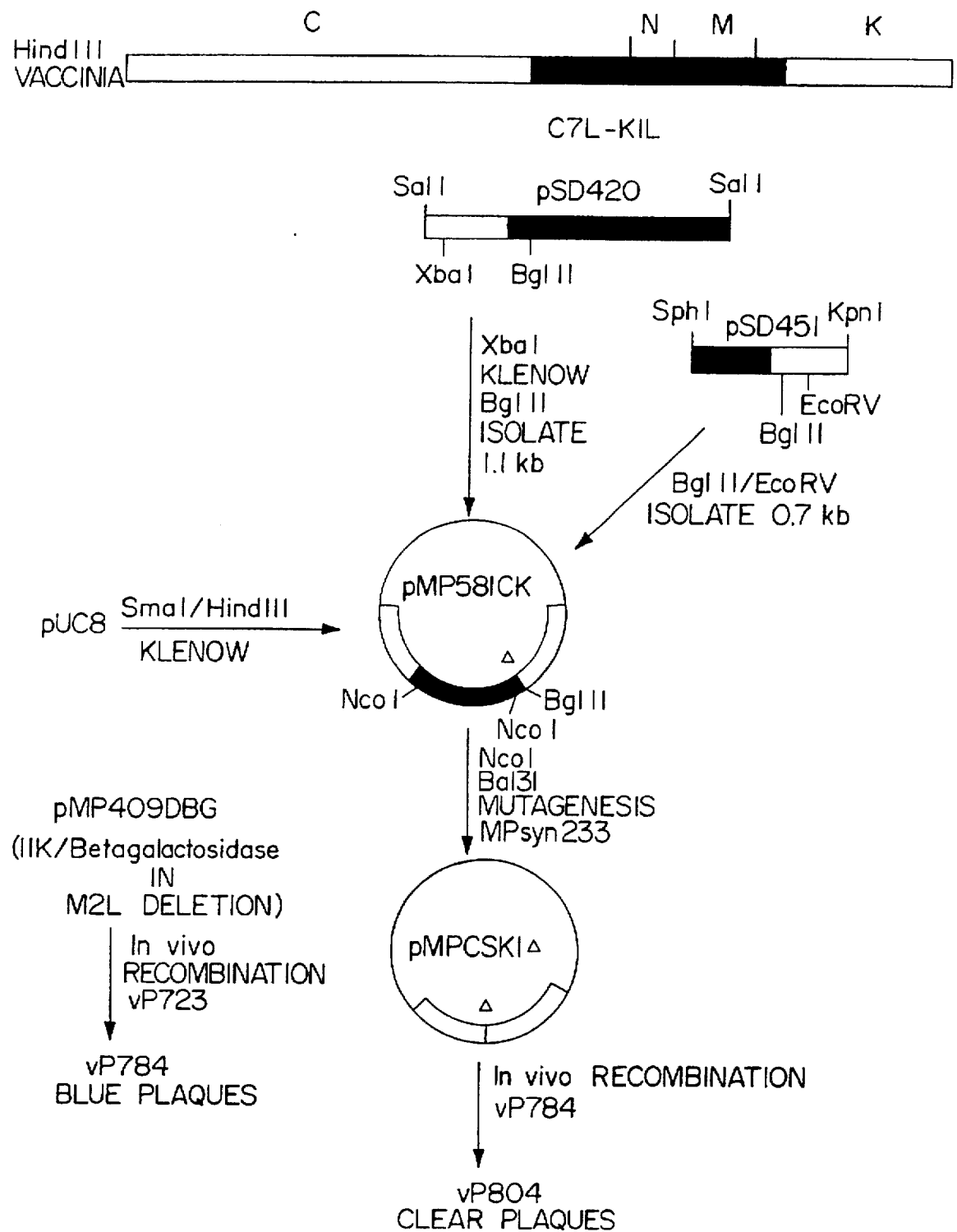
FIG. 5 schematically shows a method for the construction of plasmid pMPCSK1Δ for deletion of gene cluster [C7L–K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide.

```
                            BglII
MPSYN82  (SEQ ID NO:19) 5' TTTCTGTATATTTGCACCAATTTAGATCTTACTC
                           AAAATATGTAACAATA 3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

and the Beta-galactosidase containing vaccinia recombinant, vP784, resulted in vaccinia deletion mutant, vP804, which was isolated as a clear plaque in the presence of X-gal.

(6) Construction of Plasmid pSD548 for Deletion of Large Subunit, Ribonucleotide Reductase (I4L)

Figure 6:
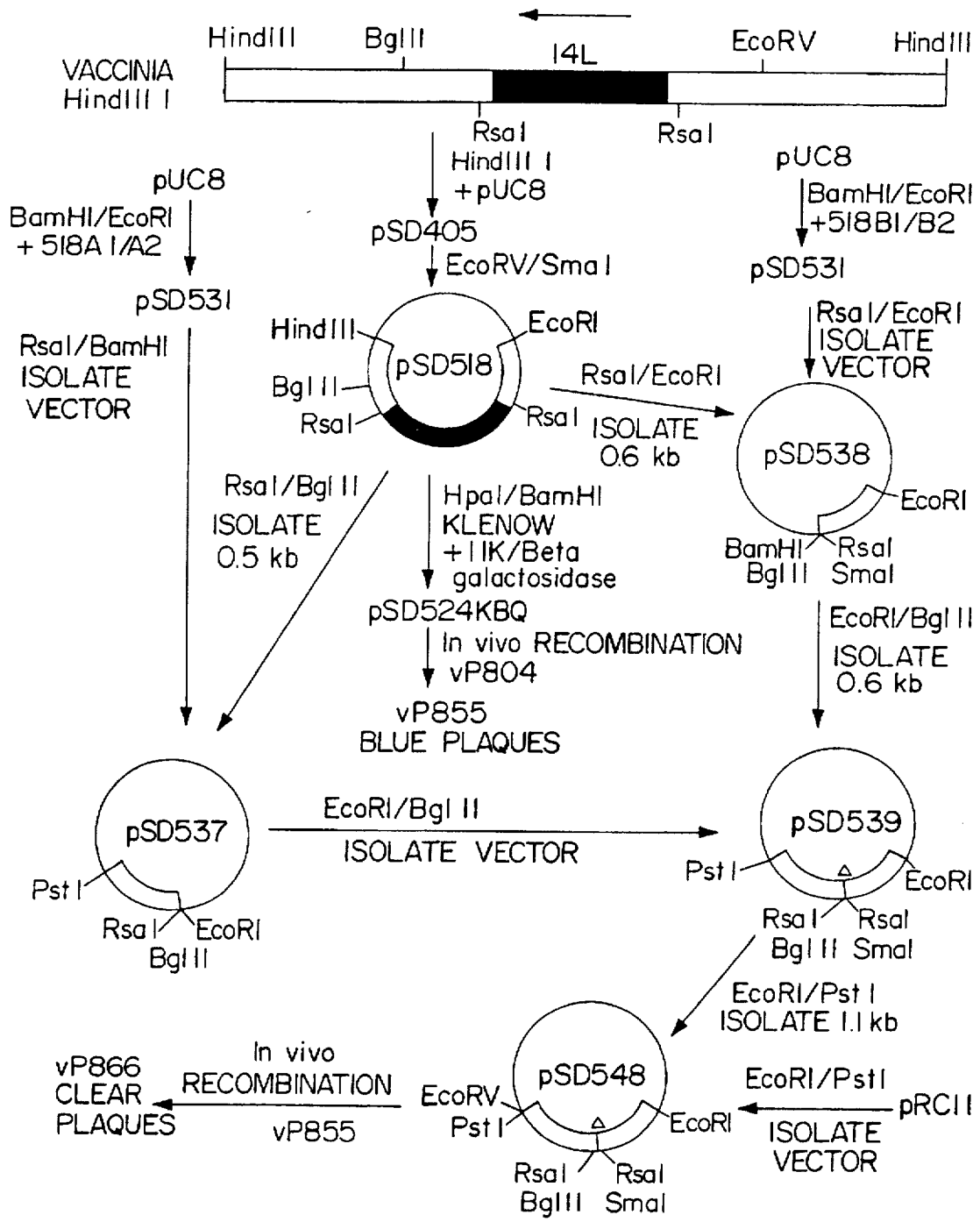
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

```
         BamHI    RsaI
518A1 5' GATCCTGAGTACTTTGTAATATAATGATATATATTTTCACTTTATCTCAT
518A2 3'     GACTCATGAAACATTATATTACTATATATAAAAGTGAAATAGAGTA

BglII    EcoRI
         TTGAGAATAAAAAGATCTTAGG         3' 518A1
         AACTCTTATTTTTCTAGAATCCTTAA 5' 518A2
```

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5' TGTCATTTAACACTATACTCATAT-TAATAAAAATAATATTTATT 3'. The resulting plasmid, pMPCSK1Δ, is deleted for vaccinia sequences positions 18,805–29,108, encompassing 12 vaccinia open reading frames [C7L–K1L]. Recombination between pMPCSK1Δ forming plasmid pSD531. pSD531 was cut with RsaI (partial) and BamHI and a 2.7 kb vector fragment isolated. pSD518 was cut with BglII (pos. 64,459)/ RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

```
         BamHI BglII   SmaI
518B1 5' GATCCAGATCTCCCGGGAAAAAAATTATTTAACTTTTCATTAATAGGGATTT
```

-continued

```
518B2 3'  GTCTAGAGGGCCCTTTTTTTAATAAATTGAAAAGTAATTATCCCTAAA
```

```
                    RsaI    EcoRI
         GACGTATGTAGCGTACTAGG         3' 518B1
         CTGCATACTACGCATGATCCTTAA 5' 518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb) forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

EXAMPLE 2

EXPRESSION OF HIV GENE PRODUCTS BY HOST-RESTRICTED POXVIRUSES

This Example describes the generation of host-restricted poxviruses that express HIV gene products. The vectors employed are NYVAC, ALVAC and TROVAC.

ALVAC and NYVAC Recombinants Containing the HIV-1 (IIIB) V3 Loop and Epitope 88

A 150 bp fragment encompassing the V3 loop (amino acids 299–344; Javeherian et al., 1989; La Rosa et al., 1990) of HIV-1 (IIIB) was derived by PCR using oligonucleotides HIV3BL5 (SEQ ID NO:25) (5'-ATGGTAGAAATTAATTGTAC-3') and HIV3BL3 (SEQ ID NO:26) (5'-ATCATCGAATTCAAGCTTATTATTTTGCTC-TACTAATGTTAC-3') with pHXB.2D (III) as template (provided by Dr. R. C. Gallo, NCI-NIH, Bethesda, Md.). Oligonucleotides HIV88A (SEQ ID NO:27) (5'-ATGAATGTGACAGAAAATTTTAACATGTGG-AAAAATGTAGAAATTAATTGTACAAGACCC-3') and HIV88B (SEQ ID NO:28) (5'-GGGTCTTGTACAATTAATTTCTACATTTTTCCACAT-GTTAAAATTTTCTGTCACATTCAT-3') were annealed together to produce a double-stranded fragment containing the HIV-1 epitope 88 (amino acids 95–105, Shaffermann et al., 1989). The 150 bp V3-containing PCR fragment containing the epitope and the 42 bp fragment containing the 88 epitope sequences were fused together by PCR by virtue of the existence of complementary sequences. The reactions were performed using oligonucleotides HIV88C (SEQ ID NO:29) (5'-AGTAATGTGACAGAAAATTTTAAC-3') and HIV3BL3. The 192 bp PCR-derived fragment contains the epitope 88 sequences fused upstream to the V3 loop sequences. A termination codon (TAA) was incorporated into oligonucleotide HIV3BL3P to terminate translation of the open reading frame and an initiation codon was incorporated into oligonucleotide HIV88C to serve as the start of translation to express the epitope 88/V3 loop fusion protein. Additionally, oligonucleotide HIV3BL3 was synthesized so that an EcoRI site existed at the 3'-end of the 192 bp PCR fragment.

The entomopoxvirus promoter, 42 kDa (early) was generated by PCR using oligonucleotides RG273 (SEQ ID NO:30) (5'-AGGCAAGCTTTCAAAAAAATATAAATGATTC-3') and RG274 (SEQ ID NO:31) (5'-TTTATATTGTAATTATATATTTTC-3') with plasmid, pAM12, as template. The 108 bp fragment containing the 42 kDa promoter was synthesized to contain a HindIII site at the 5'-end. The 42 kDa promoter containing segment was kinased and digested with HindIII prior to ligation to the epitope 88/V3 fragment digested with EcoRI and pRW831 digested with HindIII and EcoRI. The resultant plasmid was designated as pC5HIVL88. This plasmid was used in in vitro recombination assays with CPpp as rescue virus to generate vCP95. ALVAC recombinant, vCP95, contains the epitope 88/V3 loop in the de-ORFed C5 locus of CPpp.

The plasmid pC5HIVL88 was digested with HindIII and EcoRI to liberate a 300 bp fragment containing the epitope 88/V3 expression cassette described above. This fragment was excised from a LMP-agarose gel and isolated by phenol extraction (2X) and ether extraction (1X). The isolated fragment was blunt-ended using the Klenow fragment of the E. coli DNA polymerase in the presence of 2 mM dNTPs. The blunted fragment was ligated to pSD550VC digested with SmaI to yield plasmid pHIVL88VC. This plasmid was used with vP866 as the rescue virus to generate vP878. vP878 contains the epitope 88/V3 loop cassette in the de-ORFed I4L locus of vP866.

ALVAC- and NYVAC-Based Recombinants Expressing the HIV-1 (IIIB) Envelope Glycoproteins An expression cassette composed of the HIV-1 (IIIB) env gene juxtaposed 3' to the vaccinia virus H6 promoter (Guo et al., 1989; Taylor et al., 1988a,b) was engineered for expression of gp160 from HIV-1 by the ALVAC and NYVAC vectors. A 1.4 kb fragment was amplified from pHXB.2D (III) (provided by Dr. R. C. Gallo, NCI-NIH, Bethesda, Md.) using oligonucleotides HIV3B1 (SEQ ID NO:32) (5'-GTTTTAA-TTGTGGAGGGGAATTCTTCTACTGTAATTC-3') and HIV3B5 (SEQ ID NO:33) (5'-ATCA-TCTCTAGAATAAAAATTATAGCAAAATCCTTTC-3'). This fragment contains the 3' portion of the env gene. PCR amplification with these primers placed a vaccinia virus early transcription termination T5NT sequence motif following the coding sequence and removed the T5NT motif situated at position 6146 to 6152 (Ratner et al., 1985) without altering the amino acid sequence. This change (T to C) creates an EcoRI site (GAATTC) at this position. This 1.4 kb fragment was digested with EcoRI (5'-end) and XbaI (3'-end) and inserted into EcoRI and XbaI digested pBS-SK (Stratagene, La Jolla, Calif.). The resultant plasmid was designated as pBSHIVENV1.5. Nucleotide sequence analysis of this fragment demonstrated that the sequence was entirely correct except for a T to C transition at position 7048. This transition was corrected as follows: A 250 bp fragment was derived by PCR using oligonucleotides HIV3B1 (SEQ ID NO:32) (5'-GTTTT-AATTGTGGAGGGGAATTCTTCTACTGTAATTC-3') and HIV3B17 (SEQ ID NO:34) (5'-TGCTACTCCTAATGGTTC-3') with pHXB.2D (III) as template. This fragment was digested with BglII and EcoRI. The fragment was inserted into pBSHIV3B1.5, digested with BglII and EcoRI and thus substituted for the region with the incorrect nucleotide to yield plasmid pBSHIV3B3P.

PCR was utilized to derive a 150 bp fragment containing the 5' portion of the env gene with oligonucleotides HIV3B9 (SEQ ID NO:35) (5'-CATATGCTTTAGCATCTGATG-3') and HIV3B10 (SEQ ID NO:36) (5'-ATGAAAGAGCAGAAGACAGTG-3') with pHXB.2D (III) as template. PCR was also used to generate a 128 bp fragment containing the vaccinia virus H6 promoter from pC3FGAG using oligonucleotides VV6K5P (SEQ ID NO:37) (5'-ATCATCGGTACCGATTCTTTATTCTATAC-3') and VVH63P (SEQ ID NO:38) (5'-TACGATACAAACTTAACGG-3'). Both fragments were digested with KpnI and the 150 bp fragment was kinased prior to co-insertion of these fragments into pBS-SK digested with KpnI. The resultant plasmid was designated as pBSH6HIV3B5P.

PCR was used to generate a 600 bp fragment from pHXB.2D (III) with oligonucleotides HIV3B2 (SEQ ID NO:39) (5'-GAATTACAGTAGAA-GAATTCCCCTCCACAATTAAAAC-3') and HIV3B7 (SEQ ID NO:40) (5'-CAATAGATAATGATACTAC-3'). This fragment was digested with EcoRI and kinased. PCR was also used to derive a 500 bp fragment with the same template but with oligonucleotides HIV3B6 (SEQ ID NO:41) (5'-GTATTATATCAAGTTTATATAATAATGCATATTC-3') and HIV3B8 (SEQ ID NO:42) (5'-GTTGATGATCTGTAGTGC-3'). This fragment was digested with KpnI. These fragments together correspond to nucleotide 5878 to 6368 (Ratner et al., 1985). The engineering of these fragments with these primers also removes a T5NT sequence positioned at nucleotide 6322 to 6328 without altering the amino acid sequence. These two fragments were inserted into pBSHIV3B3P digested with KpnI and EcoRI. This plasmid was designated as pBSHIV3BP2768.

Plasmid pBSH6HIV3B5P was digested with KpnI to liberate a 360 bp fragment containing the H6 promoter and the 5' portion (150 bp) of the HIV-1 env gene. This KpnI fragment was ligated into pBSHIV3B3P2768 digested with KpnI to yield plasmid pBSHIV3BEII. A 2.8 kb fragment was derived from pBSHIV3BEII by digestion with XbaI followed by a partial KpnI digestion. This fragment was blunt-ended and inserted into SmaI digested pSD550. The plasmid pI4LH6HIV3B was generated and used in recombination experiments with vP866 as the rescue virus. This generated vP911 which contains the HIV-1 env gene in the I4L locus of the NYVAC genome.

To insert the HIV-1 env gene into an ALVAC vector, pBSHIV3BEAII was digested with NruI and XbaI. The derived 2.7 kb fragment was blunt-ended with the Klenow fragment of the *E. coli* DNA polymerase in the presence of 2 mM dNTPs. This fragment contains the entire HIV-1 env gene juxtaposed 3' to the 3'-most 21 bp (to NruI site) of the vaccinia H6 promoter. This fragment was ligated to a 3.1 kb fragment derived by digestion of pRW838 with NruI and EcoRI with subsequent blunt-ending with Klenow. The pRW838 derived fragment contains the homologous arms derived from canarypox to direct the foreign gene to the C5 locus. It also contains the 5'-most 100 bp of the H6 promoter. Therefore, ligation of these fragments resulted in an insertion plasmid containing an expression cassette for the HIV-1 env gene and was designated pC5HIV3BE. This plasmid was used in in vitro recombination experiments with ALVAC as the rescue virus to generate vCP112.

NYVAC-Based Recombinants Expressing the HIV-1 (IIIB) gp120

The plasmid pBSHIV3BEAII was digested with EcoRI and XbaI to liberate a 4.3 kb fragment. This fragment contains the vaccinia virus H6 promoter linked to the HIV-1 env gene to nucleotide 6946 (Ratner et al., 1985). The 4.3 kb fragment was ligated to 300 bp EcoRI/XbaI digested PCR-derived fragment corresponding to the 3' portion of the gp120 coding sequence. The 300 bp PCR fragment was derived using oligonucleotides HIV1-120A (SEQ ID NO:43) (5'-ATCATCTCTAGAATAAAAATTATGGTTC-AATTTTTACTACTTTTATATTATATATTTC-3') and HIV1-120B (SEQ ID NO:44) (5'-CAATAATCTTTAAGCAAATCCTC-3') with pHXB.2D (III) as template. The ligation of the 4.3 kb XbaI/EcoRI fragment and the 300 bp XbaI/EcoRI fragment yielded plasmid pBSHIVB120.

A 1.6 kb KpnI/XbaI fragment was derived from pBSHIVB120 by initially linearizing the plasmid with XbaI followed by a partial KpnI digestion. The 1.6 kb fragment was blunt-ended by treatment with the Klenow fragment of the *E. coli* DNA polymerase in the presence of 2 mM dNTPs. This fragment was inserted into pSD541 digested with SmaI to yield pATIHIVB120. This plasmid was used in in vitro recombination experiments to generate vP921. This recombinant contains the portion of the HIV-1 env gene encoding gp120 in the ATI locus of NYVAC.

To determine the authenticity of the HIV-1 gene products expressed by vP911, vP921 and vCP112, immunoprecipitation analyses were performed.

Lysates derived from the infected cells were analyzed for HIV-1 env gene expression using pooled serum from HIV-1 seropositive individuals (obtained from Dr. Genoveffa Franchini, NCI-NIH, Bethesda, Md.). The sera was preadsorbed with vP866-infected Vero cells. The preadsorbed human sera was bound to protein A-sepharose in an overnight inoculation at 4° C. In some cases a monoclonal antiserum specific to gp120 (Dupont) was used as the primary serum and a rat anti-mouse as the second antibody. Following this incubation period, the material was washed 4 times with 1X Buffer A. Lysates precleared with normal human sera and protein A-Sepharose were then incubated overnight at 4° C. with the human sera from seropositive individuals bound to protein A-Sepharose. Following the overnight incubation period, the samples were washed four times with 1×Buffer A and 2×with $LiCl_2$/urea buffer. Precipitated proteins were dissociated from the immune complexes by the addition of 2×Laemmli's buffer (125 mM Tris (pH6.8), 4% SDS, 20% glycerol; 10% 2-mercaptoethanol) and boiling for 5 minutes. Proteins were fractionated on a 10% Dreyfuss gel system (Dreyfuss et al., 1984) fixed and treated with 1M - Na - salicylate for fluorography.

The results of immunoprecipitation using sera pooled from HIV-1 seropositive individuals showed specific precipitation of the gp120 and gp41 mature forms of the gp160 envelope glycoprotein from vP911 infected cell lysates. No such specific gene products can be detected in the parental virus (NYVAC; vP866) infected cell lysates. Specific precipitation of gp120 was also found in vP921 infected cell lysates.

Immunofluorescence analysis with the same sera illustrated that the gp160 and gp120 species expressed by vP911 and vP921, respectively, were present on the surface of infected cells.

Immunoprecipitation was also performed with vCP112 infected CEF cells. No HIV-specific polypeptides were precipitated with a monoclonal antibody directed against the gp120 extracellular moiety from cells infected with the ALVAC parental virus and uninfected CEF cells. Two HIV-specific polypeptides species were, however, precipitated from vCP112 infected cells. These species migrated with apparent mobilities of 160 kDa and 120 kDa, corresponding to the precursor env gene product and the mature extracellular form, respectively.

A Recombinant Vaccinia Virus Expressing HIV gp120 Elicits Primary HIV-specific Cytotoxic T Lymphocyte Activity Following iv administration with $5\times10^7$ PFUs of vaccinia virus recombinants vP878, vP911, or vP921, or, as a control, with NYVAC, the vector, splenic CTL activity of BALB/c mice was assessed against syngeneic P815 cells which had been incubated overnight with peptide HBX2 (Table 1). Modest, but significant ($P<0.05$) primary CTL activity was generated in the spleens of mice administered vP921, expressing HIV gp120. No other recombinant vaccinia virus nor the vector was able to elicit primary HIV-specific CTL activity. This was not due to inadequate infection as each group of mice administered a vaccinia virus responded with primary vaccinia-specific CTL activity. Control, unimmunized mice responded to neither target.

Recombinant Poxviruses Expressing HIV env Peptides Generate HIV-Specific Memory Cytotoxic T Lymphocytes At least one month following a single inoculation with one of the recombinant vaccinia viruses, mouse spleen cells were stimulated in vitro with syngeneic, naive spleen cells previously infected with NYVAC or with each of the HIV recombinant vaccinia viruses (Table 2). Strong HIV-specific CTL activity was detected only in the spleen cell cultures of mice immunized with vP878, vP911, and vP921 which were restimulated in vitro by cells infected with one of the same vaccinia virus HIV recombinants (vP878, vP911, or vP921). The vaccinia virus recombinants expressing HIV gp120 or gp160 were better able to generate memory CTLs than the vaccinia virus recombinant expressing only the V3 loop fused to the 88 epitope. HIV-specific memory CTL activity could not be elicited from unimmunized control or NYVAC immunized spleen cells. The absence of HIV-specific CTL activity from vector immunized mice could not be attributed to poor immunization since vaccinia-specific memory CTL activity was apparent after in vitro stimulation with spleen cells infected with any of the vaccinia viruses used.

In a similar study, the ability of a canarypox recombinant expressing the V3 loop region fused to the 88 epitope (vCP95) to generate HIV-specific memory CTLs was examined (Table 3). Three weeks following a single inoculation of $10^8$ PFUs of vCP95 or the canarypox vector, CPpp, HIV-specific memory CTL responses were compared to that elicited by the recombinant vaccinia virus analog, vP878. Vaccinia and canarypox CTL responses were included as controls for proper immunization. Only spleen cells from vP878 and vCP95 immunized mice produced HIV-specific memory CTL activity which could be stimulated by vP878. The inability of vCP95 to stimulate existing memory CTLs to functional cytolytic CTLs may have been related to the in vitro conditions employed which were maximized based upon the use of vaccinia virus recombinants. Nonetheless, vCP95 was fully capable of generating significant HIV-specific memory CTLs in the spleens of immunized mice.

Characterization of the In Vitro Stimulated Cytotoxic Cells

It is conceivable that the cells mediating cytotoxicity against the HIV peptide-pulsed target cells represent a population of nonspecific effector cells unrelated to CTLs, such as natural killer cells. To test this, the spleen cells of mice immunized with vP921 and restimulated in vitro with vP921 infected spleen cells were depleted of T-lymphocytes bearing surface antigens characteristic of T helper lymphocytes (CD4) or of cytotoxic T lymphocytes (CD8) and assayed against V3 loop peptide pulsed target cells (Table 4). As before, only vP921 immunized mice generated memory HIV-specific CTL activity which could be stimulated in vitro with vP921 infected syngeneic spleen cells. Although the complement preparation (C') and the monoclonal anti-CD4 and anti-CD8 produced some toxic effects, only the cultures depleted of CD8-bearing cells (anti-CD8+C') were also depleted of HIV-specific cytotoxic effector cells. Thus, the cells mediating cytolytic activity against the HIV peptide-pulsed target cells possessed CD8 antigens on their cell membranes, a characteristic of MHC class I restricted CTLs.

Specificity of CTL Antigen Receptor Recognition of the V3 Loop Region of HIV gp120

T lymphocyte antigen receptors are exquisitely sensitive to small alterations in the primary amino acid sequence of the epitope fragment. The V3 loop region of HIV gp120 is hypervariable and differs immunologically among HIV isolates. The hypervariability resides in substitutions and additions of only a few amino acids. To examine the specificity of cytotoxic cells generated by HIV vaccinia virus recombinants, susceptibility to CTL activity was compared among P815 target cells pulsed with peptides corresponding the V3 loop region of HIV isolates $III_B$, SF2, and MN. Only immunization with vP911 and vP921 induced HIV specific primary CTL activity (Table 5). Furthermore, HIV specific CTL activity was confined only to P815 target cells pulsed with peptide corresponding to the V3 loop of HIV isolate $III_B$. Similar results were obtained with in vitro stimulated, HIV specific secondary CTL activity induced by immunization with the vaccinia virus recombinants vP878, vP911, and vP921 (Table 6). Thus, HIV specific CTLs elicited by recombinant vaccinia viruses expressing various portions of the env gene of HIV isolate $III_B$ recognize only target epitopes derived from the same antigenic isolate.

Lymphocyte Proliferation Responses to HIV Epitopes Following Immunization with Vaccinia Virus HIV Recombinants Lymphocyte proliferation to antigens is an in vitro correlate of cell-mediated immunity. Presentation of the appropriate antigen induces cellular proliferation in the immune population of cells expressing receptors for the antigen. The initiation and continuation of proliferation requires the involvement of T helper lymphocytes via soluble mediators. To evaluate cell-mediated immunity to HIV antigens in mice immunized with recombinant vaccinia viruses expressing HIV antigens, spleen cells from mice immunized 27 days earlier were incubated for 5 days with peptides correlating to T helper lymphocyte epitopes designated $T_1$ and $T_2$, as well as with purified HIV gp160 (Table 7). No proliferative responses to the T helper cell epitopes $T_1$ and $T_2$ were observed in any of the spleen cell cultures. However, the spleen cells of mice previously immunized with vP921 vigorously responded to HIV gp160 as determined by the incorporation of [$^3$H]-thymidine. A stimulation index (SI) of greater than 2.0 is considered indicative of immunity. Thus, inoculation of mice with vP921 elicited cell-mediated immunity to HIV gp160.

Antibody Responses of Mice Inoculated with Vaccinia Virus HIV Recombinants

To evaluate humoral responses to HIV, mice were immunized at day 0 with one of the vaccinia virus HIV recombinants and received a secondary immunization at week 5. The mice were bled at various intervals through 9 weeks after the initial immunization. Pooled sera from each treatment group were assayed for antibodies to HIV by ELISA employing purified gp160 as antigen (Table 8). Primary antibody responses were generally modest, but detectable with the highest levels induced by vP911. Following the secondary immunization, the antibody titers of mice immunized with vP911 and vP921 increased and peaked at week 7 with titers of over 4,600 and 3,200, respectively, before declining slightly by week 9. Thus, two vaccinia virus HIV recombinants, vP911 and vP921, were capable of inducing a significant antibody response.

TABLE 1

Primary CTL activity of spleen cells from mice immunized with vaccinia virus recombinants against vaccinia virus infected targets and targets pulsed with peptide corresponding to the V3 loop region of HIV-1 gp120.

| IMMUNIZATION | | PERCENT CYTOTOXICITY TARGET | | |
|---|---|---|---|---|
| | | P815 | VAC | HIV V3 |
| NONE | | −3.5 | −0.6 | −4.8 |
| | ± | 2.0 | 1.5 | 1.6 |
| NYVAC | | −4.4 | 9.5* | −5.9 |
| | ± | 1.9 | 3.2 | 1.7 |
| vP878 | | −4.9 | 7.1* | −4.0 |
| | ± | 1.8 | 2.2 | 1.2 |
| vP911 | | −4.0 | 4.6* | 1.4 |
| | ± | 2.5 | 2.0 | 5.1 |
| vP921 | | −3.4 | 10.7* | 15.5* |
| | ± | 0.9 | 1.5 | 2.8 |

E:T = 100:1
* P < 0.05 vs appropriate controls, Student's t-test

TABLE 2

Secondary CTL activity of spleen cells following in vitro stimulation with vaccinia virus recombinants.

| IMMUNIZATION | | PERCENT CYTOTOXICITY TARGET | | |
|---|---|---|---|---|
| in vivo | in vitro | P815 | VAC | HIV V3 |
| NONE | NONE | −0.1 | 1.9 | 0.5 |
| | NYVAC | 3.7 | 8.9 | 3.8 |
| | vP878 | 4.6 | 9.0 | 5.5 |
| | vP911 | −1.7 | 2.9 | 4.8 |
| | vP921 | 2.9 | 2.9 | 1.5 |
| NYVAC | NONE | 0.0 | 4.4 | 1.1 |
| | NYVAC | 3.5 | 47.8* | 9.2 |
| | vP878 | 6.3 | 44.1* | 14.4 |
| | vP911 | 7.9 | 48.6* | 10.6 |
| | vP921 | 6.8 | 50.8* | 7.9 |
| vP878 | NONE | 0.1 | 1.7 | 1.3 |
| | NYVAC | 10.2 | 58.5* | 13.0 |
| | vP878 | 11.6 | 57.9* | 59.9* |
| | vP911 | 7.8 | 56.2* | 40.8* |
| | vP921 | 4.9 | 42.0* | 14.8 |
| vP911 | NONE | 0.3 | 2.9 | 4.0 |
| | NYVAC | 6.2 | 50.7* | 8.5 |
| | vP878 | 5.9 | 50.9* | 77.4* |
| | vP911 | 5.0 | 54.2* | 82.6* |
| | vP921 | 10.9 | 55.0* | 87.8* |
| vP921 | NONE | 2.9 | 5.0 | 9.4 |
| | NYVAC | 8.3 | 54.4* | 22.7 |
| | vP878 | 10.4 | 56.2* | 85.6* |
| | vP911 | 8.7 | 58.2* | 86.5* |
| | vP921 | 7.8 | 55.2* | 81.0* |

BALB/cJ spleen cells from mice immunized approximately 1 month earlier with the indicated vaccinia virus recombinants and were incubated with infected syngeneic spleen cells for 5 days and assayed for cytotoxicity at an effector to target cell ratio of 20.1.
* P < 0.05 compared to controls, Student's t-test.

TABLE 3

Anamnestic CTL responses of the spleen cells of mice administered a single inoculation of recombinant vaccinia or canarypox virus expressing the V3 loop of HIV gp120.

| IMMUNIZATION | | PERCENT CYTOTOXICITY | | | |
|---|---|---|---|---|---|
| PRIMARY | BOOSTER | TARGET | | | |
| in vivo | in vitro | P815 | Vac | CP | HIV V3 |
| NONE | NONE | 0.4 | −2.5 | −2.3 | −1.5 |
| | vP804 | 0.5 | 8.8 | 0.7 | 0.8 |
| | vP878 | 1.8 | 6.1 | 0.4 | 1.6 |
| | CP | 5.8 | 4.2 | 4.9 | 0.4 |
| | VCP95 | 4.4 | 2.6 | 6.1 | 0.1 |
| | SB13S | −0.2 | −0.7 | −0.4 | 0.5 |
| vP804 | NONE | 0.7 | 1.7 | 0.1 | 1.3 |
| | vP804 | 5.5 | 43.5* | 5.8 | 3.5 |
| | vP878 | 3.6 | 42.5* | 1.6 | −0.3 |
| | CP | 8.5 | 7.0 | 5.6 | 3.9 |
| | vCP95 | 5.8 | 5.3 | 4.4 | 4.0 |
| | SB135 | 1.2 | −0.9 | −0.5 | −0.2 |
| vP878 | NONE | 0.2 | −2.9 | −0.8 | −0.2 |
| | vP804 | 5.3 | 56.4* | 7.5 | 4.1 |
| | vP878 | 6.7 | 60.2* | 7.7 | 41.7* |
| | CP | 8.7 | 13.4 | 9.4 | 4.7 |
| | vCP95 | 7.1 | 10.5 | 8.7 | 19.0 |
| | SB135 | 1.9 | −0.7 | −0.2 | −1.4 |
| cP | NONE | 4.6 | −0.6 | 2.3 | −0.0 |
| | vP804 | 11.0 | 17.7* | 5.7 | 6.1 |
| | vP878 | 7.1 | 14.6* | 12.3 | 5.5 |
| | CP | 7.4 | 5.9 | 19.3* | 3.1 |
| | vCP95 | 6.8 | 5.4 | 20.4* | 2.8 |

TABLE 3-continued

Anamnestic CTL responses of the spleen cells of mice administered a single inoculation of recombinant vaccinia or canarypox virus expressing the V3 loop of HIV gp120.

| IMMUNIZATION | | PERCENT CYTOTOXICITY | | | |
|---|---|---|---|---|---|
| PRIMARY | BOOSTER | TARGET | | | |
| in vivo | in vitro | P815 | Vac | CP | HIV V3 |
| | SB135 | 1.4 | −0.4 | 0.8 | −1.4 |
| vCP95 | NONE | −0.8 | −2.2 | −1.3 | 0.3 |
| | vP804 | 9.4 | 26.4* | 9.3 | 6.6 |
| | vP878 | 10.4 | 22.5* | 16.9 | 32.1* |
| | CP | 8.8 | 7.2 | 20.0* | 3.2 |
| | VCP95 | 5.1 | 4.2 | 19.6* | 7.8 |
| | SB135 | 1.9 | −1.5 | −0.3 | −1.2 |

Twenty-three days after immunization, the spleen cells were stimulated in vitro for 5 days with virus infected or peptide-pulsed syngeneic spleen cells and then assayed for specific cytotoxicity against virus infected or peptide-pulsed P815 target cells at an effector to target cell ratio of 20:1.
* $P < 0.05$ compared to appropriate controls, Student's t-test.

TABLE 4

Depletion of cytotoxic activity with monoclonal antibodies to CD8 plus complement.

| IMMUNIZATION | | | PERCENT CYTOTOXICITY TARGETS | | |
|---|---|---|---|---|---|
| in vivo | in vitro | TREATMENT | P815 | VAC | HIV V3 |
| NONE | NONE | NONE | 1.1 | 1.5 | −0.3 |
| NONE | NYVAC | NONE | −7.4 | 0.4 | −0.4 |
| NONE | vP921 | NONE | −0.2 | 1.1 | −0.7 |
| NYVAC | NONE | NONE | −3.1 | −0.3 | −1.4 |
| NYVAC | NYVAC | NONE | −2.6 | 40.5 | −0.3 |
| NYVAC | vP921 | NONE | 3.3 | 31.4 | −2.9 |
| vP921 | NONE | NONE | 3.0 | −1.3 | −0.1 |
| vP921 | NYVAC | NONE | −4.9 | 25.9 | 12.2 |
| vP921 | vP921 | NONE | −0.2 | 21.3 | 30.5 |
| vP921 | vP921 | C' | 4.6 | 20.1 | 22.9 |
| vP921 | vP921 | anti-CD4 | 4.2 | 22.6 | 23.2 |
| vP921 | vP921 | anti-CD8 | −5.0 | 22.5 | 26.9 |
| vP921 | vP921 | anti-CD4 + C' | 10.0 | 26.6 | 30.1 |
| vP921 | vP921 | anti-CD8 + C' | 9.2 | 7.1 | 2.3 |

TABLE 5

Specificity of primary CTL activity for the V3 loop of HIV-1 isolate $III_B$ following a single inoculation with HIV recombinant vaccinia viruses.

| IMMUNIZATION | | PERCENT CYTOTOXICITY TARGET | | | |
|---|---|---|---|---|---|
| | | | V3 PEPTIDE | | |
| | | P815 | IIIB | SF2 | MN |
| NONE | | −2.7 | −1.9 | −0.9 | −1.2 |
| | ± | −0.5 | 0.5 | 0.5 | 0.5 |
| NYVAC | | −1.6 | −0.3 | −0.6 | −0.3 |
| | ± | −0.5 | 0.8 | 0.7 | 0.2 |
| vP878 | | −2.8 | 0.5 | −0.5 | −1.2 |
| | ± | 0.8 | 1.0 | 0.6 | 0.5 |
| vP911 | | −2.6 | 7.5* | −0.5 | −1.1 |
| | ± | 0.2 | 3.2 | 0.5 | 0.4 |

TABLE 5-continued

Specificity of primary CTL activity for the V3 loop of HIV-1 isolate $II_B$ following a single inoculation with HIV recombinant vaccinia viruses.

| IMMUNIZATION | | PERCENT CYTOTOXICITY TARGET | | | |
|---|---|---|---|---|---|
| | | | V3 PEPTIDE | | |
| | | P815 | IIIB | SF2 | MN |
| vP921 | | −2.5 | 12.5* | −0.1 | −1.2 |
| | ± | 0.7 | 3.6 | 0.5 | 0.5 |

Mice were administered a single iv inoculation with the indicated vaccinia virus recombinant and assayed for CTL activity 7 days later against P815 targets and P815 targets pulsed with one of three peptides corresponding to the V3 loop region of HIV-1 isolates $III_B$, SF2, and MN. Although assayed at effector to target cell ratios of 100:1, 50:1, and 25:1, only the 100:1 data are shown.
* $P < 0.05$ vs appropriate controls, Student's t-test

TABLE 6

Specificity of secondary CTL activity for the V loop of HIV-1 isolate $III_B$ following a single inoculation with HIV recombinant vaccinia viruses.

| IMMUNIZATION | | PERCENT CYTOTOXICITY TARGET | | | |
|---|---|---|---|---|---|
| | | | V3 PEPTIDE | | |
| in vivo | in vitro | P815 | IIIB | SF2 | MN |
| NONE | NONE | 1.0 | 1.1 | 0.5 | −0.0 |
| | NYVAC | 0.4 | 0.5 | −0.6 | −0.3 |
| | vP878 | 0.2 | 0.2 | −0.5 | −1.0 |
| | vP911 | −1.5 | 0.3 | −0.5 | 0.2 |
| | vP921 | −0.6 | 1.4 | 0.1 | −0.5 |
| NYVAC | NONE | −2.2 | 0.2 | 0.5 | −1.0 |
| | NYVAC | 3.2 | 2.2 | 3.9 | 2.5 |
| | vP878 | 4.4 | 5.9 | 5.0 | 6.1 |
| | vP911 | 5.8 | 11.1 | 5.0 | 5.3 |
| | vP921 | 5.0 | 6.5 | 2.9 | 2.9 |
| vP878 | NONE | 0.1 | −0.2 | −0.9 | −1.0 |
| | NYVAC | 3.0 | 4.8 | 4.4 | 4.5 |
| | vP878 | 7.9 | 20.2 | 7.8 | 8.6 |
| | vP911 | 4.8 | 7.8 | 4.5 | 4.7 |
| | vP921 | 2.7 | 6.9 | 2.8 | 3.0 |
| vP911 | NONE | 0.9 | 1.8 | 1.4 | 0.5 |
| | NYVAC | 8.8 | 8.3 | 8.1 | 6.6 |
| | vP878 | 6.6 | 57.2 | 6.8 | 8.2 |
| | vP911 | 4.6 | 63.7 | 2.9 | 4.2 |
| | vP921 | 7.2 | 63.6 | 4.1 | 4.9 |
| vP921 | NONE | 0.5 | 0.8 | 1.2 | 0.6 |
| | NYVAC | 4.4 | 7.9 | 7.5 | 6.0 |
| | vP878 | 8.1 | 59.0 | 7.1 | 7.5 |
| | vP911 | 6.4 | 71.4 | 7.9 | 6.6 |
| | vP921 | 9.3 | 63.4 | 9.0 | 8.1 |

TABLE 7

Lymphocyte proliferative responses to HIV gp160 epitopes 27 days after a single immunization with HIV recombinant vaccinia viruses.

| | | | | | COUNTS PER MINTUE HIV ANTIGEN | | | | | |
|---|---|---|---|---|---|---|---|---|---|---|
| | | | gp160 (μg) | | T1 (μg) | | | T2 (μg) | | |
| IMMUNIZATION | | RPMI | 1 | 10 | 1 | 5 | 10 | 1 | 5 | 10 |
| NONE | MEAN | 5,185 | 6,397 | 7,808 | 7,682 | 8,614 | 11,541 | 6,141 | 8,835 | 6,774 |
| | ± SD | 1,020 | 2,174 | 2,596 | 1,274 | 2,033 | 2,036 | 2,103 | 1,883 | 2,806 |
| | SI | 1.0 | 1.2 | 1.5 | 1.0 | 1.1 | 1.5 | 1.0 | 1.4 | 1.1 |
| NYVAC | MEAN | 10,327 | 13,589 | 15,969 | 11,360 | 12,654 | 15,369 | 10,339 | 9,834 | 8,868 |
| | ± SD | 1,543 | 3,323 | 4,583 | 1,352 | 2,272 | 1,821 | 762 | 1,731 | 502 |
| | SI | 1.0 | 1.3 | 1.5 | 1.0 | 1.1 | 1.4 | 1.0 | 1.0 | 0.9 |
| vP878 | MEAN | 10,126 | 13,150 | 18,329 | 11,114 | 11,956 | 13,754 | 10,415 | 11,442 | 9,147 |
| | ± SD | 1,269 | 1,103 | 4,245 | 1,217 | 1,106 | 1,568 | 335 | 1,288 | 1,033 |
| | SI | 1.0 | 1.3 | 1.8 | 1.0 | 1.1 | 1.2 | 1.0 | 1.1 | 0.9 |
| vP911 | MEAN | 12,155 | 15,564 | 26,083 | 12,417 | 15,380 | 17,007 | 10,681 | 11,412 | 0,702 |
| | ± SD | 1,307 | 9,707 | 16,327 | 873 | 1,847 | 6,266 | 2,428 | 3,201 | 1,468 |
| | SI | 1.0 | 1.3 | 2.1 | 1.0 | 1.2 | 1.4 | 1.0 | 1.1 | 1.0 |
| vP921 | MEAN | 9,701 | 49,256 * | 61,036 * | 10,550 | 15,367 | 15,816 | 8,818 | 9,232 | 8,803 |
| | ± SD | 2,601 | 23,673 | 25,866 | 3,447 | 3,481 | 7,176 | 954 | 2,265 | 2,860 |
| | SI | 1.0 | 5.1 | 6.3 | 1.0 | 1.5 | 1.5 | 1.0 | 1.0 | 1.0 |

SI - stimulation index.
* $P < 0.05$ compared to unstimulated control cultures Student's t-test

TABLE 8

HIV gp160 ELISA titers of mice immunized with HIV recombinant vaccinia viruses.

| | WEEKS AFTER IMMMUNIZATION | | | | | |
|---|---|---|---|---|---|---|
| IMMUNIZATION | 0 | 1 | 2 | 4 | 7 | 9 |
| CONTROLS | 22 | 32 | 32 | 38 | 36 | 33 |
| NYVAC | 38 | 36 | 37 | 28 | 50 | 45 |
| vP878 | 20 | 43 | 27 | 46 | 65 | 63 |
| vP911 | 0 | 0 | 90 | 453 | 4,614 | 3,263 |
| vP921 | 0 | 26 | 25 | 77 | 2,614 | 1,689 |

EXAMPLE 3

EXPRESSION OF THE HIV-1 (ARV-2 OR SF-2 STRAIN) env GENE IN ALVAC, TROVAC AND NYVAC VECTORS Plasmid Constructions The lambda clone containing the entire HIV-1 (ARV-2 or SF-2 strain) genome was provided by J. Levy and was described previously (Sanchez-Pescador et al., 1985). The env sequences were subcloned into pUC13, creating plasmid pMP7MX373, which contains the sequences from -1 relative to the initiation codon (ATG) of the env gene product to 715 bp downstream of the termination codon (TAA) of the env gene. These env sequences were excised from pMP7MX373 by digestion with EcoRI and HindIII and inserted into the plasmid vector, pIBI25 (International Biotechnologies, Inc., New Haven, Conn.) generating plasmid pIBI25env.

Recombinant plasmid pIBI25env was used to transform competent E. coli CJ236 (dut- ung-) cells. Single-stranded DNA was isolated from phage derived by infection of the transformed E. coli CJ236 cells with the helper phage, MG408. This single-stranded template was used in in vitro mutagenesis reactions (Kunkel et al., 1985) with oligonucleotide MUENVT12 (SEQ ID NO:45) (5'-AGAGGGGAATTCTTCTACTGCAATACA-3'). Mutagenesis with this oligonucleotide generates a T to C transition and disrupts the T5CT motif at nucleotide positions 6929–6935 of the ARV-2 genome (Sanchez-Pescador et al., 1985). This mutation does not alter the amino acid sequence of the env gene and creates an EcoRI site, which was used to screen for mutagenized plasmid clones. Sequence confirmation was done by the dideoxynucleotide chain termination method (Sanger et al., 1977). The resultant mutagenized plasmid was designated as pIBI25mutenv11.

A 1.45 kb BglII fragment was derived from pIBI25mutenv11. This fragment contained the mutated env sequences. It was used to substitute for the corresponding unmutated fragment in pIBI25env. The resultant plasmid was designated as pIBI25mutenv8. Further modifications were made to pIBI25mutenv8. In vitro mutagenesis was performed to remove the sequence coding for the rex protein and the LTR sequence (LTR region) from the 3'-end of the gene and to delete the putative immuno-suppressive (IS) region amino acids 583 through 599 (SEQ ID NO:46:Leu-Gln-Ala-Arg-Val-Leu-Ala-Val-Glu-Arg-Tyr-Leu-Arg-Asp-Gln-Gln-Leu) (Klasse et al., 1988). These reactions were done with the single-stranded template derived from pIBI25mutenv8 with oligonucleotides LTR2 (SEQ ID NO:47) (5'-TTGGAAAGGCTTTTGGCAT-GCCACGCGTC-3') and MUENSVISR (SEQ ID NO:48) (5'-ACAGTCTGGGGCATCAAGCAGCTAGGGATTT-GGGGTTGCTCT-3'). Mutagenized clones were identified by hybridization and restriction analysis. A clone mutagenized such that it was deleted both of the IS and the LTR region and another deleted of the LTR was confirmed by nucleotide sequence analysis and designated pIBI25mut3env40 and pIBI25mut2env22, respectively.

A 3.4 kb SmaI/HindIII fragment containing the entire env gene was derived from pIBI25mut3env40 and from pIBI25mut2env22 and inserted into pCPCV1 and pFPCV2, digested with SmaI/HindIII. The plasmid pCPCV1 is an insertion plasmid which enables the generation of ALVAC recombinants with insertion occurring in the C3 locus. The plasmid, pFPCV2, is an insertion plasmid which enables the generation of TROVAC recombiants with insertion occurring in the F7 locus. Plasmids pCPCV1 and pFPCV2 have been described previously in PCT International Publication No. WO 89/03429 published Apr. 20, 1989.

Oligonucleotide PROVECNS (SEQ ID NO:49) (5'-CCGTTAAGTTTGTATCGTAATGAAAGTGAAGGGGA-CCAGG-3') was used for in vitro mutagenesis reactions via the method of Mandecki (1986) to make a precise ATG:ATG construction with the VVH6 promoter and the env sequences. Potential mutants were screened for the loss of the SmaI site. Plasmid clones devoid of a SmaI site were identified and confirmed by nucleotide sequence analysis. Properly mutagenized plasmid clones were identified and designated as pCPenvIS+ or pCPenvIS− and pFPenvIS+ or pFPenvIS−.

The HIV-1 env genes were excised from pCPenvIS− by digestion with NruI and HindIII. The two env fragments of 2.5 kb (envIS+) and 2.4 kb (envIS−), respectively, were isolated and blunt-ended by reaction with the Klenow fragment of the *E. coli* DNA polymerase in the presence of 2 mM dNTPs. These fragments were ligated with the 3.5 kb fragment derived by digestion of pSIVenvVV with NruI and PstI with a subsequent blunting step with the Klenow fragment of the *E. coli* DNA polymerase in the presence of 2 mM dNTPs. The plasmid pSIVenvVV contains the SIV env gene expression cassette regulated by the vaccinia virus H6 promoter in the ATI insertion locus. Digestion of pSIVenvVV with NruI and PstI excises the entire SIV env coding sequences and the 3'-most 20 bp of the promoter element. Ligation to the env IS− and env IS+ fragments restores the 20 bp of the H6 promoter and inserts the HIV-1 env gene into the ATI insertion plasmid. The resultant plasmids were designated as pAR5VV+ and pAR6VV− for env IS+ and env IS−, respectively.

In Vitro Recombination and Purification of Recombinants

Recombination was performed introducing plasmid DNA into infected cells by calcium phosphate precipitation both for ALVAC and for TROVAC recombinants, as previously described (Piccini et al., 1987). Plasmids pCPenvIS+ and pCPenvIS− were used to make recombinants vCP61 and vCP60, respectively. Plasmids pFPenvIS+ and pFPenvIS− for recombinants vFP63 and vFP62, respectively. The plasmids pAR5VV+ and pAR6VV− were used in in vitro recombination experiments with vP866 as rescue to yield vP939 and vP940, respectively. Recombinant plaques were selected by autoradiography after hybridization with a $^{32}$p-labeled env specific probe and passaged serially three times to assure purity, as previously described (Piccini et al., 1987).

Expression of the HIV-1 env Gene

Six different recombinant viruses were prepared where the HIV env gene of the ARV-2 or SF-2 strain was inserted downstream from a vaccinia early-late promoter, H6. For simplicity, the two ALVAC-based recombinant viruses, vCP61 and vCP60, will be referred to as CPIS+ and CPIS−, the two TROVAC− based recombinants, vFP63 and vFP62, as FPIS+ and FPIS−, and the two NYVAC-based recombinants, vP939 and vP940, as VV− and VV+, respectively.

All the constructs were precise, in that, the ATG initiation codon of the HIV-1 env gene was superimposed on the ATG of the vaccinia H6 promoter. Moreover, all extraneous genetic information 3' to the termination codon was eliminated. CPIS−, FPIS−, and VV− were all obtained by deletion of a 51 bp region, corresponding to amino acids 583–599, located near the 5' portion of the gp41 gene product. This region shares homology with putative immunosuppressive regions (Klasse et al., 1988; Ruegg et al., 1989a,b) occurring in the transmembrane polypeptide of other retrovirus glycoproteins (Cianciolo et al., 1985; Ruegg et al., 1989a,b).

Expression analyses with all six recombinant viruses were performed in CEF, Vero, and MRC-5 cell monolayers. radioimmunoprecipitation experiments using pooled sera from HIV seropositive individuals were performed as described above. All six recombinants directed the synthesis of the HIV-1 gp160 envelope precursor. The efficiency of processing of gp160 to gp120 and gp41, however, varied between cell types and was also affected by deletion of the immunosuppressive region. Recognition of gp41 by the pooled sera from HIV seropositive individuals also varied between the virus background and the cell type.

EXAMPLE 4

EXPRESSION OF THE HIV-2 (ISSY STRAIN) env GENE IN NYVAC

Expression of gp160

Oligonucleotides HIV25PA (SEQ ID NO:50) (5'-ATGAGTGGTAAAATTCAGCTGCTTGTTGCCTTTCT-GCTAACTAGTGCTTGCTTA-3') and HIV25PB (SEQ ID NO:51) (5'-TAAGCAAGCACTAGTTAGCAGAAAGGC-AACAAGCAGCTGAATTTTACCACTCAT-3') were annealed to constitute the initial 54 bp of the HIV-2 ISSY strain (Franchini et al., 1989) env coding sequence. This fragment was fused 3' to a 129 bp fragment derived by PCR with oligonucleotides H65PH (SEQ ID NO:52) (5'-ATCATCAAGCTTGATTCTTTATTCTATAC-3') and H63PHIV2 (SEQ ID NO:53) (5'-CAGCTGAATTTTACCACTCATTACGATACAAACTT-AACG-3') using pTP15 (Guo et al., 1989) as template. The fusion of these two fragments was done by PCR using oligonucleotides HIV25PC (SEQ ID NO:54) (5'-TAAGCAAGCACTAGTTAG-3') and H65PH (SEQ ID NO:52). The 174 bp PCR derived fragment was digested with HindIII and SacI and inserted into pBS-Sk (Stratagene, La Jolla, Calif.) digested with HindIII and SacI. The resultant fragment was designated pBSH6HIV2. The insert was confirmed by nucleotide sequence analysis.

The 3' portion of the HIV-2 env gene was also derived by PCR. In this reaction a 270 bp fragment was amplified with oligonucleotides HIV2B1 (SEQ ID NO:55) (5'-CCGCCTCTTGACCAGAC-3') and HIV2B2 (SEQ ID NO:56) (5'-ATCATCTCTAGAATAAAAATTACAGGA-GGGCAATTTCTG-3') using pISSY-KPN (provided by Dr. Genoveffa Franchini, NCI-NIH, Bethesda, Md.) as template. This fragment fragment was digested with BamHI and XbaI. The 150 bp fragment derived from this digestion contained a 5' BamHI and a 3' XbaI cohesive end. The fragment was engineered to contain a T5NT sequence motif known to be recognized as vaccinia virus early transcription termination signal (Yuen et al., 1987), following the termination codon (TAA).

The majority of the HIV-2 env gene was obtained from pISSY-KPN by digestion with SacI and BamI. The 2.7 kb fragment generated by this digestion was coinserted into pBS-SK digested with SacI and XbaI with the 150 bp BamHI/XbaI fragment corresponding to the 3' end of the gene. The resultant plasmid was designated pBSHIV2ENV.

The 174 bp SpeI/HindIII fragment from pBSH6HIV2 and the 2.5 kb SpeI/XbaI fragment from pBSHIV2ENV were ligated into pBS-SK digested with HindIII and XbaI to yield pBSH6HIV2ENV. The 2.7 kb HindIII/XbaI insert from pBSH6HIV2ENV was isolated and blunt-ended with the Klenow fragment of the *E. coli* DNA polymerase in the presence of 2 mM dNTP. The blunt-ended fragment was inserted into a SmaI digested pSD541VC insertion vector. The resultant plasmid was designated as pATIHIV2ENV. This plasmid was used in vitro recombination experiments with vP866 (NYVAC) as the rescuing virus to yield vP920.

Immunoprecipitation analysis was performed to determine whether vP920 expresses authentic HIV-2 gp160.

Lysates from the infected cells were analyzed for HIV-2 env gene expression using pooled serum from HIV-2 seropositive individuals (obtained from Dr. Genoveffa Franchini, NCI-NIH, Bethesda, Md.). The sera was preadsorbed with vP866 infected Vero cells. The preadsorbed human sera was bound to Protein A-sepharose in an overnight incubation at 4° C. Following this incubation period, the material was washed 4×with 1×buffer A. Lysates precleared with normal human sera and protein A-sepharose were then incubated overnight at 4° C. with the human sera from seropositive individuals bound to protein A-sepharose. After the overnight incubation period, the samples were washed 4×with 1×buffer A and 2×with a LiCl$_2$/urea buffer. Precipitated proteins were dissociated from the immune complexes by the addition of 2×Laemmli's buffer (125 mM Tris(pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV-2 seropositive individuals specifically precipitated the HIV-2 gp160 envelope glycoprotein from vP920 infected cells. Furthermore, the authenticity of the expressed HIV-2 env gene product was confirmed, since the gp160 polyprotein is processed to the mature gp120 and gp41 protein species. No HIV-specific protein species were precipitated from mock-infected cells or cells infected with the parental virus, vP866. Also, supportive of the proper expression of the HIV-2 env by vP920 was the observation by an immunofluorescence assay that the gene product is expressed on the surface of vP920 infected cells.

Expression of gp120

The plasmid pBSH6HIV2 containing the vaccinia virus H6 promoter fused to the 5'-end of the HIV-2 env gene was digested with SpeI and HindIII to liberate the 180 bp fragment containing these sequences. This fragment was ligated into pBS-SK digested with HindIII and XbaI along with the 1.4 kb SpeI/XbaI fragment of pBSHIV2120A to yield pBSHIV2120B.

The plasmid pBSHIV2120A was derived by initially deriving the 3' portion of the gp120 coding sequence by PCR. The PCR was performed using oligonucleotides HIV2120A (SEQ ID NO:57) (5'-ATCATCTCTAGAATAAAAATTATCTCTTATGTCT-CCCTGG-3') and HIV2120B (SEQ ID NO:58) (5'-AATTAACTTTACAGCACC-3') with pISSY-KPN as template. The PCR-derived fragment was digested with EcoRI and XbaI to yield a 300 bp fragment which contained a 5'-EcoRI cohesive end and a 3'-XbaI cohesive end. The fragment was engineered with a translation termination sequence (TAA) and a T5NT sequence motif just 5' to the XbaI site. The 300 bp XbaI/EcoRI PCR fragment was ligated into pBS-SK digested with SacI/XbaI along with a 1.4 kb SacI/EcoRI fragment derived from pISSY-KPN to generate pBSHIV2120A.

The plasmid pBSHIV2120B was digested with HindIII and XbaI to generate a 1.8 kb fragment containing the HIV-2 gp120 coding sequence juxtaposed 3' to the vaccinia virus H6 promoter. This fragment was blunted with the Klenow fragment of the E. coli DNA polymerase in the presence of 2 mM dNTPs. The blunt-ended fragment was ligated to SmaI digested pSD541VC to generate pATIHIV2120. This plasmid was used in in vitro recombination experiments to yield vP922.

Immunoprecipitation experiments with vP922 infected cells were performed as described above for the expression of the entire HIV-2 env gene. No HIV-specific species were precipitated from mock infected or vP866 infected Vero cells. A protein species of 120 kDa was, however, precipitated from lysates derived from cells infected with vP922.

EXAMPLE 5

EXPRESSION OF SIV GENES IN NYVAC

Generation of NYVAC/SIV gp140 Recombinant

A plasmid pSS11E containing the SIV $(_{mac142})$ env gene was obtained from Dr. Genoveffa Franchini (NCI-NIH, Bethesda, Md.). This plasmid was digested with HindIII and PstI to liberate a 2.2 kbp fragment containing from nucleotide 220 of the SIV env gene to a region 160 bp downstream from the translation termination codon. It should be noted that an expression cassette containing this fragment will result in the expression of a gp140 protein species rather that a gp160 species. This 40% deletion of the transmembrane region results from a premature termination at nucleotide 7,934 of the genome (Franchini et al., 1987). Such premature terminations of the env gene product are noted after propagation of SIV in culture (Kodama et al., 1989).

The amino portion of the gene was derived by PCR using pSS11E as template and oligonucleotides SIVENV1 (SEQ ID NO:59) (5'-CGATATCCGTTAAGTTTGTATCGTAA-TGGGATGTCTTGGGAATC-3') and SIVENV2 (SEQ ID NO:60) (5'-CAAGGCTTTATTGAGGTCTC-3'). The resultant 250 bp fragment contains the 5'-most 230 bp of the SIV env gene juxtaposed downstream from the 3'-most 20 bp of the vaccinia virus H6 promoter (3'-end of NruI site). A 170 bp fragment was obtained by digestion of the fragment with HindIII, which removes 80 bp of SIV env sequences.

The sequences containing the remainder of the SIV env gene following the premature termination signal were derived by PCR from pSS35E (obtained from Dr. Genoveffa Franchini). This plasmid contains sequences containing the C-terminal portion of the SIV env gene into the LTR region downstream from the env gene. The oligonucleotides used to derive the 360 bp fragment were SIVENV3 (SEQ ID NO:61) (5'-CCTGGCCTTGGCAGATAG-3') and SIVENV4A (SEQ ID NO:62) (5'-ATCATCGAATTCAAAAATATTACAAAGAGCGTGA-GCTCAAGTCCTTGCCTAATCCTCC-3'). This fragment was digested with PstI and EcoRI to generate a 260 bp fragment having a 5' PstI cohesive end and a 3'- EcoRI cohesive end.

The 2.2 kb HindIII/PstI fragment from pSS11E, the 170 bp NruI/HindIII fragment containing the 5' end of the gene, and the 260 bp PstI/EcoRI containing the 3' end of the gene were ligated with a 3.1 kb NruI/EcoRI fragment derived from pRW838. pRW838 contains the vaccinia virus H6 promoter linked to the rabies G gene flanked by canarypoxvirus sequences which enable the insertion of genes into the C5 locus. Digestion with NruI and EcoRI liberates the rabies G gene and removes the 3'-most 20 bp of the H6 promoter. The resultant C5 insertion plasmid containing the SIV env gene linked to the vaccinia H6 promoter was designated as pC5SIVENV.

The plasmid, pC5SIVENV, was digested with HindIII and EcoRI to liberate a 2.2 kb fragment, containing from nucleotide 150 of the SIV env gene to the end of the entire gene. PCR was used to derive the vaccinia H6 promoter/SIV env linkage from pC5SIVENV with oligonucleotides MPSYN286 (SEQ ID NO:63) (5'-CCCCCCAAGCTTTTTTATTCTATACTT-3') and SIVENV2 (SEQ ID NO:64) (5'-CAAGGCTTTATTGAGGTCTC-3'). The 320 bp fragment was digested with HindIII to derive a 240 bp fragment. The 2.2 kb HindIII/EcoRI and the 240 bp HindIII fragment were coligated into pC3I digested with HindIII and EcoRI. The resultant plasmid containing the HindIII fragment in the proper orientation relative to the SIV env coding sequence was designated pC3SIVEM. The plasmid pC3I was derived as follows. The nucleotide sequence analysis of an 2.5 kb BglII canarypoxvirus genomic fragment revealed the entire C3 open reading frame and the 5' and 3' flanking regions. In order to construct a donor plasmid for insertion of foreign genes into the C3 locus with the complete excision of the C3 open reading frame. PCR primers were used to amplify the 5' and 3' sequences relative to C3. Primers for the 5' sequences were RG277 (SEQ ID NO:65) (5'-CAGTTGGTACCACTGGTATTTTATTTCAG-3') and RG278 (SEQ ID NO:66) (5'-TATCTGAATTCCTGCAGCCCGGGTTTTTATAGCTAATTAGTCAAATGTGAGTTAATATTAG-3').

Primers for the 3' sequences were RG279 (SEQ ID NO:67) (5'-TCGCTGAATTCGATATCAAGCTTATCGATTTTTATGACTAGTTAATCAAATAAAAAGCATACAAGC-3') and RG280 (SEQ ID NO:68) (5'-TTATCGAGCTCTGTAACATCAGTATCTAAC-3'). The primers were designed to include a multiple cloning site flanked by vaccinia transcriptional and translational termination signals. Also included at the 5'-end and 3'-end of the left arm and right arm were appropriate restriction sites (Asp718 and EcoRI for left arm and EcoRI and SacI for right arm) which enabled the two arms to ligate into Asp718/SacI digested pBS-SK plasmid vector. The resultant plasmid was designated as pC3I.

The plasmid pC3SIVEM was linearized by digestion with EcoRI. Subsequent partial digestion with HindIII liberated a 2.7 kb HindIII/EcoRI fragment. This fragment was blunt-ended by treatment with Klenow fragment of the *E. coli* DNA polymerase in the presence of 2 mM dNTPs. The fragment was ligated into pSD550VC digested with SmaI. The resultant plasmid was designated as pSIVEMVC. This plasmid was used in in vitro recombination experiments with vP866 as rescue virus to generate vP873. vP873 contains the SIV env gene in the I4L locus.

Generation of a NYVAC/gag/pol and gag Recombinants

A plasmid, pSIVAGSS11G, containing the SIV cDNA sequence encompassing the gag and pol genes was obtained from Dr. Genoveffa Franchini (NCI-NIH, Bethesda, Md.). The gag and pol genes from this plasmid were juxtaposed 3' to the vaccinia I3L promoter between vaccinia tk flanking arms. This was accomplished by cloning the 4,800 bp CfoI/TagI fragment of pSIVGAGSS11G, containing the gag and the oligonucleotides SIVL1 (SEQ ID NO:69) (5'-TCGAGTGAGATAAAGTGAAAATATATATCATTATATTACAAGTACAATTATTTAGGTTTAATCATGGGCG-3') and SIVL2 (SEQ ID NO:70) (5'-CCCATGATTAAACCTAAATAATTGTACTTTGTAATATAATGCTATATATTTTCACTTTATCT- CAC -3') corresponding to the I3L promoter into the 4,070 bp XhoI/AccI fragment of pSD542, a derivative of pSD460 (FIG. 1). The plasmid generated by this manipulation was designated pSIVG1.

To eliminate the pol gene, a 215 bp PCR fragment was derived from pSIVGAGSS11G using oligonucleotides SIVP5 (SEQ ID NO:71) (5'-AATCAGAGAGCAGGCT-3') and SIVP6 (SEQ ID NO:72) (5'-TTGGATCCCTATGCCACCTCTCT-3'). The PCR-derived fragment was digested with BamHI and StuI and ligated with the 5,370 bp partial BamHI/StuI fragment of SIVG1. This resulted in the generation of pSIVG2. pSIVG2 was used in in vitro recombination experiments with vP873 as rescue virus to yield vP948.

The plasmid to insert both gag and pol into NYVAC-based vectors was engineered in the following manner. pSIVG1, described above, contains extraneous 3'-noncoding sequences which were eliminated using a 1 kb PCR fragment. This fragment was generated from plasmid pSIVGAGSS11G with the oligonucleotides SIVP5 and SIVP6. This PCR derived fragment containing the 3' end of the pol gene was digested with BamHI and HpaI. The 1 kb BamHI/HpaI fragment was ligated to the 7,400 bp partial BamHI/HpaI fragment of pSIVG1 to yield pSIVG4.

Sequence analysis of pSIVG4 revealed a single base pair deletion within the pol gene. To correct this error the 2,300 bp BglII/StuI fragment from pSIVG1 was inserted into the 6,100 bp partial BglII/StuI fragment of pSIVG4 to yield pSIVG5. The plasmid, pSIVG5, was used in in vitro recombination experiments with vP873 as rescue to generate vP943.

Generation of NYVAC/SIV p16 and p28 Recombinants

The pol gene and the portion of the gag gene encoding p28, p2, p8, p1, and p6 were eliminated from pSIVG1. This was accomplished by cloning the oligonucleotides SIVL10 (SEQ ID NO:73) (5'-AGACCAACAGCACCATCTAGCGGCAGAGGAGGAAATTACTAATTTTTATTCTAGAG-3') and SIVL11 (SEQ ID NO:74) (5'-GATCCTCTAGAATAAAAATTAGTAATTTCCTCCTCTGCCGCTAGATGGTGCTGTTGGT-3') into the 4,430 bp AccI/BamHI fragment of pSIVG1 to generate pSIVG3. This plasmid contains an expression cassette for the SIV p16 gene product expressed by the vaccinia I3L promoter.

The entomopoxvirus 42 kDa-promoted SIV p28 gene (5' end only) was inserted downstream from the I3L-promoted p16 gene. This was accomplished by cloning the 360 bp BspMI/BamHI fragment of pSIVG1, containing the 5' end of the p28 gene, the oligonucleotides pSIVL14 (SEQ ID NO:75) (5'-TAGACAAAATT GAAAATATATAATTACAATATAAAATGCCAGTACAACAAATAGGTGGTAACTATGTCCACCTGCC ATT-3') and SIVL15 (SEQ ID NO:76) (5'-GCTTAATGGCAGGTGGACATAGTTACCACCTATTTGTTGTACTGGCATTTTATATTGTAATTATATATTTTCAATTTTGT-3'), containing the entomopox 42 kDa promoter into the 4,470 bp partial XbaI/BamHI fragment of pSIVG3. The resultant plasmid was designated as pSIVG6.

The 3' portion of the p28 gene was then inserted into pSIVG6. A 290 bp PCR fragment, containing the 3' end of the SIV p28 gene, was derived from pSIVGI using oligonucleotides SIVP12 (SEQ ID NO:77) (5'-TGGATGTACAGACAAC-3') and SIVP13 (SEQ ID NO:78) (5'-AAGGATCCGAATTCTTACATTAATCTAGCCTTC-3'). This fragment was digested with BamHI and ligated to the 4,830 bp BamHI fragment of pSIVG6. The resultant plasmid, pSIVG7, was used in in vitro recombination experiments with vP866 and vP873 as rescue experiments to generate vP942 and vP952, respectively.

Expression Analyses

The SIV gp140 env gene product is a typical glycoprotein associated with the plasma membrane of infected cells. It is expressed as a polyprotein of 140 kDa that is proteolytically cleaved to an extracellular species of 112 kDa and a transmembrane region of 28 kDa (Franchini et al., 1987). Immunofluorescence analysis using sera from rhesus macaques seropositive for SIV followed by fluorescein conjugated rabbit anti-monkey IgG demonstrated expression of the env gene product on the surface of recombinant infected Vero cells. Surface expression was not detectable on the surface of mock infected cells or cells infected with the NYVAC (vP866) parent virus. Furthermore, cells infected with recombinants containing only gag genes were not shown to express any SIV components on the surface. Surface expression in cells infected with vP873, vP943, vP948 and vP952 all demonstrated surface expression and significantly, all contain the SIV env gene.

Figure 10:
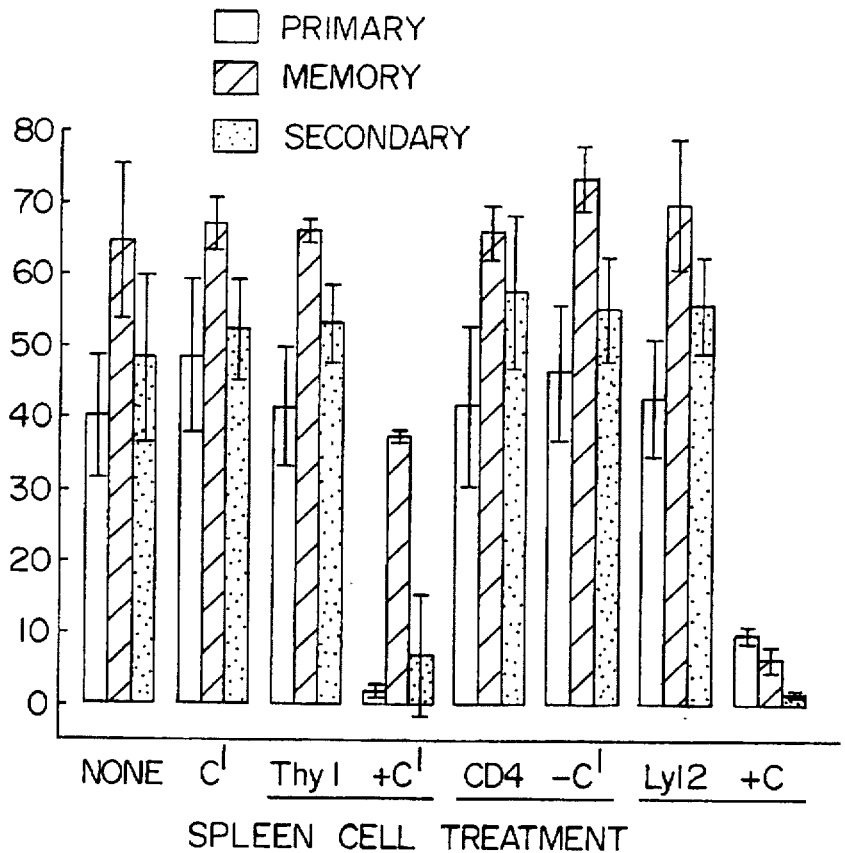
FIG. 10 shows the sensitivity of the cytotoxic effector cells from the spleens of mice immunized with vCP112 to antibodies against cytotoxic T lymphocyte cell surface antigens Thy 1.2 and Lyt 2.2.

The authenticity of the expressed SIV gene products (env and gag) in Vero cells infected with the NYVAC/HIV recombinants was analyzed by immunoprecipitation as described above, except all samples were harvested at 17 hours post infection by the addition of 1 ml of 3×Buffer A. Lysates from the infected cells were analyzed with pooled sera from SIV seropositive rhesus macaques or a monoclonal antibody specific for gag p24 gene product (both obtained from Dr. Genoveffa Franchini, NCI-NIH, Bethesda Md.).

Immunoprecipitation with the SIV seropositive macaques sera was performed in the following manner. The macaque sera was incubated with a protein A-sepharose at 4° C. for 16 hours. After washing with buffer A, the sera bound to protein A sepharose was added to lysates precleared with normal monkey sera and protein A sepharose. Following an overnight incubation at 4° C. the precipitates were washed 4×with buffer A and 2×with LiCl/urea buffer. To dissociate the precipitated protein from the antibody, the samples were boiled in 80 μl 2×Laemmli buffer for 5 minutes. The samples were fractionated on a 12.5% gel using the Dreyfuss gel system (Dreyfuss et al., 1984). The gel was fixed and treated with 1M Na-salicylate for fluorography. All the recombinants containing SIV genes were expressing the pertinent gene products. The NYVAC recombinants vP873, vP943, vP948 and vP952 which contain the SIV env gene all expressed the authentic gp140. However, it is difficult to assess the processing of the gp140 protein to the 112 kDa and 28 kDa mature forms. No species with an apparent molecular weight of 140 kDa was precipitated by macaque anti-SIV sera from mock infected Vero cells, vP866 infected Vero cells and Vero cells infected with NYVAC/SIV recombinants not containing the SIV env gene. Expression of the SIV gag encoded gene products by vP942, vP943, vP948, and vP952 was demonstrated using the pooled sera from macaques infected with SIV and the monoclonal antibody specific to the p28 gag component. Expression of the entire p55 gag protein without the pol region, which contains the protease function, by NYVAC (vP948) in Vero cells is evident. These results demonstrate that lack of SIV protease expression prevents the complete proteolysis of p55 into its mature form. This is demonstrated much more clearly when a monoclonal antibody specific to p28 was used to precipitate gag specific gene products from vP948 infected Vero cells. Contrary to this result, expression of SIV gag with the pol gene (includes protease in vP943 infected Vero cells) enabled the expressed p55 gag precursor polypeptide to be proteolytically cleaved to its mature forms.

Expression of both the p16 and p28 SIV gene products in vP942 and vP952 infected Vero cells was demonstrated using the pooled sera from macaques infected with SIV. Using the monoclonal antibody specific to p24 obviously only recognized the p28 expressed component.

Certain Materials and Methods Which Relate to Examples 6 to 8.

Assay for Cytotoxic T Lymphocytes and In Vitro Stimulation of Memory Precursors of Cytotoxic T Lymphocytes. Six week old female BALB/c mice were inoculated intravenously with $5\times10^7$ pfu of vaccinia virus (NYVAC), recombinant vaccinia virus expressing HIV-1 (IIIB) env (vP911), canarypoxvirus (ALVAC), or with recombinant canarypoxvirus expressing HIV-1 (IIIB) env (vCP112). Seven days later, the spleen cells were assayed for primary CTL activity against unmodified P815 cells or P815 cells that had been incubated overnight with a peptide corresponding to the hypervariable V3 loop region of HIV-1 (IIIB) gp120. Twenty-two days after the initial immunization, the spleen cells of the experimental mice were incubated with poxvirus infected stimulator spleen cells and assayed for memory CTL activity against peptide pulsed targets as before. To determine secondary CTL activity, 29 days after the primary immunization mice received a second inoculation of identical dosage and content as the first. Five days later, the spleen cells were assayed for cytolytic activity against peptide pulsed targets. For cytotoxicity assays, H-$2^d$ P815 murine mastocytoma cells were incubated overnight in medium (Minimum Essential Medium containing Earle's salts and supplemented with 10% fetal bovine serum, 2 mM L-glutamine, 100 U/ml penicillin, and 100 μg/ml streptomycin) with or without 20 μg/ml V3 peptide (CNTRKRIRIQRGPGRAFVTGK, American Bio-Technologies, Inc.) (SEQ ID NO:79). The following morning, the P815 cells were washed by centrifugation and labeled for 1 hr at 37° C. in 100 μCi of $Na_2{}^{51}CrO_4$ per $2\times10^6$ cells. Intact spleens were aseptically removed from euthanized mice, bathed in ice cold Hank's Balanced Salt Solution, and disrupted into single cell suspensions using a Stomacher blender. The spleen cell suspensions were washed several times by low speed centrifugation and resuspended in Assay Medium (RPMI 1640 containing 10% fetal bovine serum, 20 mM HEPES, 2 mM L-glutamine, $5\times10^{-5}$M 2-mercaptoethanol, 100 U/ml penicillin, and 100 μg/ml streptomycin). For memory CTL activity, the spleen cells from immunized mice were resuspended in Stimulation Medium (Minimum Essential Medium with Earle's salts containing 10% fetal bovine serum, 2 mM L-glutamine, $10^{-4}$M 2-mercaptoethanol, 100 U/ml penicillin, and 100 μg/ml streptomycin) and stimulated in vitro in upright 25 $cm^2$ tissue culture flasks with naive syngeneic stimulator spleen cells that had been infected with one of the poxviruses or poxvirus recombinants. After five days at 37° C., the cells were washed, counted, and resuspended in Assay Medium. $^{51}$Chromium labelled target cells were added to titrated effector cells in 96-well microtiter plates for a 4 hr $^{51}Cr$ release assay. Effector to target cell ratios (E:T) shown for the three assays were 100:1 (primary), 20:1 (memory), and 50:1 (secondary). Percent cytotoxicity was calculated as described above, i.e., (experimental $^{51}Cr$ release−spontaneous $^{51}Cr$ release)/(maximum $^{51}Cr$ release−spontaneous $^{51}Cr$ release)×100. Maximum release was determined by the addition of 5% sodium dodecyl sulfate to target cells while spontaneous release was determined by incubating target cells in the absence of effector cells. In none of the experiments presented did spontaneous release of $^{51}Cr$ from target cells exceed 20% of maximum $^{51}Cr$ release. Error bars in FIG. 7 represent 1 standard deviation from the mean. $P<0.05$, Student's t-test compared to appropriate vaccinia or canarypoxvirus immunized mice.

Cell Surface Phenotype of Cytotoxic Effector Cells. Mice spleen cells were immunized with vaccinia virus or canarypox virus vectors (NYVAC, ALVAC) or with vaccinia virus or canarypox virus recombinants expressing HIV IIIB env (vP911, vCP112). A second inoculation was administered 30 days after the first. Prior to addition to V3 peptide pulsed targets, the spleen cells were treated with monoclonal antibodies or alloantiserum to murine T-lymphocyte surface antigens in a two-stage protocol. Briefly, the spleen cells were resuspended at $10^7$ viable cells per ml of Cytotoxicity Medium (RPMI 1640 containing 0.2% BSA and 5 mM HEPES) to which was added alloanti-Thy 1.2 (Cedarlane), monoclonal anti-CD4 (172.4, K. J. Weinhold, Duke University Medical Center), or monoclonal anti-Lyt 2.2 (Cedarlane). After 30 min at 5° C., the cells were washed and resuspended in the original volume of Cytotoxicity Medium, divided into two equal portions with or without complement (Rabbit Lo-Tox M, Cedarlane) and incubated at 37° C. for 45 min. The cells were then washed in Assay Medium and, based on the pre-treatment cell densities, resuspended in volumes of Assay Medium approximating effector to target cell ratios of 100:1 (primary), 10:1 (memory), or 80:1 (secondary) before addition to a 5 hr $^{51}$Cr release assay. Error bars in FIG. 10 represent 1 standard deviation from the means.

Specificity of CTL Antigen Receptor Recognition of the V3 Loop Region of HIV IIIB gp120. Cytotoxic T lymphocytes and memory precursors of cytotoxic T lymphocytes were generated by inoculation of mice with vCP112 as described above. Assays for cytotoxic T lymphocytes were performed as described above except that P815 target cells were pulsed overnight with V3 peptide from HIV-1 IIIB (CN TRKRIRIORGPGRAFVTGK) (SEQ ID NO:79), MN (CN KRKRIHIGPGRAFYTTKN) (SEQ ID NO:80), or SF2 (CN TRKSIYIGPGRAFHTTGR) (SEQ ID NO:81). Effector to target cell ratios were 100:1 (primary), 20:1 (memory), and 50:1 (secondary).

Antibody Responses to HIV-1 (IIIB) gp120. The wells of ELISA plates (Immulon II) were coated overnight at 4° C. with 0.5 µg of partially purified HIV-1 (IIIB) gp120 (Dr. G. Franchini, NCI-NIH, Bethesda, Md.) in carbonate buffer, pH 9.6. The plates were then washed with phosphate-buffered saline containing 0.05% Tween 20 (PBST). The plates were then blocked for 2 hr at 37° C. with PBST containing 1% bovine serum albumin (BSA). After washing with PBST, sera were initially diluted 1:20 with PBST containing 0.1% BSA (dilution buffer). The sera were further 2-fold serially diluted in the wells of the ELISA plate. The plates were incubated at 37° C. for 2 hr and washed with PBST. Horseradish peroxidase conjugated rabbit anti-mouse immunoglobulins (DAKO) was diluted 1:2000 in dilution buffer and added to the wells of the ELISA plated and incubated at 37° C. for 1 hour. After washing with PBST, OPD (o-phenylenediamine dihydrochloride) in substrate buffer was added and the color was allowed to develop at ambient temperature for about 20 min. The reaction was extinguished by the addition of 2.5M $H_2SO_4$. The absorbance at 490 nm was determined on a Bio-Tek EL-309 ELISA reader. The serum endpoint was defined as the reciprocal of the dilution giving an absorbance value of 0.4.

EXAMPLE 6

Figure 7:
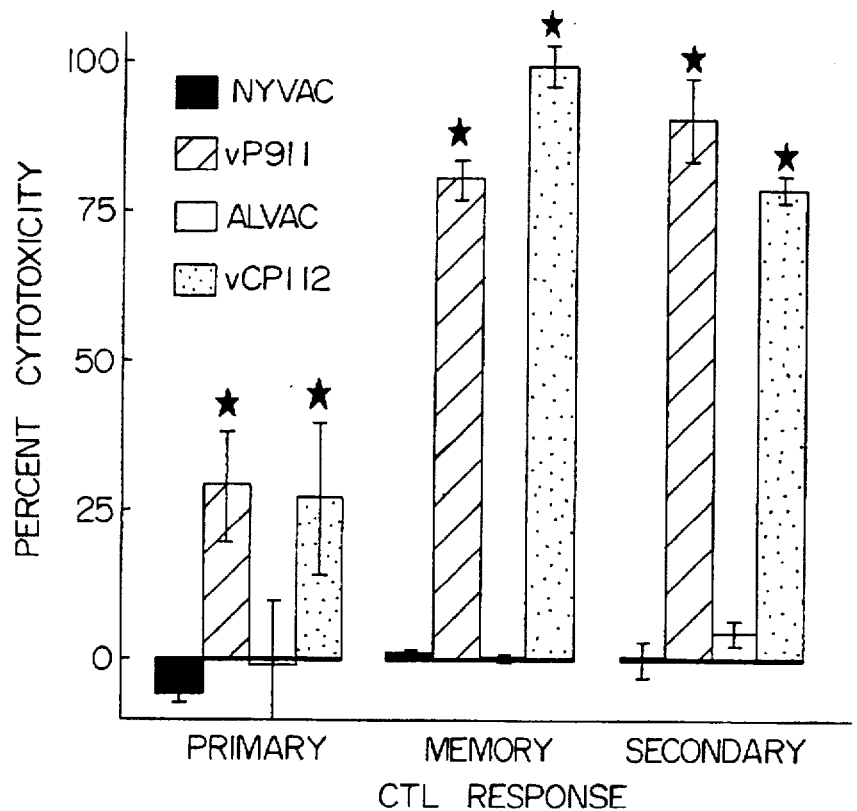
FIG. 7 shows the cytotoxic response of spleen cells of mice and immunized with vaccinia virus or canarypox virus vectors (NYVAC, ALVAC) or with vaccinia virus or canarypox virus recombinants expressing HIV III B env (vP911, vCP112)

A RECOMBINANT CANARYPOXVIRUS EXPRESSING HIV env ELICITS HIV-SPECIFIC CYTOTOXIC T LYMPHOCYTE ACTIVITY Seven days after the initial inoculation with the HIV canarypoxvirus recombinant (vCP112; defined in Example 2), cytotoxic responses of spleen cells against HIV V3 peptide pulsed target cells were roughly equivalent to the cytotoxic responses elicited by the same dose, $5 \times 10^7$ pfu, of the NYVAC recombinant, vP911 (Example 2) expressing the same HIV env gene (FIG. 7). Following appropriate in vitro stimulation or a second inoculation, the levels of cytotoxicity of the spleen cells of mice given the canarypoxvirus recombinant increased and were comparable to spleen cells from mice similarly administered the NYVAC recombinant. No such cytotoxic responses were detected from spleen cells of mice inoculated with the non-recombinant NYVAC or ALVAC vectors confirming the requirement for immunization with a poxvirus recombinant expressing the HIV env gene. Furthermore, no cytotoxic reactivity was detected against unmodified P815 cells from the spleen cells of any of the mice regardless of the inoculation regimen. Thus, only mice inoculated with recombinant NYVAC or, more significantly, recombinant ALVAC expressing the env coding sequence from HIV-1 demonstrated V3-specific cytotoxic responses.

EXAMPLE 7

CHARACTERIZATION OF CYTOTOXIC EFFECTOR CELLS

To determine the identity of the spleen cells associated with the lysis of HIV-1 V3 peptide pulsed target cells, mice were immunized with vCP112. After each immunization, or in vitro stimulation 21 days after the first inoculation a two-step depletion procedure was performed, and the spleen cells were assessed for cytotoxicity against V3 peptide pulsed P815 cells. Mice inoculated with the canarypox vector ALVAC did not generate spleen cells capable of killing peptide pulsed targets. Following a single immunization, vCP112 induced spleen cells able to kill V3 peptide pulsed targets. The lytic effector cells were sensitive to treatment with anti-murine Thy 1.2 or Lyt 2.2 plus complement and were resistant to anti-CD4. FIG. 10 shows the sensitivity of the cytotoxic effector cells from spleen cells of mice immunized with vCP112 to antibodies against cytotoxic T lymphocyte cell surface antigens Thy 1.2 and Lyt 2.2. Neither complement nor any of the monoclonal antibodies or alloantisera alone affected the cytolytic action of these cells. Similar results were obtained five days after a second immunization administered on day 30. Twenty-one days after a single inoculation, in vitro stimulation with vCP112 infected syngeneic spleen cells gave rise to lytic effector cells only partially sensitive to anti-Thy 1.2 although completely sensitive to anti-Lyt 2.2 and resistant to anti-CD4. These Thy 1.2-, CD4-, Lyt 2.2+effector cells are not seen following in vitro stimulation with vP911 of spleen cells from vCP112 inoculated mice. Nonetheless, it is clear that HIV V3 loop specific cytotoxicity was mediated by a population of T lymphocytes expressing Thy 1.2 and Lyt 2.2, but not CD4. This cell surface phenotype is characteristic of classical cytotoxic T lymphocytes.

EXAMPLE 8

SPECIFICITY OF CTL ANTIGEN RECEPTOR RECOGNITION OF THE V3 LOOP REGION OF HIV gp120

Figure 8:
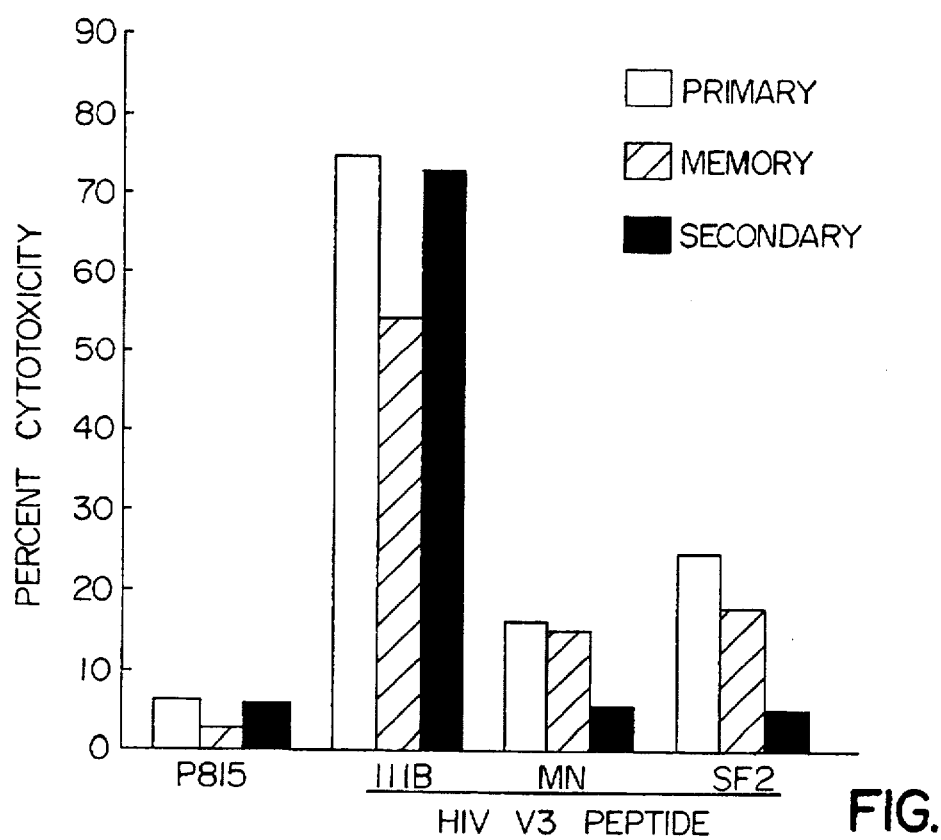
FIG. 8 shows the specificity of cytotoxic T lymphocyte antigen receptor for the HIV II B hypervariable V3 loop of gp120, but not for the V3 loop of HIV MN or SF2.

To examine the specificity of cytotoxic cells generated by the HIV canarypox virus (ALVAC) recombinant, vCP112 susceptibility to CTL activity was compared among P815 target cells pulsed with peptides corresponding the V3 loop region of gp120 of HIV isolates IIIB, MN, or SF2. HIV specific primary CTL activity was confined only to P815 target cells pulsed with peptide corresponding to the V3 loop of HIV isolate IIIB, but not target cells pulsed with peptides corresponding to the V3 loop region of gp120of HIV isolates MN or SF2, as shown in FIG. 8 which illustrates the specificity of cytotoxic T lymphocyte antigen receptor for the HIV IIIB hypervariable V3 loop of gp120, but not for the V3 loop of HIV MN or SF2. Similar results were obtained with in vitro stimulated, HIV specific memory CTL activity and secondary CTL activity induced by immunization with the ALVAC recombinant vCP112. Thus, HIV specific CTLs elicited by a recombinant canarypox virus expressing the env gene of HIV isolate IIIB recognize only target epitopes derived from the same antigenic isolate. These results clearly indicate the exquisite specificity of the lymphocyte effector cells generated by immunization with the HIV canarypox virus recombinant and eliminate such nonspecific effector mechanisms as natural killer (NK) cell activity.

EXAMPLE 9

Figure 9:
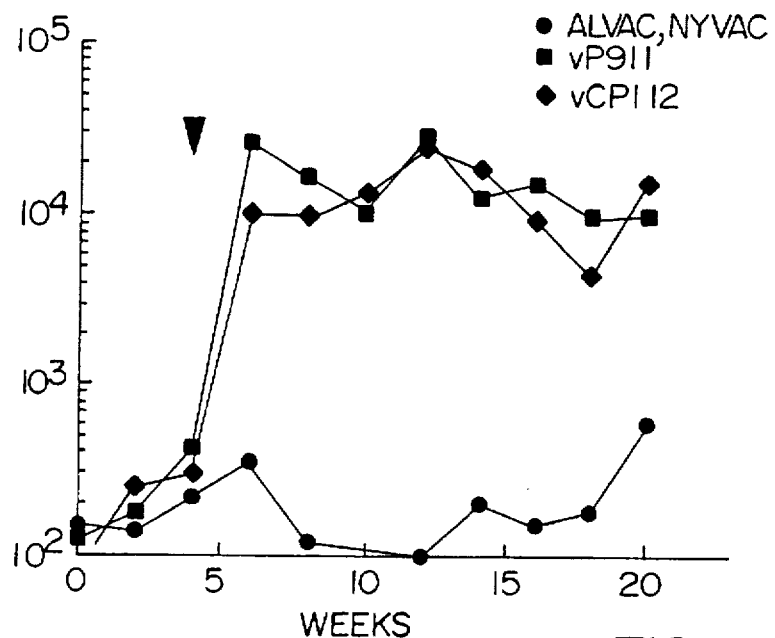
FIG. 9 shows the antibody responses to HIV III B gp120 of mice immunized with vectors (NYVAC, ALVAC) or with vaccinia virus recombinant vP911 or canarypox recombinant vCP112 expressing HIV-1 env (inverted triangle indicates time of administration of second inoculation)

ANTIBODY RESPONSES OF MICE INOCULATED WITH NYVAC- and ALVAC-BASED HIV RECOMBINANTS To evaluate humoral responses to HIV, mice were immunized at day 0 with a NYVAC HIV recombinant or canarypoxvirus (ALVAC) recombinant and received a secondary immunization at week four. The mice were bled at various intervals through 20 weeks after the initial immunization. Pooled sera from each treatment group were assayed for antibodies to HIV by ELISA employing purified gp120 as antigen; the results are shown in FIG. 9 which provides the antibody responses to HIV IIIB gp120 of mice immunized with vectors (NYVAC, ALVAC) or with NYVAC recombinant vP911 or ALVAC recombinant (vCP112) expressing HIV-1 env, wherein the inverted triangle indicates the time of administration of the second inoculation. Primary antibody responses were generally modest, but detectable. Following the secondary immunization, the antibody titers of mice immunized with both vP911 and vCP112 increased and peaked at week six with titers of over 10,000. These antibody titers remained at approximately the same levels throughout the duration of the study. Thus, an ALVAC HIV recombinant, vCP112, was capable of inducing a significant antibody response.

Inoculation of mice with ALVAC expressing the env gene of HIV-1 elicits spleen cell reactivity with characteristics of cytotoxic T lymphocytes: the requirement for immunization, cell surface phenotype, memory, and elegant epitope specificity. Furthermore, antibody responses to HIV-1 gp120 are induced by inoculation with this ALVAC recombinant.

EXAMPLE 10

DERIVATION OF NYVAC- AND ALVAC-BASED HIV-1 RECOMBINANTS AND EXPRESSION OF HIV-1(MN) env BY ALVAC AND NYVAC HIV-1(MN) env sequences were derived from plasmid pMN1.8-9 and pMN1.8-10 which contain a 1774 bp and 1803 bp subfragment from a genomic cDNA clone of HIV-1(MN), respectively. These plasmids were provided by the laboratory of Dr. R. C. Gallo (NCI-NIH). A 1,026 bp KpnI/EcoRI fragment was derived by amplifying these sequences from pMN1.8-9 by PCR using oligonucleotides HIVMN6 (SEQ ID NO:82) (5'-GGGTTATTAATGATCTGTAG-3') and HIV3B2 (SEQ ID NO:39) followed by digestion with KpnI/EcoRI. This fragment was inserted into pBS-SK digested with KpnI and EcoRI to yield pBSMIDMN.

A 1,028 bp SalI/XbaI fragment was derived from pMN1.8-10 by PCR using oligonucleotides HIVMN5 (SEQ ID NO:83) (5'-ATCATCGAGCTCTGTTCCTTGGG-TTCTTAG-3') and HIVMN3P (SEQ ID NO:84) (5'-ATCATCTCTAGAATAAAAATTATAGCAAAGCCCTTT-CCAAGCC-3') followed by digestion with SacI and XbaI. This fragment was co-ligated into pBS-SK digested with EcoRI and XbaI with a 404 bp EcoRI/SacI fragment. The 404 bp fragment was derived by PCR with pMN1.8-9 as template and oligonucleotides HIV3B1 (SEQ ID NO:32) and HIVMN4 (SEQ ID NO:85) (5'-ATCATCGAGCTCCTATCGCTGCTC-3'). The resultant plasmid was designated as pBS3MN.

The 1,026 bp EcoRI/KpnI fragment from pBSMIDMN was inserted into the 4,315 bp pBS3MN digested with EcoRI/KpnI to generate pBSMID3MN. This plasmid contains most of the env gene except the 5'-most region. The vaccinia virus H6 promoter (Goebel et al., 1990a,b) and the 5'-most region of the env gene were obtained by isolating a 318 bp KpnI fragment from pBSH6HIV3B5P (defined in Example 2). This fragment was ligated into KpnI/XbaI digested PBS-SK along with the 2.9 bp KpnI/XbaI fragment from pBSMID3MN. The resultant plasmid was designated as pH6HMNE.

The 2.7 kb NruI/XbaI fragment from pH6HMNE, containing the entire HIV-1(MN) env gene juxtaposed 3' to the 3'-most 26 bp of the H6 promoter, was blunt-ended and inserted into NruI/SmaI digested pSPHAH6. This generated plasmid pHAHIVMNE. Plasmid pSPHAH6 was derived as follows. Plasmid pMP2VCL (containing a polylinker region within vaccinia sequences upstream of the K1L host range gene) was digested within the polylinker with HindIII and XhoI and ligated to annealed oligonucleotides SPHPRHA A through D (SPHPRHA A (SEQ ID NO:86) 5'-AGCTTCTTTATTCTATACTTAAAAAGTGAAAAT-AAATACAAAGGTTCTTGAGGGT - 3'SPHPRHA B (SEQ ID NO:87) (5'-TGTGTTAAATTGAAAGCGAGAAATAAT-CATAAATTATTTCATTATCGCGATATC-CGTTAAGTTTG TATCGTAC-3') SPHPRHA C (SEQ ID NO:88) (3'-TTATTAGTATTTAATAAAGTAATAGCG-CTATAGGCAATTCAAACATAGCATGAGCT-5') SPH-PRHA D (SEQ ID NO:89) (3'-AGAAATAAGATATGAATTTTTCACTTTTATTTATG-TTTCCAAGAACTCCCAACACAATTTAA- CTT TCGCTCT-5') generating pSP126 containing a HindIII site, H6 promoter -124 through -1 (Perkus et al., 1989) and XhoI, KpnI, SmaI, SacI and EcoRI sites.

Plasmid pSD544 (containing vaccinia sequences surrounding the site of the HA gene replaced with a polylinker region and translation termination codons in six reading frames) was digested with XhoI within the polylinker, filled in with the Klenow fragment of DNA polymerase I and treated with alkaline phosphatase. SP126 was digested with HindIII, treated with Klenow and the H6 promoter isolated by digestion with SmaI. Ligation of the H6 promoter fragment to pSD544 generated pSPHAH6 which contained the H6 promoter in the polylinker region (in the direction of HA transcription). This insertion plasmid enables the replacement of the vaccinia HA gene (A56; Goebel et al., 1990a,b) with foreign genetic material.

The C5L insertion plasmid was derived as follows. Using the cosmid vector pVK102 (Knauf and Nester, 1982), a genomic library for vCP65 (ALVAC-based rabies G recombinant with rabies in C5 locus) was constructed. This library was probed with the 0.9 kb PvuII canarypoxvirus genomic fragment contained within pRW764.5 (C5 locus). These canarypox DNA sequences contain the original insertion locus. A clone containing a 29 kb insert was grown up and designated pHCOS1. From this cosmid containing C5 sequences, a 3.3 kb Cla fragment was subcloned. Sequence analysis from this ClaI fragment was used to extend the map of the C5 locus from 1-1372.

The C5 insertion vector, pC5L, was constructed in two steps. The 1535 bp left arm was generated by PCR amplification using oligonucleotides C5A (SEQ ID NO:90) (5'-ATCATCGAATTCTGAATGTTAAATGTTATACTTTG-3') and C5B (SEQ ID NO:91) (5'-GGGGGTACCTTTGAGAGTACCACTTCAG-3'). The template DNA was canarypoxvirus genomic DNA. This fragment was cloned into EcoRI/SmaI digested pUC8. The sequence was confirmed by standard sequencing protocols. The 404 bp right arm was generated by PCR amplification using oligonucleotides C5C (SEQ ID NO:92) (5'-ATCATCCTGCAGGTATTCTAAACTAGGAATAGATG-3') and C5DA (SEQ ID NO:93) (5'-ATCATCCTGCAGGTATTCTAAACTAGGAATAGATG-3). This fragment was then cloned into the vector previously generated containing the left arm digested with SmaI/PstI. The entire construct was confirmed by standard sequence analysis and designated pC5L. This insertion plasmid enables the insertion of foreign genes into the C5 locus.

The 2.8 kb XbaI/partial KpnI fragment from pH6HMNE was isolated and inserted into pC5L digested with XbaI and KpnI. The resultant plasmid was designated as pC5HIVMNE.

Plasmids pHAHIVMNE and pC5HIVMNE were used in vitro recombination experiments with NYVAC (vP866) and ALVAC (CPpp), respectively, as the rescue virus. These were done by standard procedures (Piccini et al., 1987). Plaques derived from recombinant virus were identified by plaque hybridization using a radiolabeled env-specific DNA probe (Piccini et al., 1987). After three rounds of plaque purification, the recombinant viruses were amplified. The NYVAC-based HIV-1(MN) env recombinant was designated vP1008 and the ALVAC-based recombinant vCP125.

Recombinant viruses, vCP125 and vP1008, were analyzed for expression of the HIV-1(MN) env gene by immunofluorescence and immunoprecipitation using previously reported procedures (Taylor et al., 1990). Pooled human sera from HIV-seropositive individuals (obtained from Dr. K. Steimer, Chiron Corp., Emeryville, Calif.) was used in these assays. Results from immunofluorescence revealed that cells infected with either vCP125 or vP1008 express the HIV-1 (MN) gene product on their surface. Immunoprecipitation from lysates prepared from vP1008 and vCP125 infected cells demonstrated the presence of three predominant HIV-1-specific proteins with apparent molecular masses of 160 kDa, 120 kDa, and 41 kDa, respectively. These are consistent with expression of the precursor envelope glycoprotein (160 kDa) and the proteolytically derived mature forms (120 kDa and 41 kDa).

EXAMPLE 11

EXPRESSION OF THE HIV-1(MN) gp120 BY NYVAC AND ALVAC

A 391 bp EcoRI/XbaI fragment was amplified from pBS3MN using oligonucleotides T7 (SEQ ID NO:94) (5'-AATACGACTCACTATAG-3') and HIVMN120 (SEQ ID NO:95) (5'-ATCATCTCTAGAAT-AAAAATTATCTTTTTTCTCTCTGCACCACTC-3') followed by digestion with EcoRI and XbaI. This fragment was ligated to the 4.2 kb EcoRI/XbaI fragment derived from pH6HMNE (defined in Example 10). The resultant plasmid contains a poxvirus expression cassette for HIV-1(MN) gp120 in pBS-SK and was designated pBSHIVMN120.

A 1.7 kb XbaI/partial KpnI fragment was isolated and inserted into pC5L digested with KpnI/XbaI. The resultant plasmid was designated as pC5HIVMN120. The insertion plasmid for integrating the HIV-1(MN) gp120 gene into NYVAC was obtained by first isolating the 1.6 kb NruI/SmaI fragment from pBSHIVMN120. This fragment was inserted into pSPHAH6 digested with NruI and SmaI to provide pHAHIVMN120.

Insertion plasmids, pC5HIVMN120 and pHAHIVMN120, were used in recombination experiments with ALVAC (CPpp) and NYVAC (vP866) as the rescuing virus. These assays and plaque identification and purification were performed by standard procedures (Piccini et al., 1987). Hybridization analyses were performed with a radiolabeled HIV-1(MN) gp120-specific probe. Purified recombinants were amplified. The ALVAC-based HIV-1(MN) gp120 recombinant was designated as vCP124 and the NYVAC-based HIV-1(MN) gp120 recombinant as vP1004.

Cells infected with vCP124 and vP1004 were analyzed for the presence of the recombinant expressed HIV-1(MN) gp120 by immunofluorescence and immunoprecipitation. These assays were performed as previously described (Taylor et al., 1990) using a pooled human sera from HIV-seropositive individuals (obtained from K. Steimer, Chiron Corporation, Emeryville, Calif.). Results from these studies clearly indicated that cells infected with either vCP124 and vP1004 contained HIV-1(MN) gp120, whereas gp120 was not observed in uninfected cells and cells infected with parental viruses, ALVAC and NYVAC.

EXAMPLE 12

EXPRESSION OF A NON-CLEAVABLE FORM OF HIV-1 gp160 BY ALVAC AND NYVAC

In order to express a non-cleavable form of the HIV-1 (IIIB) gp160 an arginine to threonine mutation was engineered at amino acid 511 (Ratner et al., 1985) as was demonstrated by Guo et al. (1990). These modifications were made to decrease the shedding of gp120 from the surface of infected cells. These manipulations were performed as follows. A 376 bp PstI/XbaI fragment was obtained by first amplifying the sequences from pBSHIV3BEII (described in Example 2) using oligonucleotides HIV3B2A (SEQ ID NO:96) (5'-GAAATAATAAAACAATAATC-3') and HIVECB (SEQ ID NO:97) (5'-GCTCCTATTCCCACTGCAGTTTTTTCTCTCTGCAC-3') followed by digestion with PstI and XbaI. This fragment was ligated with a 1,061 bp PstI/XbaI fragment and a 4.5 kb EcoRI/XbaI fragment from pBSHIV3BEII to yield pBSHIV3BEEC.

The central region of the Hantaan virus S segment was generated by PCR using oligonucleotides T5HT3PPS (SEQ ID NO:98) (5'GTCCTGCAGGATGGAAAAGAATGCCCCAAGC-3') and HTS55PN (SEQ ID NO:99) (5'-GGGGGAGGCAAACTACCAAGG-3') and the S⁻ specific cDNA clone as template. The 581 bp fragment contains a PstI site at its 3' end and the 5' end includes the NciI site of position 499 of the S segment (Schmaljohn et al., 1986). Furthermore, using the oligonucleotide T5HT3PPS (SEQ ID NO:98) eliminates the $T_5NT$ element at position 1029 to 1035 without altering the amino acid sequence. This fragment was then digested with NciI and PstI. The PCR fragment containing the 5' end of the coding sequence fused to the H6 promoter (HindIII/NciI digested above) was ligated into pBS-SK digested with HindIII and PstI along with the 581 bp NciI/PstI fragment containing the central region of the S segment. The resultant plasmid was designated pBSHTSH65P.

The 3' most 438 bp of the S segment was derived by PCR using oligonucleotides HTS3PXBA (SEQ ID NO:100) (5'-ATCATCTCTAGAATAAAAATTAGAGTTTCAAAGGC-3') and T5HT5PSP (SEQ ID NO:101) (5'-CGCCAGCATGCAGAAGCAGC-3') and the S-specific cDNA clone as template. The 5' end of this fragment contains the PstI site situated at position 1039 of the S segment coding sequence (Schmaljohn et al., 1986) and the 3' end contains a T$_5$NT sequence motif and a unique XbaI prior to insertion into PstI/XbaI digested pBS-SK to yield pBSHTS3P.

To generate the entire S segment expression cassette, a 1122 bp PstI/partial HindIII fragment was derived from pBSHTSH56P. This fragment was co-inserted into HindIII/XbaI digested pBS-SK with a 290 bp PstI/XbaI fragment from pBSHTS3P. The resultant plasmid was designated pBSHVS by linearization with XbaI followed by a partial HindIII digestion.

The 2.6 kb NruI/XbaI fragment from pBSHIV3BEEC, containing the 3'-most 26 bp of the H6 promoter linked to the gp160 cassette, was isolated and ligated to a 3.0 kb NruI/XbaI fragment of pBSHVS to yield pBSHIV3BEECM. Digestion with NruI and XbaI excises the 3'-most 26 bp of the H6 promoter and the Hantaan virus S sequence. The 3.0 kb NruI/XbaI fragment contains the 5'-most 100 bp of the H6 promoter in a PBS-SK plasmid.

The 2.8 kb XbaI/partial KpnI fragment from pBSHIV3BEECM was ligated to XbaI/KpnI digested pC5L to yield pC5HIV3BEEC. A 2.7 kb NruI/XbaI fragment from pBSHIV3BEECM was blunt-ended with the Klenow fragment of the *E. coli* DNA polymerase and inserted into NruI/SmaI digested pSPHAH6 to yield pHAHIV3BEEC.

The insertion plasmids, pC5HIV3BEEC and pHAHIV3BEEC, were used in in vitro recombination experiments by standard procedures (Piccini et al., 1987) using ALVAC (CPpp) and NYVAC (vP866), respectively, as rescue virus. Recombinant plaques were identified by standard plaque hybridization analysis (Piccini et al., 1987) using a radiolabeled probe specific for the HIV-1 env gene. Recombinant viruses were amplified following three rounds of purification. The recombinant ALVAC-based HIV-1(IIIB) gp160 (non-cleavable) was designated as vCP126 and the NYVAC-based equivalent as vP1020.

Immunofluorescence and immunoprecipitation analyses were performed by previously described procedures on vP1020 and vCP126 infected cells using pooled human serum from HIV-seropositive individuals (obtained from K. Steimer, Chiron Corp., Emeryville, Calif.). Immunofluorescence results clearly demonstrated the surface expression of the HIV-1(IIIB) gp160 (non-cleavable form) on the surface of cells infected with either vCP126 or vP1020. Furthermore, immunoprecipitation results demonstrated the presence of a HIV-1(IIIB) gp160 in these infected cells that was not proteolytically cleaved into the mature gp120 and gp41 frames.

A non-cleavable form of the HIV-1(MN) gp160 was also pursued and the recombinant viruses obtained as follows.

A PstI/XbaI fragment was obtained by PCR amplification from pH6HMNE (described in Example 10) using oligonucleotides HIVMN3P (SEQ ID NO:102) (5'-ATCATCTCTAGAATAAAAATTATAGGAAAGCCCTTTCCAAGCC-3') and HIVECA (SEQ ID NO:103) (5'-GTGCAGAGAAAAAACTGCAGTGGGAATAGGAGC-3') followed by digestion with PstI and XbaI. This 1061 bp fragment was ligated with the 391 bp EcoRI/PstI from pBSHIVMNT (described in Example 13) and the 4.2 kb EcoRI/XbaI fragment from pH6HMNE (defined in Example 10). The resultant plasmid was designated as pBSHIVMNEEC[1]. Sequence analysis of the HIV env insert demonstrated that a single nucleotide was missing (between the SacI and XbaI sites). To correct this, the following manipulations were performed. The 1.028 kb SacI/XbaI from pH6HMNE was used to substitute for the corresponding fragment from pBSHIVMNEEC resulting in the formation of pBSHIVMNEEC.

The 2.6 NruI/XbaI fragment from pBSHIVMNEEC was isolated, blunt-ended with Klenow, and inserted into NruI/SmaI digested pSPHAH6 (defined in Example 10). The resultant plasmid was designated pHAHIVMNEEC. The 2.6 kb NruI/XbaI fragment from PBSHIVMNEEC was also inserted into NruI/XbaI digested pVQH6C5LSP6 (below) to yield pC5HIVMNEEC.

Insertion plasmids, pHAHIVMNEEC and pC5HIVMNEEC, were used in standard recombination experiments (Piccini et al., 1987) with NYVAC (vP866) and ALVAC (CPpp), respectively, as rescue virus. Recombinant virus was identified and plaque purified by standard plaque hybridization (Piccini et al., 1987) using a radiolabeled HIV env-specific DNA probe. Purified recombinant virus were then amplified. The NYVAC-based recombinant containing the HIV-1 (MN) non-cleavable gp160 was designated as vP1078 and the ALVAC equivalent vCP144.

Expression analysis of vCP126 and vP1078 was performed as described above. These results demonstrated that expression was qualitatively equivalent to the HIV-1(IIIB) counterparts, vP1020 and vCP126.

EXAMPLE 13

EXPRESSION OF A NON-CLEAVABLE, SECRETED FORM OF HIV-1 env BY ALVAC AND NYVAC

ALVAC- and NYVAC-based recombinant viruses were generated which express an HIV-1(MN) env that is not proteolytically cleaved and is secreted by virtue of the elimination of the transmembrane sequence near the carboxy terminus of the gene product. A 502 bp PstI/XbaI fragment was obtained by first amplifying these sequences from pH6HMNE (defined in Example 10) using oligonucleotides HIVECA (SEQ ID NO:103) and HIVMNT1 (SEQ ID NO:104) (5'-ATCATCTCTAGAATAAAAATTACAAACTTGCCCATTTATCCAATTCC-3') followed by digestion with PstI (5'-end) and XbaI (3'-end). This fragment corresponds to nucleotides 7219 to 7808 (Ratner et al., 1985). This fragment will serve as the 3'-end of the env expression cassette. As such, the env gene product will lack the transmembrane region, will be terminated by a termination codon provided by oligonucleotide HIVMNT1 (SEQ ID NO:104), and will not be cleaved due to an amino change at 511 (defined in Example 12) provided using oligonucleotide HIVECA (SEQ ID NO:103). This 502 bp fragment was ligated to the 391 bp EcoRI/PstI fragment derived by PCR from pH6HMNE using oligonucleotides HIV3B1 (SEQ ID NO:32) and HIVECB (SEQ ID NO:97), and the 4.2 kb EcoRI/XbaI fragment to pH6MNE. The resultant plasmid was designated pBSHIVMNT.

The 2.2 kb XbaI/partial KpnI fragment from pBSHIVMNT was isolated and inserted into pC5L digested with XbaI and KpnI. The resultant plasmid was designated as pC5HIVMNT. The NYVAC insertion plasmid was derived by isolating the 2.1 kb NruI/XbaI fragment from pBSHIVMNT. This fragment was then blunt-ended with the Klenow fragment of the *E. coli* DNA polymerase in the presence of 2 mM dNTPs and inserted into pSPHAH6 digested with NruI and SmaI to yield pHAHIVMNT.

The insertion plasmids. pC5HIVMNT and pHAHIVMNT, were used in standard recombination experiments (Piccini et al., 1987) with ALVAC (CPpp) and NYVAC (vP866), respectively, as the rescue virus. Recombinant virus was identified by standard plaque hybridization assays (Piccini et al., 1987) using a radiolabeled HIV env-specific probe. Recombinant virus was subjected to three rounds of purification prior to amplification. The ALVAC-based HIV-1(MN) env (non-cleavable; secreted) was designated as vCP120 and the NYVAC equivalent as vP994.

Immunoprecipitation analyses were performed as previously described (above) for vCP120 and vP994 infected cells using pooled human sera from HIV-seropositive individuals. Both vCP120 and vP994 expressed an HIV-1(MN) env-specific gene product with a molecular weight consistent with a non-cleavable, truncated gene product. Furthermore, immunoprecipitation of the cell-free medium from vCP120 and vP994 infected cell cultures indicated the secretion of this env gene product.

A similar construction was engineered for the HIV-1(IIIB) env. The following manipulations were performed to accomplish this. A 487 bp PstI/XbaI fragment was obtained by first amplifying these sequences from pBSH6HIV3B5P (defined in Example 2) using oligonucleotides HIVECA (SEQ ID NO:103) and HIV3BT (SEQ ID NO:105) (5'-ATCATCTCTAGAATAAAAATTACAAACTTGCCCA-TTTATCTAATTCC-3') followed by digestion with PstI and XbaI. A 397 bp EcoRI/PstI fragment was isolated from pBSHIV3BEEC and a 4.2 kb EcoRI/XbaI fragment was isolated from pH6HIIIBEM. These three fragments were ligated together to yield pBSHIV3BT1. Plasmid pH6HIIIBEM was derived from pBSHIV3BEII (defined in Example 2) by digestion with KpnI to liberate a second copy of the H6 promoter linked to the 5' portion of the HIV-1 (IIIB) env gene. The 5.4 kp KpnI was then religated to form pBSHIV3BEII.

The 2.1 kb and 2.9 kb fragments derived by HindIII/XbaI digestion of pBSHIV3BEECM were ligated to the 105 bp HindIII/XbaI fragment from pBSHIV3BT1 to yield pBSHIV3BT. This plasmid was digested with NruI and XbaI to excise a 2.1 kb fragment. This fragment was blunt-ended and inserted into pSPHAH6 digested with NruI and SmaI to generate pHAHIV3BT.

The plasmid pHAHIV3BT was used in recombination experiments, as above, with NYVAC (vP866) as the rescue virus. Recombinant virus was identified and purified as above and the resultant recombinant was designated as vP1036. This recombinant had all the expression characteristics noted above for vCP120 and vP994.

EXAMPLE 14

EXPRESSION OF HIV-1(MN) gp120 ANCHORED WITH A TRANSMEMBRANE SEQUENCE BY NYVAC AND ALVAC

To fuse the env region encoding the gp120 to the region encoding the hydrophobic transmembrane sequence, the following manipulations were performed. A 200 bp fragment corresponding to the 3'-most region of the gp120 coding sequence was derived by PCR from pH6HMNE (defined in Example 10) using oligonucleotides HIV3B1 (SEQ ID NO:32) and HIVMN18 (SEQ ID NO:106) (5'-GCCTCCTACTATCATTATGAATAATCTTTTTCTCTC-TG-3'). This fragment was fused by PCR to annealed oligonucleotides HIVTM1 (SEQ ID NO:107) (5'-TTATTCATAATGATAGTAGGAGGCTTGG-TAGGTTTAAGAATAGTTTTTGCTG-TACTCTCTGTAGT GAATAGAGTTAGGCAGGGATAA-3') and HIVTM2 (SEQ ID NO:108) (5'-TTATCCCTGCCTAACTCTATTCACTACAGAGAGTA-CAGCAAAAACTATTCTTAAACCTACCAAGC CTCCTACTATCATTATGAATAA-3') using oligonucleotides HIV3B1 (SEQ ID NO:32) and HIVTM3 (SEQ ID NO:109) (5'-ATCATCTCTAGAATAAAAATTATCCC-TGCCTAACTCTATTCAC-3'). Oligonucleotides HIVTM1 (SEQ ID NO:107) and HIVTM2 (SEQ ID NO:108) correspond to nucleotides 7850 to 7934 (Ratner et al., 1985) and represent the region encoding the HIV env hydrophobic anchor sequence. Fusion with HIVTM3 (SEQ ID NO:109) engineers the 3'-end of the eventual cassette with a termination codon and a 3'XbaI site. The derived fragment was digested with EcoRI/XbaI and ligated to pH6HMNE digested with EcoRI and XbaI to yield pBSHIVMN120T.

The 1.7 bk NruI/XbaI fragment from pBSHIVMN120T, containing the 3'-most 26 bp of the H6 promoter and the entire HIV-1 cassette, was isolated and inserted into the 5.1 kb NruI/XbaI fragment from pVQH6C5LSP6 to derive pC5HIVMN120T. The plasmid pVQH6C5LSP6 was derived as follows.

pC5L (defined in Example 10) was digested within the polylinker with Asp718 and NotI, treated with alkaline phosphatase and ligated to kinased and annealed oligonucleotides CP26 (SEQ ID NO:110) (5'-GTACGTGACTAATTAGCTATAAAAAGGATCCGGTA-CCCTCGAGTCTAGAATCGATCCC- GGGTTTT TATGACTAGTTAATCAC-3') and CP27 (SEQ ID NO:111) (5'-GGCCGTGATTAACTAGTCAT- AAAAACCCGG-GATCGATTCTAGACTCGAGGGTACCGGATCCTTTT TATAGCTAATTAGTCAC-3') (containing a disabled Asp718 site, translation stop codons in six reading frames, vaccinia early transcription termination signal (Yuen and Moss, 1987), BamHI, KpnI, XhoI, XbaI, ClaI, and SmaI restriction sites, vaccinia early transcription termination signal, translation stop codons in six reading frames, and a disabled NotI site) generating plasmid pC5LSP.

pC5LSP was digested with BamHI and ligated to annealed oligonucleotides CP32 (SEQ ID NO:112) (5'-GATCTTAATTAATTAGTCATCAG-GCAGGGCGAGAACGAGACTATCT-GCTCGTTAATTAATTAGGT CGACG-3') and CP33 (SEQ ID NO:113) (5'-GATCCGTCGACCTAATTAATTAACGAG-CACATAGTCTCGTTCTCGCCCTGCCT-GATGACTAATTA ATTAA-3') to generate pVQC5LSP6.

The 1.7 kb NruI/XbaI fragment from pBSHIVMN120T was also blunt-ended and inserted into pSPHAH6 digested with NruI and SmaI. The resultant plasmid was designated as pHAHIVMN120T.

Insertion plasmids, pC5HIVMN120T and pHAHIVMN120T, were used in standard recombination experiments (Piccini et al., 1987) with ALVAC and NYVAC, respectively, as the rescue virus. Recombinant virus was identified and purified by standard plaque hybridization (Piccini et al., 1987) using a radiolabeled HIV-1 gp120-specific DNA probe. The pure populations were amplified and the ALVAC-based anchored HIV-1(MN) gp120 recombinant was designated vCP138. The NYVAC-based equivalent was designated vP1035.

Immunofluorescence and immunoprecipitation analyses were performed by standard procedures (above) to evaluate expression of the HIV-1(MN) anchored gp120 in vP138 and vP1035 infected cells. The assays were performed using pooled human sera from HIV-seropositive individuals (obtained from Dr. K. Steimer, Chiron Corp., Emeryville, Calif.). Investigation of surface immunofluorescence indicated that vCP138 and vP1035 infected cells contained HIV-1(MN) gp120 in the plasma membrane. Significantly, the surface staining of vCP138 and vP1035 infected cells was enhanced compared to cells infected with recombinant viruses (i.e. vCP125, vCP124, vP1004, and vP1008) expressing gp160 or a non-anchored gp120. Results from immunoprecipitation analyses confirmed the expression of gp120 in vCP138 and vP1035 infected cells and that the expressed product was of the expected molecular mass.

EXAMPLE 15

GENERATION OF NYVAC/HIV-1 GAG (PROTEASE⁻) RECOMBINANT

Plasmid pSD542 (a NYVAC TK locus donor plasmid; see Example 5) was derived from plasmid pSD460 (Tartaglia et al., 1992) by forming vector plasmids pSD513 as described above in Example 7. The polylinker region in pSD513 was modified by cutting with PstI/BamHI and ligating to annealed synthetic oligonucleotides MPSYN288 (SEQ ID NO:114) (5'GGTCGACGGATCCT 3') and MPSYN289 (SEQ ID NO:115) (5'GATCAGGATCCGTCGACCTGCA 3') resulting in plasmid pSD542.

A plasmid, pHXB2D, containing human immunodeficiency virus type 1 (HIV-1) cDNA sequence was obtained from Dr. R. C. Gallo (NCI-NIH). The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542. The plasmid generated by this manipulation is called pHIVG2.

The 3'-end of the gag gene was then cloned downstream from the rest of the gag gene. This was accomplished by cloning a 280 bp ApaI-BamHI PCR fragment, containing the 3'-end of the gag gene, into the 5,620 bp ApaI-BamHI fragment of pHIVG2. This PCR fragment was generated from the plasmid, pHXB2D, with the oligonucleotides, HIVP5 (SEQ ID NO:116) (5'-TGTGGCAAAGAAGGGC-3') and HIVP6 (SEQ ID NO:117) (5'-TTGGATCCTTATTGTGACGAGGGGTC-3'). The plasmid generated by this manipulation is called pHIVG3.

The I3L promoter was then cloned upstream of the gag gene. This was accomplished by cloning the oligonucleotides, HIVL17 (SEQ ID NO:118) (5'-GATCTTGAGATAAAGTGAAAATATAT-CATTATATTACAAAGTACAATTATTTAGGTTTAATCA TGGGTGCGAGAGCGTCAGTATTAAGCGGGGGAG-AATTAGAT-3') and HIVL18 (SEQ ID NO:119) (5'-CGATCTAATTCTCCCCCGCTTAATACT-GACGCTCTCGCACCCATGATTAAAC-CTAAATAATTGTA CTTTGT-AATATAATGATATATATTTTCACTTTATCTCAA-3'), encoding the vaccinia virus I3L promoter and the 5'-end of the gag gene, into the 5,540 bp partial BglII-ClaI fragment of pHIVG3. The plasmid generated by this manipulation is called pHIVG4.

pHIVG4 was used in recombination experiments with vP866 (NYVAC) as the rescuing virus to yield vP969.

Immunoprecipitation analysis was performed to determine whether vP969 expresses authentic HIV-1 gag precursor protein.

Lysates from the infected cells were analyzed for HIV-1 gag precursor expression using pooled serum from HIV-1 seropositive individuals (obtained from Chiron, Emeryville, Calif.). The sera was preadsorbed with vP866 infected Vero cells. The preadsorbed sera was bound to Protein A-sepharose in an overnight incubation at 4° C. Following this incubation period, the material was washed 4×with 1×buffer A. Lysates precleared with normal human sera and protein A-sepharose were then incubated overnight at 4° C. with the HIV-1 seropositive human sera bound to protein A-sepharose. After the overnight incubation period, the samples were washed 4×with 1×buffer A and 2×with a LiCl₂/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV-1 seropositive individuals specifically precipitated the HIV-1 gag precursor protein from vP969 infected cells, but did not precipitate HIV-1-specific proteins from mock infected or NYVAC infected cells.

EXAMPLE 16

GENERATION OF NYVAC/HIV-1 gag/pol RECOMBINANT

The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542 (defined in Example 15). The plasmid generated by this manipulation is called pHIVG2.

The 3'-end of the gag gene was then cloned into pHIVG2. This was accomplished by cloning a 280 bp ApaI-BamHI PCR fragment, containing the 3'-end of the gag gene, into the 5,620 bp ApaI-BamHI fragment of pHIVG2. This PCR fragment was generated from the plasmid, pHXB2D, with the oligonucleotides, HIVP5 (SEQ ID NO:116) and HIVP6 (SEQ ID NO:117). The plasmid generated by this manipulation is called pHIVG3.

The I3L promoter was then cloned upstream of the gag gene. This was accomplished by cloning the oligonucleotides, HIVL17 (SEQ ID NO:118) and HIVL18 (SEQ ID NO:119), encoding the vaccinia virus I3L promoter and the 5'-end of the gag gene, into the 5,540 bp partial BglII-ClaI fragment of pHIVG3. The plasmid generated by this manipulation is called pHIVG4.

The portion of the gag gene encoding p24, p2, p7 and p6 was then eliminated. This was accomplished by cloning the oligonucleotides, HIVL19 (SEQ ID NO:120) (5'-CTGACACAGGACACAGCAATCAGGT-CAGCCAAAATTACTAATTTTTATCTC-GAGGTCGACAGGAC CCG-3') and HIVL20 (SEQ ID NO:121) (5'-GATCCGGGTCCTGTCGACCTC-GAGATAAAAATTAGTAATTTTGGCTGAC- CTGATTGCTGTGTCCT GTGTCAG-3'), into the 4,450 bp partial PvuII-BamHI fragment of pHIVG4. The plasmid generated by this manipulation is called pHIVG5.

The remainder of the gag gene, as well as the pol gene, was then cloned downstream of the p17 "gene". This was accomplished by cloning the 4,955 bp ClaI-SalI fragment of pHXB2D, containing most of the gag gene and all of the pol gene, into the 4,150 bp ClaI-SalI fragment of pHIVG5. The plasmid generated by this manipulation is called pHIVG6.

Extraneous 3'-noncoding sequence was then eliminated. This was accomplished by cloning a 360 bp AflIII-BamHI PCR fragment, containing the 3'-end of the pol gene, into the 8,030 bp AflIII-BamHI fragment of pHIVG6. This PCR fragment was generated from the plasmid, pHXB2D, with the oligonucleotides, HIVP7 (SEQ ID NO:122) (5'-AAGAAAATTATAGGAC-3') and HIVP8 (SEQ ID NO:123) (5'-TTGGATCCCTAATCCTCATCCTGT-3'). The plasmid generated by this manipulation is called pHIVG7.

pHIVG7 was used in recombination experiments with vP866 (NYVAC) as the rescuing virus to yield vP989.

Immunoprecipitation experiments with vP989 infected cells were performed as described above for the expression of the HIV-1 gag precursor protein. No HIV-1-specific species were precipitated from mock infected or NYVAC infected Vero cells. Protein species corresponding to the gag precursor protein, as well as various intermediate and mature gag cleavage products, were precipitated, however, from lysates of vP989 infected cells.

EXAMPLE 17

GENERATION OF NYVAC/HIV-1 gag/pol AND env (gp120) RECOMBINANT

The sequence encoding the 5'-end of the gag gene was cloned between vaccinia virus tk flanking arms. This was accomplished by initially preparing plasmid pHIVG7, as described above (see Example 16).

pHIVG7 was used in recombination experiments with vP921 as the rescuing virus to yield vP991.

Immunoprecipitation experiments with vP991 infected cells were performed as described above for the expression of the HIV gag precursor protein. No HIV-specific species were precipitated from mock infected Vero cells. Protein species corresponding to the env and gag precursor proteins, as well as various intermediate and mature gag cleavage products, were precipitated, however, from lysates of vP991 infected cells.

EXAMPLE 18

GENERATION OF NYVAC/HIV-1 gag/pol AND env (gp160) RECOMBINANT

The sequence encoding the 5'-end of the gag gene was cloned between vaccinia virus tk flanking arms. This was accomplished by initially preparing plasmid pHIVG7, as described above (see Example 16).

pHIVG7 was used in recombination experiments with vP911 (above) as the rescuing virus to yield vP990.

Immunoprecipitation experiments with vP990 infected cells were performed as described above for the expression of the HIV-1 gag precursor protein. No HIV-1-specific species were precipitated from mock infected Vero cells. Protein species corresponding to the env and gag precursor proteins, as well as various intermediate and mature gag cleavage products, were precipitated, however, from lysates of vP990 infected cells.

EXAMPLE 19

GENERATION OF NYVAC/HIV-1 p17, p24 RECOMBINANT

A plasmid, pHXB2D, containing HIV-1 cDNA sequence, was obtained from Dr. R. C. Gallo (NCI-NIH). The sequence encoding the 5'-end of the gag gene was cloned between vaccinia virus tk flanking arms. This was accomplished by initially preparing pHIVG5, as described above (see Example 16).

The 3'-end of the p24 "gene" was then cloned into pHIVG5. This was accomplished by cloning a 660 bp SalI-BamHI PCR fragment, containing the 3'-end of the p24 "gene", into the 4,450 bp SalI-BamHI fragment of pHIVG5. This PCR fragment was generated from the plasmid, pHXB2D, with the oligonucleotides, HIVP25 (SEQ ID NO:124) (5'-AAAGTCGACCCATATCACCTAGAAC-3') and HIVP26 (SEQ ID NO:125) (5'-TTTGGATCCTTACAAAACTCTTGCCTTAT-3'). The plasmid generated by this manipulation is called pHIVG8.

The entomopox 42 kd promoter was then cloned upstream of the p24 "gene". This was accomplished by cloning the oligonucleotides, HIVL21 (SEQ ID NO:126) (5'-TCGAGCAAAATTGAAAATATATAATTA-CAATATAAAATGCCTATAGTGCAGAA-CATCCAGGGGCA AATGGTACAT-CAGGCCATATCACCTAGAACTTTAAATGCA-3') and HIVL22 (SEQ ID NO:127) (5'-TTTAAAGTTCTAGGTGATATGGCCTGAT-GTACCATTTGCCCCTGGATGTTCTGCAC-TATAGGCAT TTTATATTGTAATTATATATTTTCAATTTTGC-3'), encoding the entomopox 42 kd promoter and the 5'-end of the p24 "gene", into the 5,070 bp XhoI-NsiI fragment of pHIVG8. The plasmid generated by this manipulation is called pHIVG9.

pHIVG9 was used in recombination experiments with vP866 (NYVAC) as the rescuing virus to yield vP970.

Immunoprecipitation experiments with vP970 infected cells were performed as described above for the expression of the HIV-1 gag precursor protein. No HIV-1-specific species were precipitated from mock infected or NYVAC infected Vero cells. A protein species corresponding to p24 was precipitated, however, from lysates of vP970 infected cells.

EXAMPLE 20

GENERATION OF NYVAC/HIV-1 p17, p24 AND env (gp120) RECOMBINANT

A plasmid, pHXB2D, containing HIV-1 cDNA sequence, was obtained from Dr. R. C. Gallo (NCI-NIH). The sequence encoding the 5'-end of the gag gene was cloned between vaccinia virus tk flanking arms. This was accomplished by initially preparing plasmid pHIVG9 as described above (see Example 19).

pHIVG9 was used in recombination experiments with vP921 as the rescuing virus to yield vP973.

Immunoprecipitation experiments with vP973 infected cells were performed as described above for the expression of the HIV-1 gag precursor protein. No HIV-1-specific species were precipitated from mock infected Vero cells. Protein species corresponding to env and p24 were precipitated, however, from lysates of vP973 infected cells.

EXAMPLE 21

GENERATION OF NYVAC/HIV-1 p17, p24 AND env (gp160) RECOMBINANT

A plasmid, pHXB2D, containing HIV-1 cDNA sequence, was obtained from Dr. R. C. Gallo (NCI-NIH). The sequence

51 encoding the 5'-end of the gag gene was cloned between vaccinia virus tk flanking arms. This was accomplished by initially preparing plasmid pHIVG9, as described above (see Example 19).

pHIVG9 was used in recombination experiments with vP911 as the rescuing virus to yield vP971.

Immunoprecipitation experiments with vP971 infected cells were performed as described above for the expression of the HIV-1 gag precursor protein. No HIV-1-specific species were precipitated from mock infected Vero cells. Protein species corresponding to env and p24 were precipitated, however, from lysates of vP971 infected cells.

EXAMPLE 22

GENERATION OF NYVAC/HIV-1 gag (PROTEASE⁻) AND env (TRUNCATED) RECOMBINANT

A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by initially preparing plasmid pHIVG9 as described above (see Example 19).

An H6-promoted truncated HIV-1 envelope gene was then inserted into pHIVG4. This was accomplished by cloning the E. coli DNA polymerase I (Klenow fragment) filled-in 1,600 bp XhoI-NotI fragment of pHIVE10, containing an H6-promoted truncated HIV-1 envelope gene, into the filled-in BamHI site of pHIVG4. The plasmid generated by this manipulation is called pHIVGE11.

The plasmid pHIVE10 was derived by inserting a SacI/partial KpnI fragment from pBSHIV3BCDT1 into the multiple cloning region of pIBI25 (IBI, New Haven, Conn.). The plasmid pBSHIV3BCDT1 contains an H6 promoted cassette to express a severely truncated form of the HIV-1(IIIB) envelope (amino acid 1 to 447; Ratner et al., 1985). Expression of this cassette was evaluated to eliminate CD4 binding while retaining the V3 loop region and the T1 epitope.

To construct pBSHIV3BCDT1 the following manipulations were performed. A PCR-derived fragment of 200 bp was amplified from pBSH6HIV3B5P (defined in Example 2) using oligonucleotides HIV3B2A (SEQ ID NO:96) and HIVCD4A (SEQ ID NO:128) (5'-GCCTCCTACTATCATTATGAATAAACTGATGGGA-GGGGCATAC-3'). This fragment was fused by PCR to annealed oligonucleotides HIVTM1 (SEQ ID NO:107) and HIVTM2 (SEQ ID NO:108) using oligonucleotides HIV3B2A (SEQ ID NO:96) and HIVTM3 (SEQ ID NO:109). These manipulations create the 3'-end of the truncated env cassette by placing sequences encoding the HIV-1 env transmembrane anchor (amino acids 691 to 718; Ratner et al., 1985), a translation termination codon (TAA), and a 3' XbaI site. This PCR-fusion product was digested with EcoRI and XbaI to yield a 243 bp fragment. The fragment was ligated to the 4.5 bp EcoRI/XbaI fragment of pH6HIIIBE to generate pBSHIV3BCDT1.

pHIVGE11 was used in recombination experiments with vP866 (NYVAC) as the rescuing virus to yield vP979.

Immunoprecipitation experiments with vP979 infected cells were performed as described above for the expression of the HIV-1 gag precursor protein. No HIV-1-specific species were precipitated from mock infected or NYVAC infected Vero cells. Protein species corresponding to env and the gag precursor proteins were precipitated, however, from lysates of vP979 infected cells.

52

EXAMPLE 23

GENERATION OF NYVAC/HIV-1 gag/pol AND env (TRUNCATED) RECOMBINANT

The sequence encoding the 5'-end of the gag gene was cloned between vaccinia virus tk flanking arms. This was accomplished by initially preparing plasmid pHIVG7 as described above (see Example 16).

An H6-promoted truncated HIV-1 envelope gene was then inserted into pHIVG7. This was accomplished by cloning the E. coli DNA polymerase I (Klenow fragment) filled-in 1,600 bp XhoI-NotI fragment of pHIVE10 (defined in Example 22), containing an H6-promoted truncated HIV-1 envelope gene, into the filled-in BamHI site of pHIVG7. The plasmid generated by this manipulation is called pHIVGE12.

pHIVGE12 was used in recombination experiments with vP866 (NYVAC) as the rescuing virus to yield vP978.

Immunoprecipitation experiments with vP978 infected cells were performed as described above for the expression of the HIV-1 gag precursor protein. No HIV-1-specific species were precipitated from mock infected or NYVAC infected Vero cells. Protein species corresponding to the env and gag precursor proteins, as well as various intermediate and mature gag cleavage products, were precipitated, however, from lysates of vP978 infected cells.

EXAMPLE 24

GENERATION OF NYVAC/HIV-1 gag/pol AND env (gp120) RECOMBINANT

The sequence encoding the gag gene was cloned between vaccinia virus tk flanking arms. This was accomplished by initially preparing plasmid pHIVG7, as described above (see Example 16).

The I3L-promoted gag and pol genes were then inserted into a canary pox insertion vector. This was accomplished by cloning the 4,360 bp partial BglII-BamHI fragment of pHIVG7, containing the I3L-promoted gag and pol genes, into the BamHI site of pVQH6CP3L. The plasmid generated by this manipulation is called pHIVGE14.

The H6-promoted HIV-1(MN) envelope (gp120) gene was then inserted into pHIVGE14. This was accomplished by cloning the oligonucleotides, HIVL29 (SEQ ID NO:129) (5'-GGCCGCAAC-3') and HIVL30 (SEQ ID NO:130) (5'-TCGAGTTGC-3'), and the 1,600 bp NruI-NotI fragment of pBSHIVMN120, containing the H6-promoted gp120 gene, into the 11,500 bp NruI-XhoI fragment of pHIVGE14. The plasmid generated by this manipulation is called pHIVGE15.

The H6-promoted envelope (gp120) gene and the I3L-promoted gag and pol genes were then inserted into a vaccinia virus insertion vector. This was accomplished by cloning the 6,400 bp NotI-BamHI fragment of pHIVGE15, containing the H6-promoted gp120 gene and the I3L-promoted gag and pol genes, into the 4,000 bp NotI-BglII fragment of pSD542VCVQ. The plasmid generated by this manipulation is called pHIVGE16.

pHIVGE16 was used in in vitro recombination experiments with vP866 (NYVAC) as the rescuing virus to yield vP988.

Immunoprecipitation experiments with vP988 infected cells were performed as described above for the expression of the HIV-1 gag precursor protein. No HIV-1-specific species were precipitated from mock infected or NYVAC infected Vero cells. Protein species corresponding to the env and gag precursor proteins, as well as various intermediate and mature gag cleavage products, were precipitated, however, from lysates of vP988 infected cells.

EXAMPLE 25

GENERATION OF NYVAC/HIV-1 gag/pol AND env (gp160) RECOMBINANT

The sequence encoding the 5'-end of the gag gene was cloned between vaccinia virus tk flanking arms. This was accomplished by initially preparing plasmid pHIVGE16 as described above (see Example 24).

The gp120 gene was then replaced by the gp160 gene. This was accomplished by cloning the 2,600 bp NruI-NotI fragment of pH6HMNE, containing the entire HIV-1(MN) envelope (gp160) gene, into the 8,000 bp partial NruI-NotI fragment of pHIVGE16. The plasmid generated by this manipulation is called pHIVGE19.

pHIVGE19 was used in in vitro recombination experiments with vP866 (NYVAC) as the rescuing virus to yield vP1009.

Immunoprecipitation experiments with vP1009 infected cells were performed as described above for the expression of the HIV-1 gag precursor protein. No HIV-1-specific species were precipitated from mock infected or NYVAC infected Vero cells. Protein species corresponding to the env and gag precursor proteins, as well as various intermediate and mature gag cleavage products, were precipitated, however, from lysates of vP1009 infected cells.

EXAMPLE 26

GENERATION OF ALVAC/HIV-1 gag/pol AND env (GP120) RECOMBINANT

The sequence encoding the 5'-end of the gag gene was cloned between vaccinia virus tk flanking arms. This was accomplished by initially preparing plasmid pHIVGE15, as described above (see Example 24).

pHIVGE15 was used in recombination experiments with ALVAC (CPpp) as the rescuing virus to yield vCP117.

Immunoprecipitation analysis was performed as described above but with CEF cell monolayers to determine whether vCP117 expresses authentic HIV-1 gag and env gene products.

Lysates from the infected cells were analyzed for HIV gag and env gene expression using serum from HIV-1 seropositive individuals (obtained from New York State Department of Health). The sera was preadsorbed with ALVAC infected CEF cells. The preadsorbed sera was bound to Protein A-sepharose in an overnight incubation at 4° C. Following this incubation period, the material was washed 4×with 1×buffer A. Lysates precleared with normal human sera and protein A-sepharose were then incubated overnight at 4° C. with the HIV-1 seropositive human sera bound to protein A-sepharose. After the overnight incubation period, the samples were washed 4×with 1×buffer A and 2×with a LiCl$_2$/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV-1 seropositive individuals specifically precipitated the HIV-1 gag and env proteins from vCP117 infected cells, but did not precipitate HIV-1-specific proteins from mock infected or ALVAC infected cells.

EXAMPLE 27

GENERATION OF ALVAC/HIV-1 gag/pol AND env (gp160) RECOMBINANT

The sequence encoding the 5'-end of the gag gene was cloned between vaccinia virus tk flanking arms. This was accomplished by initially preparing plasmid pHIVGE15 as described above (see Example 24).

The gp120 gene was then replaced by the gp160 gene. This was accomplished by cloning the 2,600 bp NruI-NotI fragment of pH6HMNE, containing the entire HIV-1(MN) envelope (gp160) gene, into the 9,800 bp NruI-NotI fragment of pHIVGE15. The plasmid generated by this manipulation is called pHIVGE18.

The canary pox flanking arm deleted in the previous step was then cloned into pHIVGE18. This was accomplished by cloning the 1,500 bp NotI fragment of pHIVGE15, containing the C3 flanking arm, into the 12,400 bp NotI fragment of pHIVGE18. The plasmid generated by this manipulation is called pHIVGE20.

pHIVGE20 was used in recombination experiments with ALVAC (CPpp) as the rescuing virus to yield vCP130.

Immunoprecipitation analysis was performed with CEF cell monolayers as described above to determine whether vCP130 expresses authentic HIV-1 gag and env gene products.

Lysates from the infected cells were analyzed for HIV-1 gag and env gene expression using pooled serum from HIV-1 seropositive individuals (obtained from Chiron, Emeryville, Calif.). The sera was preadsorbed with ALVAC infected CEF cells. The preadsorbed sera was bound to Protein A-sepharose in an overnight incubation at 4° C. Following this incubation period, the material was washed 4×with 1×buffer A. Lysates precleared with normal human sera and protein A-sepharose were then incubated overnight at 4° C. with the HIV-1 seropositive human sera bound to protein A-sepharose. After the overnight incubation period, the samples were washed 4×with 1×buffer A and 2×with a LiCl$_2$/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography. Human sera from HIV-1 seropositive individuals specifically precipitated the HIV-1 gag and env proteins from vCP130 infected cells, but did not precipitate HIV-1-specific proteins from mock infected or ALVAC infected cells.

EXAMPLE 28

GENERATION OF ALVAC/HIV-1 gag/pol RECOMBINANT

A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by initially preparing plasmid pHIVG7 as described above (see Example 16).

The gag and pol genes were then cloned between canary pox flanking arms. This was accomplished by cloning the 4,400 bp SmaI-NotI fragment of pHIVG7, containing the I3L-promoted gag and pol genes, and the oligonucleotides, HIV2L6 (SEQ ID NO:131) (5'-GGCCAAAC-3') and HIV2L7 (SEQ ID NO:132) (5'-TCGAGTTT-3'), into the SmaI-XhoI site of pSPCP3L. The plasmid generated by this manipulation is called pHIVG24.

pHIVG24 was used in recombination experiments with ALVAC (CPpp) as the rescuing virus to yield vCP152.

Immunoprecipitation experiments with vCP152 infected cells were performed as described above for the expression of the HIV-1 env and gag proteins. No HIV-1-specific species were precipitated from mock infected or ALVAC infected cells. Protein species corresponding to the gag precursor protein, as well as various intermediate and mature gag cleavage products, were precipitated, however, from lysates of vCP152 infected cells.

EXAMPLE 29

GENERATION OF ALVAC/HIV-1 gag/pol AND env (TRUNCATED) RECOMBINANT

A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by initially preparing plasmid pHIVG24 as described above (see Example 28).

pHIVG24 was used in recombination experiments with vCP120 as the rescuing virus to yield vCP155.

Immunoprecipitation experiments with vCP155 infected cells were performed as described above for the expression of the HIV-1 env and gag proteins. No HIV-1-specific species were precipitated from mock infected cells. Protein species corresponding to the env and gag precursor proteins, as well as various intermediate and mature gag cleavage products, were precipitated, however, from lysates of vCP155 infected cells.

EXAMPLE 30

GENERATION OF ALVAC/HIV-1 gag/pol AND env (gp120 WITH TRANSMEMBRANE ANCHOR) RECOMBINANT A plasmid, pHXB2D, containing HIV-1 cDNA sequence was obtained from Dr. R. C. Gallo (NCI-NIH). The sequence encoding the 5'-end of the gag gene was cloned between vaccinia virus tk flanking arms. This was accomplished by initially preparing plasmid pHIVG24 as described above (see Example 28).

pHIVG24 was used in recombination experiments with vCP138 as the rescuing virus to yield vCP156.

Immunoprecipitation experiments with vCP156 infected cells were performed as described above for the expression of the HIV-1 env and gag proteins (CEF Cell monolayer). No HIV-1-specific species were precipitated from mock infected cells. Protein species corresponding to the env and gag precursor proteins, as well as various intermediate and mature cleavage products, were precipitated, however, from lysates of vCP156 infected cells.

Expression of HIV-1 gag-specific gene products either alone or in combination with env by vaccinia virus has been shown to lead to the production of non-infectious virus-like particles (Haffar et al., 1990; Hu et al., 1990). With this background it was investigated whether cells infected with ALVAC-based recombinant expressing HIV-1 gag-pol and env genes would also produce such particles. Furthermore, if these ALVAC-based recombinants were used to infect non-avian cells (i.e. Vero, MRC-5, etc.) then HIV-1 virus-like particles could be purified without any poxvirus virion contaminants.

To evaluate particle formation using Vero cells infected with vCP156, the following experiment was performed. Vero cells were infected at an m.o.i. of approximately 5 pfu/cell. After a 24 hr infection period, the supernatant was harvested and clarified by centrifugation at 2000 rpm for 10 min. The supernatant was then spun through filters which have a molecular weight cutoff of 30,000 kDa (Centricell 60, Polysciences, Inc., Warrington, Pa.). Thus, any smaller molecules would pass through these filters. The material retained by the filters was then analyzed by standard Western blot analysis (Maniatis et al., 1990) using pooled human serum from HIV-seropositive individuals (obtained from Dr. J. Conroy, New York State Department of Health). The results from the Western blot analysis demonstrated the presence of the major core protein p24 and the HIV-1(MN) anchored gp120 in the material retained by the filters. With the size exclusion noted above, the p24 would have passed through unless it was in a higher structural configuration (i.e. virus-like particles). Therefore, these results strongly suggest that HIV-1 virus-like particles containing the gp120 envelope component are produced in vCP156 infected cells.

EXAMPLE 31

EXPRESSION OF THE T1, T2, AND TH4.1 EPITOPES OF THE HIV-1 env GENE IN ALVAC AND NYVAC Recombinant poxviruses vP1062 and vCP146 were generated to express the T1, T2, and TH4.1 epitopes of HIV-1 env (Hosmalin et al., 1991) as individual peptides.

Construction of plasmid p731T1. Plasmid pMPI3H contains the vaccinia I3L early/intermediate promoter element (Schmitt and Stunnenberg, 1988; Vos and Stunnenberg, 1988) in a pUC8 background. The promoter element was synthesized by polymerase chain reaction (PCR) using pMPVC1, a subclone of vaccinia HindIII I, as template and synthetic oligonucleotides MPSYN283 (SEQ ID NO:133) (5'- CCCCCCAAGCTTACATCATGCAGTGGTTAAAC -3') and MPSYN287 (SEQ ID NO:134) (5'- GATTAAAC-CTAAATAATTGT -3') as primers. DNA from this reaction was cut with HindIII and RsaI and a 0.1 kb fragment containing the promoter element was purified. A linker region was assembled by annealing complementary synthetic oligonucleotides MPSYN398 (SEQ ID NO:135) (5'-ACAATTATTTAGGTTAACTGCA -3') and MPSYN399 (SEQ ID NO:136) (5'- GTTAACCTAAATAATTGT -3'). The PCR-derived promoter element and the polylinker region were ligated with vector plasmid PUC8 which had been cut with HindIII and PstI. The resulting plasmid, pMPI3H, contains the I3L promoter region from positions -100 through -6 relative to the initiation codon, followed by a polylinker region containing HpaI, PstI, SalI, BamHI, SmaI and EcoRI sites. Cleavage with HpaI produces blunt ended DNA linearized at position -6 in the promoter.

A cassette containing the T1 peptide driven by the vaccinia I3L promoter was generated by ligating complementary oligonucleotides T1C (SEQ ID NO:137) (5'-TAATCATGAAACAAATTATTAATATGTGGCAAGAA-GAGG- AAAAGCTATGTACGCTTGACT AGTTAAT-CACTCGAG -3') and T1N (SEQ ID NO:138) (5'- GATC-CTCGAGTGATTAACTAGTCAAGCGTA- CATAGCTTTTCCTACTTCTTGCCACATATT AATAATTTGTTTCATGATTA -3') to plasmid pMPI3H digested with HpaI and BamHI. This ligation reconstitutes the last 5 base pairs of the promoter, provides the complete coding sequence of the T1 peptide, and creates a XhoI site between the stop codon and BamHI site. This is plasmid p731T1. The sequence of the fragment was confirmed by nucleotide sequence analysis.

Construction of plasmid pH6T2. A cassette containing the T2 peptide driven by the vaccinia H6 promoter was generated in two steps: The H6 promoter through the EcoRV site was derived from a plasmid containing the synthetic H6 promoter (Perkus et al., 1989), using PCR and primers H6PCR1 (SEQ ID NO:157) and H6PCR2 (SEQ ID NO:205) (5'-TTAACGGATATCGCGATAATG-3') creating a 5' HindIII site. This 122 bp PCR-derived fragment was digested with HindIII and EcoRV followed by ligation to similarly digested pBS-SK+ (Stratagene, La Jolla, Calif.), generating plasmid pBSH6. Complementary oligonucleotides T2C (SEQ ID NO:139) (5'- ATCCGTTAAGTTTGTATCGTAAT-GCACGAAGATATTATTTCTTTGTGGGATCAATCTTTA AAATGACTAGTTAATCAG -3') and T2N (SEQ ID NO:140) (5'- GATCCTGATTAACTAGTCATTTTAAA-GATTGATCCCACAAAGAAATAATATCTTCGTGCA TTACGATACAAACTTAACGGAT -3') which complete the 3' end of the H6 promoter from the EcoRV site, encode the T2 peptide and create a BamHI site at the 3' end of the gene were annealed then ligated to pBSH6 that was digested with EcoRV and BamHI. This plasmid was designated pH6T2 following confirmation of the fragment by nucleotide sequence analysis.

Construction of plasmid pVQ42KTH4.1. A cassette containing the TH4.1 peptide driven by the AmEPV 42K promoter was generated by sequential PCR reactions: the 107 bp 42K promoter with 5' PstI and SmaI sites was derived by PCR from plasmid p42KRABI, a plasmid containing the gene for the rabies glycoprotein under control of the 42K promoter, using primers 42KVQ1 (SEQ ID NO:141) (5'-AATTAATTAGCTGCAGCCCCGGGT-CAAAAAAATATAAATG -3') and 42KVQ2 (SEQ ID NO:142) (5'- CCTTGTACTACTTCAATTACTC-TATCCATTTTATATTGTAATTATATATTTTC). The sequence of the 107 bp promoter region of this PCR-derived fragment is (SEQ ID NO:143) 5'-TCAAAAAAATATAAATGATTCACCATCT-GATAGAAAAAAATTTATTGGGAAGAATAT GATAATATTTTGGGATTTCAAAAT-TGAAAATATATAATTACAATATAAA -3'. The 159 bp PCR-derived fragment was fused to the coding sequences of TH4.1 with a second PCR using this fragment and synthetic oligonucleotides encoding the TH4.1 peptide TH41C (SEQ ID NO:144) (5'- ATGGATAGAGTAATTGAAGTAGTA-CAAGGAGCTTATAGAGCTATTAGATGACTAGTTAAT CACTCGAGGATCC -3') and TH41N (SEQ ID NO:145) (5'- GGATCCTCGAGTGATTAACTAGT-CATCTAATAGCTCTATAAGCTCCTTGTACTACTTCAA TTACTCTATCCAT -3') as template and primers 42KTH41 (SEQ ID NO:146) (5'- ATCATCGGATCCTCGAGTGAT-TAAACTAGTCATCTAATAGCTC -3') and 42KVQ1 (SEQ ID NO:141). This 210 bp PCR-derived fragment was extended in the 5' direction, incorporating a BamHI site at the 5' end using the fragment and synthetic oligonucleotides VQC (SEQ ID NO:147) (5'- TTAATCAGGATCCTTAAT-TAATTAGTTATTAGACAAGGTGAAAAC-GAAACTATTTGTAGC TTAATTAATTAGCTGCAGC-CCGGG -3') and VQN (SEQ ID NO:148) (5'-CCCGGGCTGCAGCTAATTAATTAAGCTA-CAAATAGTTTCGTTTTCACCTTGTCTAATAAC TAAT-TAATTAAGGATCCTGATTAA -3') as template for a third PCR using primers 42KTH41 (SEQ ID NO:146) and BAMVQ (SEQ ID NO:149) (5'- TTAATCAGGATCCT-TAATTAATTAGTTATTAGAC -3'). Subsequent nucleotide sequence analysis revealed an error in the sequence of oligonucleotide 42KTH41 (SEQ ID NO:146) such that an extra base (an A) was inserted after position 24 as indicated by the underline in the above sequence for 42KTH41. This was corrected with a final PCR employing the 272 bp fragment derived from the third PCR as template with primers BAMVQ (SEQ ID NO:149) and 42KTH41A (SEQ ID NO:150) (5'- ATCATCGGATCCTCGAGTGATTAAC-TAGTCATCTAATAGCTC -3'). After the final PCR, the cassette was to contain BamHI, PstI, and SmaI sites 5' to 42K-TH4.1 with XhoI and BamHI sites 3'. This 271 bp PCR-derived fragment was digested with BamHI and cloned into the BamHI site of pBS-SK+ (Stratagene, La Jolla, Calif.) generating plasmid pVQ42KTH4.1. Nucleotide sequence analysis of this plasmid confirmed that the sequence of the promoter and coding region was correct. However, a 3 bp deletion was revealed resulting in loss of the 3' BamHI site.

Construction of plasmid pT1T2TH4.1. These three cassettes were combined into a singular plasmid pT1T2TH4.1 such that I3L-T1 is opposite in orientation to the other two genes in the following manner: A 170 bp HindIII/XhoI fragment was isolated from p731T1 and ligated to similarly digested pH6T2 generating pT1T2. A 290 bp BamHI/SacI fragment from pVQ42KTH4.1 was ligated to similarly digested pT1T2, creating pT1T2TH4.1. The sequence of the insert was confirmed by nucleotide sequence analysis.

pC5LSP (defined in Example 14) was digested with EcoRI, treated with alkaline phosphatase and ligated to self-annealed oligonucleotide CP29 (SEQ ID NO:151) (5'-AATTGCGGCCGC-3'), digested with NotI and linear purified followed by self-ligation. This procedure introduced a NotI site to pC5LSP, generating pNC5LSP5.

Plasmid pSD550 was derived from pSD548 as follows. Plasmid pSD548 (Tartaglia et al., 1992) is a vaccinia vector plasmid in which the I4L ORF (Goebel et al., 1990a,b) is replaced by a cloning region consisting of BglII and SmaI sites. To expand the multicloning region, pSD548 was cut with BglII and SmaI and ligated with annealed complementary synthetic oligonucleotides 539A (SEQ ID NO:152) (5'-AGAAAATCAGTTAGCTAAGATCTC-CCGGGCTCGAGGGTACCGGATCCTGATT-AGTTAATTTTTG T-3') AND 539B (SEQ ID NO:153) (5'-GATCACAAAAATTAACTAATCAGGATCCGG-TACCCTCGAGCCCGGGAGATCTTAGCTAACTGATT TTTCT-3'). In the resulting plasmid, pSD550, the multicloning region contains BglII, SmaI, XhoI, KpnI and BamHI restriction sites.

The 602 bp XhoI fragment from pT1T2TH4.1 containing the genes for the epitopes driven by their respective promoters was cloned into donor plasmids pNC5LSP5 and pSD550 in their XhoI sites. Nucleotide sequence analysis was used to confirm the sequence and the orientation of the insert. The resulting plasmids pC5T1T2TH4.1 and pI4T1T2TH4.1 were used in in vitro recombination experiments with ALVAC and NYVAC to generate recombinant viruses vCP146 and vP1062, respectively. These recombinant viruses were demonstrated to contain the desired genes by hybridization of a specific DNA probe to viral plaques.

EXAMPLE 32

EXPRESSION OF TWO FUSION PEPTIDES CONTAINING THE T1, T2, AND TH4.1 EPITOPES OF HIV-1 env WITH AND WITHOUT A TRANSMEMBRANE ANCHOR DOMAIN FROM HIV-1 env Recombinant poxviruses vP1060, vP1061, vCP154 and vCP148 were created to express a fusion peptide consisting of the signal sequences from HIV-1 env coupled to sequences corresponding to the T1, T2, and TH4.1 epitopes of HIV-1 env by cleavable linker regions. vP1060 and vCP154 differ from vP1061 and vCP148 in that the former recombinant viruses express the fusion peptide along with sequences corresponding to the transmembrane region of HIV-1 env.

Both fusion peptides include the 51 amino acid N-terminal portion of HIV-1 (IIIB) env, residues 1–50 (plus initiating Met) based on Ratner et al. (1985). The amino acid sequence of this signal region (SEQ ID NO:154) is MKEQKTVAMRVKEKYQHLWRWGWRWGTMLLGMLMICSATEKLWVTVYYGVP. This is followed by the T1, T2, and TH4.1 epitopes (Hosmalin et al., 1991) separated from the signal, each other, and anchor sequence where present, by a cleavable linker region up to 5 amino acids in length. The amino acid sequence of this region of the peptide (SEQ ID NO:155) is [signal]-PFRKQIINMWQEVGKAMYA-PPFRK-HEDIISLWDQSLK-PPFRK-DRVIEVVQGAYRAIR-[PPFRK-anchor]. The anchor domain is a 28 amino acid transmembrane region of HIV-1 (IIIB) env, residues 691–718. The amino acid sequence of this region (SEQ ID NO:156) is LFIMIVGGLVGLRIVFAVLSVVNRVRQG-[stop].

For both versions of the fusion peptide, the H6 promoter and HIV-1 env signal sequences were derived by PCR from plasmid pBSH6HIV3B5P (defined in Example 2) using primers H6PCR1 (SEQ ID NO:157) (5'ACTACTAAGCTTCTTTATTCTATACTTAAAAAGTG-3') and PCRSIGT1 (SEQ ID NO:158) (5'- CATATTAATTTGTTTTCTAAAGGAGGTACCCCATAATAGACTGTG -3'). This 314 bp PCR-derived fragment consists of a 5' HindIII site followed by the H6 promoter and coding sequences for the signal, linker, and the first 6 amino acids of the T1 peptide.

The remainder of the coding region for the construct without the transmembrane region was generated by PCR amplification of oligonucleotides T2T4A (SEQ ID NO:159) (5'- GCTCCTCCTTTTAGAAAACACGAAGATATTATTTCTTTGTGGGATCAATCTTTAAAACCT CCTTTTAGAAAAGATAGAGTAATTGAAGTAGTAC -3') and T2T4B (SEQ ID NO:160) (5'- GTACTACTTCAATTACTCTATCTTTTCTAAAAGGAGGTTTTAAAGATTGATCCCACAAAG AAATAATATCTTCGTGTTTTCTAAAAGGAGGAGC -3') using primers PCRT1T2 (SEQ ID NO:161) (5'- AAACAAATTATTAATATGTGGCAAGAAGTAGGAAAAGCTATGTACGCTCCTCCTTTTAGA AAACACGAAG -3') and PCRT4END (SEQ ID NO:162) (5'- ACTACTTCTAGATTATCTAATAGCTCTATAAGCTCCTTGTACTACTTCAATTACTC -3'). This 177 bp PCR-derived fragment encodes the T1 peptide, a linker region, the T2 peptide, another linker region, and the TH4.1 peptide, followed by a 3' XbaI site. This fragment was fused with the 314 bp PCR-derived fragment containing the promoter and signal sequences by PCR with primers H6PCR1 (SEQ ID NO:157) and PCRT4END (SEQ ID NO:162). Following digestion of this 473 bp PCR-derived fragment with HindIII and XbaI a fragment of 455 bp was isolated from an agarose gel, ligated to similarly digested PBS-SK, and the sequence of the insert verified by nucleotide sequence analysis. The resulting plasmid was designated pBST1T2TH4.1.

The remainder of the coding region of the version with the transmembrane anchor was generated by PCR amplification of oligonucleotides, T2T4A (SEQ ID NO:159) and T2T4B (SEQ ID NO:160), using primers PCRT1T2 (SEQ ID NO:161) and PCRT4TM (SEQ ID NO:163) (5'- TACTATCATTATGAATAATTTTCTAAAAGGAGGTCTAATAGCTCTATAAGCTCCTTGTAC TACTTCAATTACTC -3'), altering the 3' end to accommodate the transmembrane region. This 195 bp PCR-derived fragment was fused by PCR with oligonucleotides comprising the anchor, HIVTM1 (SEQ ID NO:107) and HIVTM2 (SEQ ID NO:108) using primers PCRT1T2 (SEQ ID NO:161) and PCRT4END (SEQ ID NO:162). This 276 bp PCR-derived fragment was fused with the 314 bp PCR-derived fragment containing the promoter and signal sequences by PCR with primers H6PCR1 (SEQ ID NO:157) and PCRT4END (SEQ ID NO:162). Following digestion of this 572 bp PCR-derived fragment with HindIII and XbaI a fragment of 554 bp was isolated from an agarose gel, ligated to similarly digested pBS, and the sequence of the insert verified by nucleotide sequence analysis. The resulting plasmid was designated pBST1T2TH4.1A.

pC5LSP (defined in Example 14) was digested with BamHI and ligated to annealed oligonucleotides CP32 (SEQ ID NO:112) and CP33 (SEQ ID NO:113) to generate pVQC5LSP6. pVQC5LSP6 was digested with EcoRI, treated with alkaline phosphatase and ligated to self-annealed oligonucleotide CP29 (SEQ ID NO:151), digested with NotI and linear purified followed by self-ligation. This procedure introduced a NotI site to pVQC5LSP6, generating pNVQC5LSP7.

Both cassettes were placed individually between the XhoI and XbaI sites of insertion plasmid pNVQC5LSP7. These plasmids pC5ST1T1TH4.1 and pC5ST1T2TH4.1A were used to generate canarypoxvirus recombinants, vCP148 and vCP154 respectively. BamHI-SmaI fragments were excised from pC5ST1T1TH4.1 and pC5ST1T2TH4.1A and ligated to similarly digested pSD550 (defined in Example 31) generating plasmids pI4ST1T2TH4.1 and pI4ST1T1TH4.1A, respectively. These plasmids were used in recombination experiments with NYVAC as the rescuing virus resulting in recombinants vP1061 and vP1060, respectively. These recombinant viruses were demonstrated to contain the desired genes by hybridization of a specific DNA probe to viral plaques.

EXAMPLE 33

EXPRESSION OF THE HIV-1 nef GENE IN ALVAC, TROVAC, AND NYVAC

Recombinant poxviruses vP1084, vFP174, and vCP168 were generated expressing HIV-1 nef (MN) as follows:

The I3L promoter was derived by PCR from plasmid pMPI3H using primers I3PCR1 (SEQ ID NO:164) (5'- ATCATCGGATCCAAGCTTACATCATGCAGTGG -3') and PI3NEF2 (SEQ ID NO: 165) (5'- CGTTTTGACCATTTGCCACCCATGATTAAACCTAAATAATTGTACTTTG -3'). The coding region of nef was generated by PCR amplification of pMN1.8–10 (a clone of that portion of the MN genome between SstI sites at 7792 and 9595) using primers PI3NEF1 (SEQ ID NO:166) (5'- AGTACAATTATTTAGGTTTAATCATGGGTGGCAAATGGTCAAAACG -3') and PNEFBAM (SEQ ID NO:167) (5'- ATCATCGGATCCTAACACTTCTCTCTCCGG -3'). Fusion of the coding region with the promoter was accomplished by amplification of the previous PCR products using primers I3PCR1 (SEQ ID NO:164) and PNEFBAM (SEQ ID NO:167). Following digestion of this product with BamHI a fragment of 0.7 kb was isolated from an agarose gel and ligated to similarly digested pBS-SK+ (Stratagene, La Jolla, Calif.), generating plasmid pI3NEF. It was at this point that sequence deviations were first observed. The sequence of the cassette was determined to differ from the published sequence (Gurgo et al., 1988, GenBank Accession Number M17449) due to deviations in plasmid pMN1.8–10 (provided by Dr. R. C. Gallo, NCI-NIH). These differences are summarized below relative to the published sequence.

| Base # | Gurgo et al. | MN1.8-10 | Result | Cassette |
| --- | --- | --- | --- | --- |
| 8834 | T | T | silent | C (aa = Arg) |
| 8863 | G | A | Lys->Arg | A (aa = Lys) |
| 8890 | T | C | Pro->Leu | C (aa = Pro) |
| 9028 | A | G | Arg->Lys | G (aa = Arg) |
| 9127 | A | A | silent | G (aa = Gln) |
| 9330–9331 | GG | GGG | frameshift | GG |

The two silent mutations in the cassette (at positions 8834 and 9127) were apparently errors in PCR. Since there is no effect on the encoded protein, the se were allowed to persist. The frameshift at 9930 results in a lengthened open reading frame more closely resembling other HIV-1 isolates. In keeping with the published size of nef from the MN isolate, this cassette required a fourth PCR to generate the truncated 3' end of the coding region.

Removal of the extra base at position 9930 was accomplished by PCR amplification of the insert in pI3NEF with primers I3PCR1 (SEQ ID NO:164) and PNEFFIX1 (SEQ ID NO:168) (5'- ATCATCGGATCCTAACACTTCTCTCTC-CGGGTCATCCATCCATGCTGGCTCATAG -3') Following digestion of this 678 bp PCR-derived fragment with BamHI a fragment of 660 bp was isolated from an agarose gel and ligated to similarly digested pBS. generating plasmid pBSI3NEF. The insert was verified by nucleotide sequence analysis.

The 660 bp BamHI fragment from pBSI3NEF containing the nef gene was placed in the BamHI site of insertion plasmid PNVQC5LSP7 (defined in Example 32). The resulting plasmid pC5I3NEF was employed in a recombination into the C5 locus of ALVAC, generating the recombinant vCP168. The same 660 bp BamHI fragment was also placed in the BamHI site of insertion plasmid pSD550 (defined in Example 31), creating plasmid pI4I3NEF. A recombination with this plasmid with NYVAC generated recombinant vP1084.

An insertion plasmid for the F16 locos of TROVAC was derived in the following manner. A 7.3 kb NaeI/NdeI fragment was isolated from a plasmid containing the 10.5 kb HindIII fragment of fowlpox virus described by Tartaglia et al. (1990) and ligated to similarly digested pUC9 creating plasmid pRW866.

pUC9 was digested with PvuII and an EcoRI linker ligated between the PvuII sites creating plasmid pRW715. A cloning site flanked by fowlpox sequences was generated by PCR amplification of a portion of the 10.5 kb fragment with primers RW264 (SEQ ID NO:169) (5'- AATTAACCCGG-GATCCAAGCTTCTAGCTAGCTAATTTT-TATAGCGGCCGCTATAATCGTT AACTTATTAG -3') and RW267 (SEQ ID NO:170) (5'- GCTAGAAATCTCT-TAGTTTTTATAGTTG -3'). An adjacent region was also amplified by PCR using primers RW266 (SEQ ID NO:171) (5'- GTTACATATGTACAGAATCTGATCATAG -3') and RW265 (SEQ ID NO:172) (5'- CTAGCTAGAAGCTTG-GATCCCGGGTTAATTAAT-TAATAAAAAGCGGCCGCGTTAAAGTAG AAAAATG -3'). These PCR-derived fragments were fused by a third PCR using primers RW266 (SEQ ID NO:171) and RW267 (SEQ ID NO:170). The resulting PCR-derived fragment consisted of fowlpox sequences flanked by a 5' EcoRI site and a 3' NdeI site. Central in the fragment is a polycloning region containing SmaI, BamHI, and HindIII sites, flanked by NotI sites and translation stop codons in six reading frames. An early transcription termination signal (Yuen and Moss, 1987) is adjacent to the 3' NotI site. This PCR-derived fragment, digested with EcoRI and NdeI, was ligated to similarly digested pRW715 creating plasmid pRW864. An 11K promoted lac Z gene was excised from pAM1 by partial BamHI, total PstI digestion. This fragment was made blunt ended with Klenow polymerase and ligated to SmaI digested pRW864, creating pRW867A. The NotI fragment from pRW867A was made blunt ended with Klenow polymerase in the presence of dNTPs so that the NotI sites would be regenerated when ligated into an FspI site, and ligated to pRW866 which was partially digested with FspI such that the insertion was made corresponding to position 1955 described by Tartaglia et al. (1990). The resulting plasmid, pRW868, was then digested with NotI to remove the lac Z cassette, and ligated to the 66 bp polylinker from pRW864 which was excised by NotI digestion. The resulting plasmid was designated pRW673. An 81 bp SmaI fragment was derived from pVQ42KTH4.1 (defined in Example 31) and inserted into SmaI digested pRW873 generating plasmid pVQ873.

The nef cassette was excised from pBSI3NEF as a 684 bp HindIII fragment for insertion into pVQ873 followed by recombination into the F16 locus of TROVAC to generate vFP174.

EXAMPLE 34

EXPRESSION OF HIV-2 GENES IN NYVAC

Generation of NYVAC/HIV2 gag/pol recombinant. A plasmid, PISSYEGP, containing the human immunodeficiency virus type 2 (HIV2) gag and pol genes was obtained from Dr. G. Franchini (NCI-NIH). The gag and pol genes from this plasmid were cloned downstream of the I3L promoter and between vaccinia virus tk flanking arms. This was accomplished by cloning the 4,400 bp BstUI-BglII fragment of pISSYEGP, containing the HIV2 gag and pol genes, and the oligonucleotides, SIVL1 (SEQ ID NO:69) and HIV2L1 (SEQ ID NO:173) (5'-CGCCCATGATTAAACCTAAATAATTGTACTTTGTAATATAATGATATATATTTTCACTTTATCTC AC-3'), containing the I3L promoter, into the 4,070 bp XhoI-BglII fragment of pSD542 (defined in Example 15). The plasmid generated by this manipulation is called pHIV21.

Extraneous 3'-noncoding sequence was then eliminated. This was accomplished by cloning a 280 bp BclI-SmaI PCR fragment, containing the 3'-end of the pol gene, into the 8,100 bp BclI-SmaI fragment of pHIV21. This PCR fragment was generated from the plasmid, pISSYEGP, with the oligonucleotides, HIV2P2 (SEQ ID NO:174) (5'-ATGGCAGTTCATTGCAT-3') and HIV2P3 (SEQ ID NO:175) (5'-TTCCCGGGAGATCTCTATGCCATTTCTCCAT-3'). The plasmid generated by this manipulation is called pHIV22.

pHIV22 was used in recombination experiments with NYVAC (vP866) as the rescuing virus to yield vP1045.

Immunoprecipitation analysis was performed to determine whether vP1045 expresses authentic HIV2 gag gene products.

Lysates from the infected cells were analyzed for HIV2 gag expression using pooled serum from HIV2 seropositive individuals (obtained from Dr. G. Franchini (NCI-NIH)). The sera was preadsorbed with vP866 infected Vero cells. The preadsorbed sera was bound to Protein A-sepharose in an overnight incubation at 4° C. Following this incubation period, the material was washed 4×with 1×buffer A. Lysates precleared with normal human sera and protein A-sepharose were then incubated overnight at 4° C. with the HIV2 seropositive human sera bound to protein A-sepharose. After the overnight incubation period, the samples were washed 4×with 1×buffer A and 2×with a LiCl$_2$/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV2 seropositive individuals specifically precipitated the HIV2 gag precursor protein, as well as various intermediate and mature gag cleavage protein products, from vP1045 infected cells, but did not precipitate HIV2-specific proteins from mock infected or NYVAC infected cells.

EXAMPLE 35

GENERATION OF NYVAC/HIV2 gag/pol AND env (gp160) RECOMBINANT

A plasmid, pISSYEGP, containing the HIV2 gag and pol genes was obtained from Dr. G. Franchini (NCI-NIH). The gag and pol genes from this plasmid were cloned downstream of the I3L promoter and between vaccinia virus tk flanking arms. This was accomplished by initially preparing plasmid pHIV22 as described above (see Example 34).

pHIV22 was used in recombination experiments with vP920 as the rescuing virus to yield vP1047.

Immunoprecipitation experiments with vP1047 infected cells were performed as described above for the expression of the HIV2 gag proteins. No HIV2-specific species were precipitated from mock infected cells. Protein species corresponding to the HIV2 env and gag precursor proteins, as well as various intermediate and mature gag cleavage products, were precipitated, however, from lysates of vP1047 infected cells.

EXAMPLE 36

GENERATION OF NYVAC/HIV2 gag/pol AND env (gp120) RECOMBINANT

A plasmid, pISSYEGP, containing the HIV2 gag and pol genes was obtained from Dr. G. Franchini (NCI-NIH). The gag and pol genes from this plasmid were cloned downstream of the I3L promoter and between vaccinia virus tk flanking arms. This was accomplished by initially preparing plasmid pHIV22 as described above (see Example 34).

pHIV22 was used in recombination experiments with vP922 as the rescuing virus to yield vP1044.

Immunoprecipitation experiments with vP1044 infected cells were performed as described above for the expression of the HIV2 gag proteins. No HIV2-specific species were precipitated from mock infected cells. Protein species corresponding to the HIV2 env and gag precursor proteins, as well as various intermediate and mature gag cleavage products, were precipitated, however, from lysates of vP1044 infected cells.

EXAMPLE 37

EXPRESSION OF HIV2 GENES IN ALVAC

Generation of ALVAC/HIV2 gag/pol and env (gp160) recombinant. The plasmid, pBSH6HIV2ENV (defined in Example 4), contains the H6-promoted HIV2 env (gp160) gene. The H6-promoted env gene from this plasmid was cloned between canary pox flanking arms. This was accomplished by cloning the 2,700 bp XhoI-SacII fragment of pBSH6HIV2ENV, containing the H6-promoted env gene, and the oligonucleotides, HIV2L4 (SEQ ID NO:176) (5'-GGTTG-3') and HIV2L5 (SEQ ID NO:177) (5'-AATTCAACCGC-3'), into the XhoI-EcoRI site of pC6L (defined in Example 50). The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

pHIV25 was used in recombination experiments with ALVAC (CPpp) as the rescuing virus to yield vCP153.

Immunoprecipitation analysis was performed as described above, but with CEF cell monolayers to determine whether vCP153 expresses authentic HIV2 gag and env gene products.

Lysates from the infected cells were analyzed for HIV2 gag and env gene expression using pooled serum from HIV2 seropositive individuals (obtained from Dr. G. Franchini (NCI-NIH)). The sera was preadsorbed with ALVAC infected CEF cells. The preadsorbed sera was bound to Protein A-sepharose in an overnight incubation at 4° C. Following this incubation period, the material was washed 4×with 1×buffer A. Lysates precleared with normal human sera and protein A-sepharose were then incubated overnight at 4° C. with the HIV2 seropositive human sera bound to protein A-sepharose. After the overnight incubation period, the samples were washed 4×with 1×buffer A and 2×with a LiCl$_2$/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Human sera from HIV2 seropositive individuals specifically precipitated the HIV2 env and gag precursor proteins, as well as various intermediate and mature gag cleavage products, from vCP153 infected cells, but did not precipitate HIV2-specific proteins from mock infected or ALVAC infected cells.

EXAMPLE 38

EXPRESSION OF SIV GENES IN NYVAC GENERATION OF NYVAC/SIV env (gp120-gp28) AND gag (PROTEASE$^-$) RECOMBINANT Immunoprecipitation analysis was performed to determine whether vP948 (defined in Example 5) expresses authentic SIV env and gag precursor proteins.

Lysates from the infected cells were analyzed for SIV env and gag precursor expression using serum from SIV seropositive macaques (obtained from Dr. G. Franchini (NCI-NIH)). The sera was preadsorbed with NYVAC (vP866) infected Vero cells. The preadsorbed sera was bound to Protein A-sepharose in an overnight incubation at 4° C. Following this incubation period, the material was washed 4×with 1×buffer A. Lysates precleared with normal macaque sera and protein A-sepharose were then incubated overnight at 4° C. with the SIV seropositive macaque sera bound to protein A-sepharose. After the overnight incubation period, the samples were washed 4×with 1×buffer A and 2×with a LiCl$_2$/urea buffer. Precipitated proteins were dissociated from the immune complexes by the addition of 2×Laemmli's buffer (125 mM Tris (pH6.8), 4% SDS, 20% glycerol, 10% 2-mercaptoethanol) and boiling for 5 min. Proteins were fractionated on a 10% Dreyfuss gel system (Dreyfuss et al., 1984), fixed and treated with 1M Na-salicylate for fluorography.

Macaque sera from SIV seropositive individuals specifically precipitated the SIV gag precursor protein and the envelope glycoprotein from vP948 infected cells, but did not precipitate SIV-specific proteins from mock infected cells.

EXAMPLE 39

GENERATION OF NYVAC/SIV gag/pol RECOMBINANT

A plasmid, pSIVGAGSS11G, containing SIV$_{MAC142}$ cDNA sequence was obtained from Dr. G. Franchini (NCI-NIH). The gag and pol genes from this plasmid were cloned downstream of the I3L promoter and between vaccinia virus tk flanking arms. This was accomplished by preparing plasmid pSIVG5 as described above (see Example 5).

pSIVG5 was used in recombination experiments with NYVAC (vP866) as the rescuing virus to yield vP1042.

Immunoprecipitation experiments with vP1042 infected cells were performed as described above for the expression of the SIV env and gag precursor proteins. No SIV-specific species were precipitated from mock infected or NYVAC infected Vero cells. Protein species corresponding to the gag precursor protein, as well as various intermediate and mature gag cleavage products, were precipitated, however, from lysates of vP1042 infected cells.

EXAMPLE 40

GENERATION OF NYVAC/SIV gag/pol AND env (gp120-gp41) RECOMBINANT pSIVG5 (Example 5) was used in recombination experiments with vP1050as the rescuing virus to yield vP1071.

Immunoprecipitation experiments with vP1071 infected cells show expression of SIV genes.

EXAMPLE 41

GENERATION OF NYVAC/SIV gag/pol AND env (gp120-gp28) RECOMBINANT pSIVG5 (Example 5) was used in recombination experiments with vP874 as the rescuing virus to yield vP943.

Immunoprecipitation experiments with vP943 infected cells were performed as described above for the expression of the SIV env and gag precursor proteins. No SIV-specific species were precipitated from mock infected Vero cells. Protein species corresponding to the env and gag precursor proteins, as well as various intermediate and mature gag cleavage products, were precipitated, however, from lysates of vP943 infected cells.

EXAMPLE 42

GENERATION OF NYVAC/SIV p16, p28 RECOMBINANT

Immunoprecipitation experiments with vP942 (Example 5) infected cells were performed as described above for the expression of the SIV env and gag precursor proteins. No SIV-specific species were precipitated from mock infected Vero cells. Protein species corresponding to p16 and p28 were precipitated, however, from lysates of vP942 infected cells.

EXAMPLE 43

GENERATION OF NYVAC/SIV p16, p28 AND env (gp120-gp28) RECOMBINANT

Immunoprecipitation experiments with vP952 (Example 5) infected cells were performed as described above for the expression of the SIV env and gag precursor proteins. No SIV-specific species were precipitated from mock infected Vero cells. Protein species corresponding to env and p16 and p28 were precipitated, however, from lysates of vP952 infected cells.

EXAMPLE 44

GENERATION OF NYVAC/SIV env (gp120-gp41) RECOMBINANT

The plasmid, pSIVEMVC, contains the H6-promoted SIV$_{MAC142}$ envelope gene (in vitro selected truncated version). The region of the envelope gene containing the premature termination codon was cloned into pBSK+. This was accomplished by cloning the 1,120 bp ClaI-BamHI fragment of pSIVEMVC into the ClaI-BamHI site of pBSK+. The plasmid generated by this manipulation is called pSIV10.

The upstream termination codon, TAG, was then changed to the original CAG codon. This was accomplished by cloning the oligonucleotides, SIVL20 (SEQ ID NO:178) (5'-CTAGCTAAGTTAAGGCAGGGGTATAGGC-CAGTGTTCTCTTCCCCACCCTCT-TATTTCCAGCAGAC TCATACCCAACAG-3') and SIVL21 (SEQ ID NO:179) (5'-GTCCTGTTGGGTATGAGTCTGCTG-GAAATAAGAGGGTGGGGAAGAGAA-CACTGGCCTATACCCCT GCCTTAACTTAG-3'), into the 4,000 bp NheI-PpuMI fragment of pSIV10. The plasmid generated by this manipulation is called pSIV11.

The region containing the modified codon was then cloned back into pSIVEMVC. This was accomplished by cloning the 380 bp BglII-NheI fragment of pSIV11, containing the modified codon, into the 5,600 bp partial BglII-NheI fragment of pSIVEMVC. The plasmid generated by this manipulation is called pSIV12.

pSIV12 was used in in vitro recombination experiments with NYVAC (vP866) as the rescuing virus to yield vP1050.

Immunoprecipitation experiments with vP1050 infected cells were performed as described above for the expression of the SIV env and gag precursor proteins. No SIV-specific species were precipitated from mock infected or NYVAC infected Vero cells. A protein species corresponding to env was precipitated, however, from lysates of vP1050 infected cells.

EXAMPLE 45

EXPRESSION OF SIV GENES IN ALVAC

Generation of ALVAC/SIV gag/pol recombinant. A plasmid, pSIVGAGSS11G, containing SIV$_{MAC}$142 cDNA sequence was obtained from Dr. G. Franchini (NCI-NIH).

The gag and pol genes from this plasmid were cloned downstream of the I3L promoter and between vaccinia virus flanking arms. This was accomplished by initially preparing plasmid pSIVG5 as described above (see Example 5).

The gag/pol genes were then cloned between canary pox flanking arms. This was accomplished by cloning the 4,500 bp SmaI-NotI fragment of pSIVG5, containing the I3L-promoted gag/pol genes, into the SmaI-NotI site of pC5L (defined in Example 10). The plasmid generated by this manipulation is called pSIVGC13.

pSIVGC13 was used in recombination experiments with ALVAC (CPpp) as the rescuing virus to yield vCP172.

Immunoprecipitation experiments with vCP172 infected cells show expression of SIV genes.

EXAMPLE 46

EXPRESSION OF SIV GENES IN ALVAC

Generation of ALVAC/SIV env (gp120-gp41) and gag/pol Recombinant. A plasmid, pSIVGAGSS11G, containing simian immunodeficiency virus ($SIV_{mac142}$) cDNA sequence was obtained from Genoveffa Franchini (NCI-NIH). The gag/pol genes from this plasmid were cloned downstream of the I3L promoter and between vaccinia virus flanking arms. This was accomplished by cloning the 4,800 bp CfoI-TagI fragment of pSIVGAGSS11G, containing the gag/pol genes, and the oligonucleotides, SIVL1 (SEQ ID NO:69) and SIVL2 (SEQ ID NO:70), encoding the vaccinia virus I3L promoter, into the 4,070 bp XhoI-AccI fragment of pSD542VCVQ. The plasmid generated by this manipulation is called pSIVG1.

Extraneous 3'-noncoding sequence was then eliminated. This was accomplished by cloning a 1,000 bp BamHI-HpaI PCR fragment, containing the 3'-end of the pol gene, into the 7,400 bp partial BamHI-HpaI fragment of pSIVG1. (This PCR fragment was generated from the plasmid, pSIVGAGSS11G, with the oligonucleotides, SIVP5 (SEQ ID NO:71) and SIVP6 (SEQ ID NO:72)). The plasmid generated by this manipulation is called pSIVG4.

Sequencing analysis revealed that pSIVG4 contains a single base pair deletion within the pol gene. To correct this error the 2,320 bp BglII-StuI fragment of pSIVG1 was cloned into the 6,100 bp partial BglII-StuI fragment of pSIVG4. The plasmid generated by this manipulation is called pSIVG5.

The gag/pol genes were then cloned between canary pox flanking arms. This was accomplished by cloning the 4,500 bp SmaI-NotI fragment of pSIVG5, containing the I3L-promoted gag/pol genes, into the SmaI-NotI site of pC5L. The plasmid generated by this manipulation is called pSIVGC13.

The SIV env gene was then cloned into pSIVGC13. This was accomplished by cloning the E. coli DNA polymerase I (Klenow fragment) filled-in 2,750 bp partial BglII-XhoI fragment of pSIV12, containing the H6-promoted SIV env gene, into the SmaI site of pSIVGC13. The plasmid generated by this manipulation is called pSIVGC14.

pSIVGC14 is used in in vitro recombination experiments with ALVAC as the rescuing virus.

Generation of ALVAC/SIV env (gp120-gp41) Recombinant. A plasmid, pSIVEMVC, contains the H6-promoted simian immunodeficiency virus envelope gene (in vitro selected truncated version). The region of the envelope gene containing the premature termination codon was cloned into pBSK+. This was accomplished by cloning the 1,120 bp ClaI-BamHI fragment of pSIVEMVC into the ClaI-BamHI site of pBSK+. The plasmid generated by this manipulation is called pSIV10.

The upstream termination codon, TAG, was then changed to the original CAG codon. This was accomplished by cloning the oligonucleotides, SIVL20 (SEQ ID NO:178) and SIVL21 (SEQ ID NO:179), into the 4,000 bp NheI-PpuMI fragment of pSIV10. The plasmid generated by this manipulation is called pSIV11.

The region containing the modified codon was then cloned back into pSIVEMVC. This was accomplished by cloning the 380 bp BglII-NheI fragment of pSIV11 into the 5,600 bp partial BglII-NheI fragment of pSIVEMVC. The plasmid generated by this manipulation is called pSIV12.

The env gene was then cloned between canary pox flanking arms. This was accomplished by cloning the 2,700 bp NruI-Asp718 fragment of pSIV12, containing the H6-promoted env gene, into the 7,400 bp NruI-Asp718 fragment of pNVQH6C5SLP18. The plasmid generated by this manipulation is called pSIVGC15.

pSIVGC15 is used in in vitro recombination experiments with ALVAC as the rescuing virus.

EXAMPLE 47

GENERATION OF HIV1 GENES IN ALVAC

Generation of ALVAC/HIV1 gag (+pro) (IIIB) and gp120 (+transmembrane) (MN) Recombinant. A plasmid, pHXB2D, containing human immunodeficiency virus type 1 (HIV1) cDNA sequence (IIIB) was obtained from Dr. R. C. Gallo (NCI-NIH). The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542VCVQ. The plasmid generated by this manipulation is called pHIVG2.

The 3'-end of the gag gene was then cloned into pHIVG2. This was accomplished by cloning a 280 bp ApaI-BamHI PCR fragment, containing the 3'-end of the gag gene, into the 5,620 bp ApaI-BamHI fragment of pHIVG2. (This PCR fragment was generated from the plasmid, pHXB2D, with the oligonucleotides, HIVP5 (SEQ ID NO:116) and HIVP6 (SEQ ID NO:117)). The plasmid generated by this manipulation is called pHIVG3.

The I3L promoter was then cloned upstream of the gag gene. This was accomplished by cloning the oligonucleotides, HIVL17 (SEQ ID NO:118) and HIVL18 (SEQ ID NO:119), encoding the vaccinia virus I3L promoter and the 5'-end of the gag gene, into the 5,540 bp partial BglII-ClaI fragment of pHIVG3. The plasmid generated by this manipulation is called pHIVG4.

The portion of the gag gene encoding p24, p2, p7 and p6 was then eliminated. This was accomplished by cloning the oligonucleotides, HIVL19 (SEQ ID NO:120) and HIVL20 (SEQ ID NO:121), into the 4,450 bp partial PvuII-BamHI fragment of pHIVG4. The plasmid generated by this manipulation is called pHIVG5.

The remainder of the gag gene, as well as the pol gene, was then cloned downstream of the p17 "gene". This was accomplished by cloning the 4,955 bp ClaI-SalI fragment of pHXB2D, containing most of the gag gene and all of the pol gene, into the 4,150 bp ClaI-SalI fragment of pHIVG5. The plasmid generated by this manipulation is called pHIVG6.

Extraneous 3'-noncoding sequence was then eliminated. This was accomplished by cloning a 360 bp AflII-BamHI PCR fragment, containing the 3'-end of the pol gene, into the 8,030 bp AflII-BamHI fragment of pHIVG6. (This PCR fragment was generated from the plasmid, pHXB2D, with the oligonucleotides, HIVP7 (SEQ ID NO:122) and HIVP8 (SEQ ID NO:123)). The plasmid generated by this manipulation is called pHIVG7.

The I3L-promoted gag and pol genes were then inserted into a canary pox insertion vector. This was accomplished by cloning the 4,360 bp partial BglII-BamHI fragment of pHIVG7, containing the I3L-promoted gag and pol genes, into the BamHI site of pVQH6CP3L. The plasmid generated by this manipulation is called pHIVGE14.

The H6-promoted HIV1 gp120 (+transmembrane) gene was then cloned into pHIVGE14. This was accomplished by cloning the 1,700 bp NruI-SmaI fragment of pC5HIVMN120T, containing the gp120 (+transmembrane) gene, into the 11,400 bp NruI-SmaI fragment of pHIVGE14. The resulting plasmid is called pHIVGE14T.

Most of the pol gene was then removed. This was accomplished by cloning a 540 bp ApaI-BamHI PCR fragment, containing the 3'-end of the HIV1 protease "gene", into the 10,000 bp ApaI-BamHI fragment of pHIVGE14T. (This PCR fragment was generated from the plasmid, pHIVG7, with the oligonucleotides, HIVP5 (SEQ ID NO:116) and HIVP37 (SEQ ID NO:180; 5'-AAAGGATCCCCCGGGTTAAAAATTTAAAGTGC-AACC-3')). This manipulation removes most of the pol gene, but leaves the protease "gene" intact. The plasmid generated by this manipulation is called pHIV32.

pHIV32 is used in in vitro recombination experiments with ALVAC as the rescuing virus.

EXAMPLE 48

GENERATION OF HIV1 GENES IN NYVAC

Generation of NYVAC/HIV1 gag (+pro) and gp120 (+transmembrane) Recombinant. A plasmid, pHXB2D, containing human immunodeficiency virus type 1 (HIV1) cDNA sequence (IIIB) was obtained from Dr. R. C. Gallo (NCI-NIH). The sequence encoding the 5'-end of the gag gene was cloned between vaccinia virus tk flanking arms. This was accomplished by cloning the 1,625 bp BglII fragment of pHXB2D, containing the 5'-end of the gag gene, into the 4,075 bp BglII fragment of pSD542VCVQ. The plasmid generated by this manipulation is called pHIVG2.

The 3'-end of the gag gene was then cloned into pHIVG2. This was accomplished by cloning a 280 bp ApaI-BamHI PCR fragment, containing the 3'-end of the gag gene, into the 5,620 bp ApaI-BamHI fragment of pHIVG2. (This PCR fragment was generated from the plasmid, pHXB2D, with the oligonucleotides, HIVP5 (SEQ ID NO:116) and HIVP6 (SEQ ID NO:117)). The plasmid generated by this manipulation is called pHIVG3.

The I3L promoter was then cloned upstream of the gag gene. This was accomplished by cloning the oligonucleotides, HIVL17 (SEQ ID NO:118) and HIVL18 (SEQ ID NO:119), encoding the vaccinia virus I3L promoter and the 5'-end of the gag gene, into the the 5,540 bp partial BglII-ClaI fragment of pHIVG3. The plasmid generated by this manipulation is called pHIVG4.

The portion of the gag gene encoding p24, p2, p7 and p6 was then eliminated. This was accomplished by cloning the oligonucleotides, HIVL19 (SEQ ID NO:120) and HIVL20 (SEQ ID NO:121), into the 4,450 bp partial PvuII-BamHI fragment of pHIVG4. The plasmid generated by this manipulation is called pHIVG5.

The remainder of the gag gene, as well as the pol gene, was then cloned downstream of the p17 "gene". This was accomplished by cloning the 4,955 bp ClaI-SalI fragment of pHXB2D, containing most of the gag gene and all of the pol gene, into the 4,150 bp ClaI-SalI fragment of pHIVG5. The plasmid generated by this manipulation is called pHIVG6.

Extraneous 3'-noncoding sequence was then eliminated. This was accomplished by cloning a 360 bp AflII-BamHI PCR fragment, containing the 3'-end of the pol gene, into the 8,030 bp AflII-BamHI fragment of pHIVG6. (This PCR fragment was generated from the plasmid, pHXB2D, with the oligonucleotides, HIVP7 (SEQ ID NO:122) and HIVP8 (SEQ ID NO:123)). The plasmid generated by this manipulation is called pHIVG7.

The I3L-promoted gag and pol genes were then inserted into a canary pox insertion vector. This was accomplished by cloning the 4,360 bp partial BglII-BamHI fragment of pHIVG7, containing the I3L-promoted gag and pol genes, into the BamHI site of pVQH6CP3L. The plasmid generated by this manipulation is called pHIVGE14.

The H6-promoted HIV1 envelope "gp120" gene (MN) was then inserted into pHIVGE14. This was accomplished by cloning the 1,600 bp NruI-NotI fragment of pBSHIVMN120, containing the H6-promoted envelope "gp120" gene, and the oligonucleotides, HIVL29 (SEQ ID NO:129) and HIVL30 (SEQ ID NO:130), into the 11,500 bp NruI-XhoI fragment of pHIVGE14. The plasmid generated by this manipulation is called pHIVGE15.

The H6-promoted HIV1 envelope "gp120" gene (MN) and the I3L-promoted gag and pol genes (IIIB) were then inserted into a vaccinia virus insertion vector. This was accomplished by cloning the 6,400 bp NotI-BamHI fragment of pHIVGE15, containing the H6-promoted HIV1 envelope "gp120" gene (MN) and the I3L-promoted gag and pol genes (IIIB), into the 4,000 bp NotI-BglII fragment of pSD542 (defined in Example 15). The plasmid generated by this manipulation is called pHIVGE16.

The "gp120" gene was then replaced by the "gp160" gene. This was accomplished by cloning the 2,600 bp NruI-NotI fragment of pH6HMNE (defined in Example 10), containing the entire HIV1 envelope gene (MN), into the 8,000 bp partial NruI-NotI fragment of pHIVGE16. The plasmid generated by this manipulation is called pHIVGE19.

The part of the env gene encoding gp41 was then replaced with the env transmembrane region. This was accomplished by cloning the 1,700 bp NruI-NotI fragment of pBSHIVMN120T, containing the H6-promoted gp120 (+transmembrane) gene, into the 8,500 bp partial NruI-NotI fragment of pHIVGE19. The resulting plasmid is called pHIVGE19T.

Most of the pol gene was then removed. This was accomplished by cloning a 540 bp ApaI-SmaI PCR fragment, containing the 3'-end of the HIV1 protease "gene", into the 7,000 bp ApaI-SmaI fragment of pHIVGE19T. (This PCR fragment was generated from the plasmid, pHIVG7, with the oligonucleotides, HIVP5 (SEQ ID NO:116) and HIVP37 (SEQ ID NO:180)). This manipulation removes most of the pol gene, but leaves the protease "gene" intact. The plasmid generated by this manipulation is called pHIV33.

pHIV33 is used in in vitro recombination experiments with NYVAC as the rescuing virus.

EXAMPLE 49

GENERATION OF HIV2 GENES IN ALVAC

Generation of ALVAC/HIV2 gag/pol Recombinant. A plasmid, pBSH6HIV2ENV (defined in Example 4), contains the H6-promoted human immunodeficiency virus type 2 (HIV2) env gene. The H6-promoted env gene from this plasmid was cloned between canary pox flanking arms. This was accomplished by cloning the 2,700 bp XhoI-SacII fragment of pBSH6HIV2ENV and the oligonucleotides, HIV2L4 (SEQ ID NO:176) and HIV2L5 (SEQ ID NO:177), into the XhoI-EcoRI site of pC6L (defined in Example 50). The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

The env gene was then removed. This was accomplished by cloning the oligonucleotides, HIV2L8 (SEQ ID NO:181; 5'-CGATAAACCGC-3') and HIV2L9 (SEQ ID NO:182; 5'-GGTTTAT-3'), into the 8,800 bp partial ClaI-SstII fragment of pHIV25. The plasmid generated by this manipulation is called pHIV27.

pHIV27 was used in in vitro recombination experiments with ALVAC as the rescuing virus to yield vCP190.

Generation of ALVAC/HIV2 env (gp160) Recombinant. A plasmid, pBSH6HIV2ENV (defined in Example 4), contains the H6-promoted human immunodeficiency virus type 2 (HIV2) env gene. The H6-promoted env gene from this plasmid was cloned between canary pox flanking arms. This was accomplished by cloning the 2,700 bp XhoI-SacII fragment of pBSH6HIV2ENV and the oligonucleotides, HIV2L4 (SEQ ID NO:176) and HIV2L5 (SEQ ID NO:177), into the XhoI-EcoRI site of pC6L (defined in Example 50). The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

The gag and pol genes were then removed. This was accomplished by cloning the oligonucleotides, HIV2L10 (SEQ ID NO:183; 5'-GGGAAAG-3') and HIV2L11 (SEQ ID NO:184; 5'-GATCCTTTCCC-3'), into the 7,000 bp partial BamHI-SmaI fragment of pHIV25. The plasmid generated by this manipulation is called pHIV28.

pHIV28 was used in in vitro recombination experiments with ALVAC as the rescuing virus to yield vCP188.

Generation of ALVAC/HIV2 gp120 Recombinant. A plasmid, pBSH6HIV2ENV, contains the H6-promoted human immunodeficiency virus type 2 (HIV2) env gene. The H6-promoted env gene from this plasmid was cloned between canary pox flanking arms. This was accomplished by cloning the 2,700 bp XhoI-SacII fragment of pBSH6HIV2ENV (defined in Example 4) and the oligonucleotides, HIV2L4 (SEQ ID NO:176) and HIV2L5 (SEQ ID NO:177), into the XhoI-EcoRI site of pC6L. The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

The gag and pol genes were then removed. This was accomplished by cloning the oligonucleotides, HIV2L10 (SEQ ID NO:183) and HIV2L11 (SEQ ID NO:184), into the 7,000 bp partial BamHI-SmaI fragment of pHIV25. The plasmid generated by this manipulation is called pHIV28.

The part of the env gene encoding gp41 was then removed. This was accomplished by cloning the 360 bp PstI-XbaI fragment of pBSHIV2120B, containing the 3'-end of the gp120 gene, and the oligonucleotides, HIV2L12 (SEQ ID NO:185; 5'-CTAGAAAACCGC-3') and HIV2L13 (SEQ ID NO:186; 5'-GGTTTT-3'), into the 5,600 bp PstI-SstII fragment of pHIV28. The plasmid generated by this manipulation is called pHIV29.

pHIV29 is used in in vitro recombination experiments with ALVAC as the rescuing virus.

Generation of ALVAC/HIV2 gag/pol and gp120 Recombinant. A plasmid, pBSH6HIV2ENV (defined in Example 4), contains the H6-promoted human immunodeficiency virus type 2 (HIV2) env gene. The H6-promoted env gene from this plasmid was cloned between canary pox flanking arms. This was accomplished by cloning the 2,700 bp XhoI-SacII fragment of pBSH6HIV2ENV and the oligonucleotides, HIV2L4 (SEQ ID NO:176) and HIV2L5 (SEQ ID NO:177), into the XhoI-EcoRI site of pC6L (defined in Example 50). The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

The gag and pol genes were then removed. This was accomplished by cloning the oligonucleotides, HIV2L10 (SEQ ID NO:183) and HIV2L11 (SEQ ID NO:184), into the 7,000 bp partial BamHI-SmaI fragment of pHIV25. The plasmid generated by this manipulation is called pHIV28.

The part of the env gene encoding gp41 was then removed. This was accomplished by cloning the 360 bp PstI-XbaI fragment of pBSHIV2120B, containing the 3'-end of the gp120 gene, and the oligonucleotides, HIV2L12 (SEQ ID NO:185) and HIV2L13 (SEQ ID NO:186), into the 5,600 bp PstI-SstII fragment of pHIV28. The plasmid generated by this manipulation is called pHIV29.

The gp120 gene was then cloned into pHIV25. This was accomplished by cloning the 1,550 bp NruI-SacII fragment of pHIV29, containing the H6-promoted gp120 gene, into the 9,000 bp NruI-SacII fragment of pHIV25. The plasmid generated by this manipulation is called pHIV30.

pHIV30 is used in in vitro recombination experiments with ALVAC as the rescuing virus.

Generation of ALVAC/HIV2 gp120 (+transmembrane) Recombinant. A plasmid, pBSH6HIV2ENV (defined in Example 4), contains the H6-promoted human immunodeficiency virus type 2 (HIV2) env gene. The H6-promoted env gene from this plasmid was cloned between canary pox flanking arms. This was accomplished by cloning the 2,700 bp XhoI-SacII fragment of pBSH6HIV2ENV and the oligonucleotides, HIV2L4 (SEQ ID NO:176) and HIV2L5 (SEQ ID NO:177), into the XhoI-EcoRI site of pC6L (defined in Example 50). The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

The gag and pol genes were then removed. This was accomplished by cloning the oligonucleotides, HIV2L10 (SEQ ID NO:183) and HIV2L11 (SEQ ID NO:184), into the 7,000 bp partial BamHI-SmaI fragment of pHIV25. The plasmid generated by this manipulation is called pHIV28.

The part of the env gene encoding gp41 was then removed. This was accomplished by cloning the 360 bp PstI-XbaI fragment of pBSHIV2120B, containing the 3'-end of the gp120 gene, and the oligonucleotides, HIV2L12 (SEQ ID NO:185) and HIV2L13 (SEQ ID NO:186), into the 5,600 bp PstI-SstII fragment of pHIV28. The plasmid generated by this manipulation is called pHIV29.

The HIV1 env transmembrane region was then cloned onto the end of the gp120 gene. This was accomplished by cloning the 500 bp EcoRI fragment of pHIV31, containing the 3'-end of the gp120 gene and the env transmembrane region, into the 5,600 bp EcoRI fragment of pHIV29. (pHIV31 was derived by cloning a 500 bp PstI-XbaI PCR fragment, containing the 3'-end of the gp120 gene and the env transmembrane region, into the PstI-XbaI site of pIBI25. This PCR fragment was generated from the PCR fragment, PCRTM1, and the oligonucleotides, HIVTM1 (SEQ ID NO:107) and HIVTM2 (SEQ ID NO:108), with the oligonucleotides, HIV2P14 (SEQ ID NO:187; 5'-CAGAAGTAGCATATATGT-3') and HIVTM3 (SEQ ID NO:109). PCRTM1 was generated from the plasmid, pHIV28, with the oligonucleotides, HIV2P14 (SEQ ID NO:187) and HIV2P15 (SEQ ID NO:188; 5'-GCCTCCTACTATCATTATGAATAATCTCTTATGTC-TCCCTGGAGC-3')). The plasmid generated by this manipulation is called pHIV34.

pHIV34 is used in in vitro recombination experiments with ALVAC as the rescuing virus.

Generation of ALVAC/HIV2 gag/pol and gp120 (+ transmembrane) Recombinant. A plasmid, pBSH6HIV2ENV (defined in Example 4), contains the H6-promoted human immunodeficiency virus type 2 (HIV2) env gene. The H6-promoted env gene from this plasmid was cloned between canary pox flanking arms. This was accomplished by cloning the 2,700 bp XhoI-SacII fragment of pBSH6HIV2ENV and the oligonucleotides, HIV2L4 (SEQ ID NO:176) and HIV2L5 (SEQ ID NO:177), into the XhoI-EcoRI site of pC6L (defined in Example 50). The plasmid generated by this manipulation is called pHIV23.

The HIV2 gag and pol genes were then cloned into pHIV23. This was accomplished by cloning the 4,450 bp XmaI-NotI fragment of pHIV22, containing the I3L-promoted HIV2 gag and pol genes, and the oligonucleotides, HIV2L6 (SEQ ID NO:131) and HIV2L7 (SEQ ID NO:132), into the 7,000 bp XmaI-XhoI fragment of pHIV23. The plasmid generated by this manipulation is called pHIV25.

The gag and pol genes were then removed. This was accomplished by cloning the oligonucleotides, HIV2L10 (SEQ ID NO:183) and HIV2L11 (SEQ ID NO:184), into the 7,000 bp partial BamHI-SmaI fragment of pHIV25. The plasmid generated by this manipulation is called pHIV28.

The part of the env gene encoding gp41 was then removed. This was accomplished by cloning the 360 bp PstI-XbaI fragment of pBSHIV2120B (defined in Example 4), containing the 3'-end of the gp120 gene, and the oligonucleotides, HIV2L12 (SEQ ID NO:185) and HIV2L13 (SEQ ID NO:186), into the 5,600 bp PstI-SstII fragment of pHIV28. The plasmid generated by this manipulation is called pHIV29.

The HIV1 env transmembrane region was then cloned onto the end of the gp120 gene. This was accomplished by cloning the 500 bp EcoRI fragment of pHIV31, containing the 3'-end of the gp120 gene and the env transmembrane region, into the 5,600 bp EcoRI fragment of pHIV29. pHIV31 was derived by cloning a 500 bp PstI-XbaI PCR fragment, containing the 3'-end of the gp120 gene and the env transmembrane region, into the PstI-XbaI site of pIBI25 (IBI, New Haven, Conn.). This PCR fragment was generated from the PCR fragment, PCRTM1, and the oligonucleotides, HIVTM1 (SEQ ID NO:107) and HIVTM2 (SEQ ID NO:108), with the oligonucleotides, HIV2P14 (SEQ ID NO:187) and HIVTM3 (SEQ ID NO:109). PCRTM1 was generated from the plasmid, pHIV28, with the oligonucleotides, HIV2P14 (SEQ ID NO:187) and HIV2P15 (SEQ ID NO:188). The plasmid generated by this manipulation is called pHIV34.

The gp120 (+ transmembrane) gene was then cloned into a plasmid containing the HIV2 gag/pol genes. This was accomplished by cloning the 2,700 bp ClaI fragment of pHIV34, containing the H6-promoted gp120 (+transmembrane) gene, into the 6,800 bp ClaI fragment of pHIV30. (pHIV30 was derived by cloning the 1,550 bp NruI-SacII fragment of pHIV29, containing the H6-promoted gp120 gene, into the 9,000 bp NruI-SacII fragment of pHIV25.) The plasmid generated by this manipulation is called pHIV35.

pHIV35 is used in in vitro recombination experiments with ALVAC as the rescuing virus.

EXAMPLE 50

EXPRESSION OF TWO FUSION PEPTIDES CONTAINING THE p24 EPITOPE OF HIV-1 gag FUSED TO THE T1 AND V3

LOOP EPITOPES OF HIV-1 env WITH AND WITHOUT THE SIGNAL DOMAIN FROM HIV-1 env

Two expression cassettes were generated by a series of polymerase chain reactions described below. These cassettes differ in that one version encodes the signal sequences of HIV-1 env fused to the epitopes whereas the other does not.

The version of the fusion peptide with the signal is preceded by the 51 amino acid N-terminal portion of HIV-1 (IIIB) env, residues 1–50 (plus initiating Met) based on Ratner et al. (1985) followed by a cleavable linker region. The amino acid sequence of this region is (SEQ ID NO:189) MKEQKTVAMRVKEKYQHLWRWGWRWGTMLLGM-LMICSATEKLWVTVYYGVP-PFRK. Both versions of the fusion peptide, contain an amino acid sequence based on the defined T-cell epitopes of p24, the V3 loop (MN), and T1 of HIV-1 (MN) env. The peptide is designed such that the epitopes are separated from each other and the signal where present by the sequence (SEQ ID NO:189) PPFRK. The sequence of this region of the peptide is (SEQ ID NO:190) [signal-PFRK]-GPKEPFRDYVDRFYK-PPFRK-VQINCTRPNYNKRKRIHIGPGRAFYTTKNIIGTIRQAH CNISRAK-PPFR-KQIINMWQEVEKAMYA. In the version lacking the signal sequence, the region indicated by [signal-PFRK] is replaced by an initiating methionine only.

For the cassette with the signal, the H6 promoter and signal were derived by PCR from plasmid pBST1T2TH4.1

(described above) using primers H6PCR1 (SEQ ID NO:157; 5'- ACTACTAAGCTTCTTTATTCTATACTTAAAAAGTG -3') and SIGPCR24 (SEQ ID NO:191; 5'-AGGTCCCTTCCTGAATGGAGGTACCCCATAATAG-ACTG-3'). The p24 epitope was fused to the signal sequence by PCR amplification of this 307 bp PCR-derived fragment and oligonucleotides P24A (SEQ ID NO:192; 5'-CCATTCAGGAAGGGACCTAAAGAACCTTTTAGA-GATTATGTAGATAGATTTTATAAACCACCTTT TAGAAAA-3') and P24B (SEQ ID NO:193; 5'-TTTTCTAAAAGGTGGTTTATAAAATCTATCTACA-TAATCTCTAAAAGGTTCTTTAGGTCCCTTCC TGAATGG-3') using primers H6PCR1 and P24PCR (SEQ ID NO:194; 5'-GTACAATTAATTTGTACTTTTCTAAAA-GGTGGTTTATAAAATC-3'). This 377 bp PCR-derived fragment consists of the H6 promoter coupled to coding sequences for the signal, the p24 epitope and the first 6 amino acids of the V3 loop.

For the cassette without the signal, the H6 promoter were derived by PCR from plasmid pH6T2 (described above) using primers H6PCR1 (SEQ ID NO:157) and H6P24 (SEQ ID NO:195; 5'-GGTGGTTTATAAAATCTATCT- ACAT-AATCTCTAAAAGGTTCTTTAGGTCCCAT-TACGATACAAAC TTAACGG-3'). The p24 epitope was fused to the promoter by PCR amplification of this 187 bp PCR-derived fragment and oligonucleotides P24A (SEQ ID NO:192) and P24B (SEQ ID NO:193) using primers H6PCR1 (SEQ ID NO:157) and P24PCR (SEQ ID NO:194). This 214 bp PCR-derived fragment consists of the H6 promoter coupled to coding sequences for the p24 epitope and the first 6 amino acids of the V3 loop.

Coding sequences for the V3 loop region were derived by PCR amplification of the SmaI fragment from plasmid pHIVGE16EV (described above) using primers V3PCR1 (SEQ ID NO:196; 5'-AAACCACCTTTTAGAAAAGTACAAATTAA-TTGTAC-3') and V3PCR2 (SEQ ID NO:197; 5'-CTGCTTACGGAACGGTGGTTTTGCTCTACTAAT-GTTACAATG-3'). The T1 epitope was joined to the coding region for the V3 loop by PCR amplification of this 171 bp PCR-derived fragment and oligonucleotides MNT1A (SEQ ID NO:198; 5'-CCACCGTTCCGTAAGCAGATAATAAAC-ATGTGGCAAGAAGTAGAAAAAGCTATGTATGCTT-AA-3') and MNT1B (SEQ ID NO:199; 5'-TTAAGCATACATAGCTTTTTCTACTTCTTGCCAC-ATGTTTATTATCTGCTTACGGAACGGTGG-3') as template using primers V3PCR1 (SEQ ID NO:196) and T1MNPCR (SEQ ID NO:200; 5'-TCATCAAAGCTTCTCGAGAAAAATTAAGCATAC-ATAGCTTTTTC-3'). This 239 bp PCR-derived fragment consists of the last codon of p24 epitope, the V3 loop, ant the T1 epitope followed 3' by an early transcription termination signal (TTTTTNT) and XhoI and HindIII sites.

For the cassette with the signal, the promoter, signal and p24 epitope coding sequences were joined to the coding region for the V3 loop/T1 epitope by PCR amplification of the 377 bp and 239 bp PCR-derived fragments using primers H6PCR1 (SEQ ID NO:157) and T1MNPCR (SEQ ID NO:200). Following digestion of this 581 bp PCR-derived fragment with HindIII, a fragment of 563 bp was isolated from an agarose gel, ligated to similarly digested pBS (Stratagene, La Jolla, Calif.) creating plasmid pMNT1P24. The insert was verified by nucleotide sequence analysis.

For the cassette without the signal, the promoter and p24 coding sequences were joined to the coding region for the V3 loop/T1 epitope by PCR amplification of the 171 bp and 239 bp PCR-derived fragments using primers H6PCR1 (SEQ ID NO:157) and T1MNPCR (SEQ ID NO:200). Following digestion of this 418 bp PCR-derived fragment with HindIII. a fragment of 400 bp was isolated from an agarose gel, ligated to similarly digested pBS (Stratagene. La Jolla, Calif.) creating plasmid pMN24EV3T1NSA. The insert was verified by nucleotide sequence analysis.

A C6 insertion vector containing 370 bp upstream of C6, polylinker containing SmaI, PstI. XhoI, and EcoRI sites, and 1156 bp of downstream sequence was derived in the following manner. The 0.4 kb upstream sequence was generated by PCR amplification of a cosmid clone derived from purified genomic canarypox DNA using oligonucleotides C6A1SG (SEQ ID NO:201; 5'- ATCATCGAGCTCGCG-GCCGCCTATCAAAAGTCTTAATGAGTT -3') and C6B1SG (SEQ ID NO:202; 5'- GAATTCCTCGAGCTG-CAGCCCGGGTTTTTATAGCTAATTAGT-CATTTTTTCGTAAGTAAGT ATTTTTATTTAA -3'). The 1.2 kb downstream arm was generated by PCR amplification of the same template using oligonucleotides C6C1SG (SEQ ID NO:203; 5'- CCCGGGCTGCAGCTCGAGGAAT-TCTTTTTATTGATTAACTAGTCAAAT-GAGTATATATAAT TGAAAAAGTAA -3') and C6D1SG (SEQ ID NO:204; 5'- GATGATGGTACCTTCATAAATA-CAAGTTTGATTAAACTTAAGTTG -3'). These fragments were fused by a third PCR employing gel purified 0.4 and 1.2 kb fragments as template for primers C6A1SG (SEQ ID NO:201) and C6D1SG (SEQ ID NO:204). The resulting 1.6 kb fragment was isolated from an agarose gel, digested with SacI and KpnI and ligated to similarly digested pBS (Stratagene, La Jolla, Calif.) generating C6 insertion plasmid pC6L.

Both expression cassettes were excised by PstI/XhoI digestion of pMNT1P24 and pMN24EV3T1NSA, isolated from agarose gels and ligated separately to similarly digested pC6L creating plasmids pC6P24FS and pC6P24FNS respectively, for recombination into the C6 locus of ALVAC. The resulting recombinants are designated vCP189 and vCP195, respectively.

BamHI/XhoI fragments from pMNT1P24 and pMN24EV3T1NSA were ligated to similarly digested pSD550VC (defined in Example 33) creating pI4P24FS and pI4P24FNS for recombination into the I4 locus of NYVAC generating vP1117 and vP1110, respectively.

Expression of Tetanus Toxin Fragment C in Poxviruses Expressing HIV-1 Proteins. It has been proposed that the addition of various Th epitopes from homologous (Good et al., 1987) and heterologous proteins (Francis et al., 1987) may be capable of recruiting T-cell help for specific B cell responses to synthetic peptide vaccines. In an effort to elicit enhanced immune responses to HIV-1 antigens, various T-cell epitopes derived from HIV-1 have been incorporated into recombinant poxviruses. To further pursue this strategy, tetanus toxin fragment C, which contains other known human T-helper cell epitopes (Ho et al., 1990), will be co-expressed with HIV-1 antigens in an ALVAC recombinant. The presence of these epitopes from tetanus toxin may enhance the immune response against HIV-1 by providing nonspecific T-cell help.

PstI/SmaI digested pC6P24FS (described above) was modified by ligating the PstI/SmaI fragment from plasmid pVQ42KTH4.1 (described above) creating pC6P24FSVQ. This plasmid was digested with NruI within the H6 promoter and XhoI at the 3' end and ligated to a 1.4 kb fragment isolated from similarly digested pH6TETC (described above). The resulting plasmid, pC6VQTETC, was confirmed by restriction digestion and nucleotide sequence analysis of the regions surrounding the cloning sites. Following confirmation pC6VQTETC was employed in recombination experiments with vCP112, vCP125 and vCP156.

EXAMPLE 51

PERIPHERAL BLOOD MONONUCLEAR CELL STUDIES WITH NYVAC/HIV-1 AND ALVAC/HIV-1 RECOMBINANTS

While broad issues concerning the immunogenicity of NYVAC/HIV-1 and ALVAC/HIV-1 constructs in man are best addressed within the context of clinical trials, a number of relevant insights have already been gleaned by in vitro cellular response assays. A central question regarding the use of these vaccine constructs in man is their capacity to impact on cellular anti-HIV-1 reactivities, especially cytotoxic T-lymphocytes (CTL) responses. Whether as a component of a preventative or a therapeutic vaccine strategy, there are ample precedents suggesting a beneficial role for CTL in a number of viral infections in man (McMichael et al., 1983; Moss et al., 1978; Borysiewicz et al., 1988). Although the precise contribution of anti-HIV-1 CTL in preventing or controlling viral infection remains to be elucidated, studies by Letvin and co-workers using the SIV/macaque animal model suggest that anti-SIV-1 CTL, especially gag-specific CTL, may represent a major determinant controlling disease progression (Letvin and King, 1990). This coupled with the observations of numerous investigators that anti-HIV-1 CTL activities can be measured directly from fresh peripheral blood mononuclear cells (PBMC) in a relatively high proportion of asymptomatic patients (reviewed in Walker and Plata, 1990; Autran et al., 1991), support the contention that elicitation of anti-HIV-1 CTL reactivities should be included as a major goal of both preventative and therapeutic vaccines.

Figure 11:
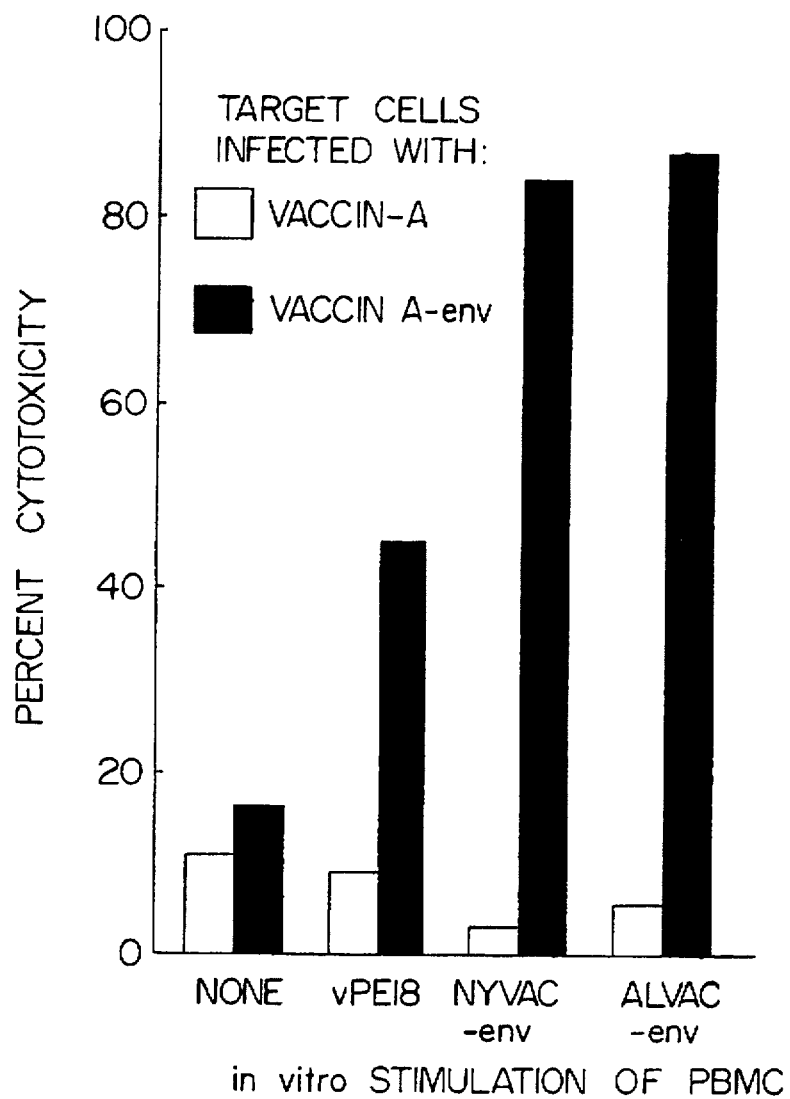
FIG. 11 shows percent cytotoxity versus in vitro stimulation of PBMC.

To test the capacity of NYVAC/HIV-1 and ALVAC/HIV-1 constructs to impact on relevant CTL reactivities, a series of experiments were conducted involving a cohort of HIV-1 infected patients devoid of detectable direct anti-HIV-1 gp160 CTL reactivities. PBMCs were obtained from these patients and a portion of the PBMC were infected with either the fully replication-competent vaccinia/gp 160 construct vPE16 (Walker et al., 1987), or the replication-attenuated NYVAC/gp160 or ALVAC/gp160 constructs. The acutely infected PBMC were washed and used as stimulators for the remaining PBMC in a 10-day in vitro stimulation protocol. Controls included both unstimulated and control vector (i.e. parental poxvirus minus HIV-1 genes) stimulated cultures. Following the 10-day incubation in the absence of exogenous IL-2, cells were washed and evaluated for CTL activities against autologous B-lymphocyte cell lines (BLCL) infected with either a control vaccinia virus, vSC8, or the vaccinia/gp160 vPE16 construct. Additionally, phenotypic depletion of CD8+ cells was performed in parallel using magnetic microsphere sorting. The results of these studies shown in FIG. 11 revealed that whereas unstimulated or control vector-stimulated cultures had no detectable CTL activity against HIV-1 gp160 targeted BLCL, cultures stimulated with any of the HIV-1 gp160 constructs had a high level of anti-gp160 cytolytic activity, all of which was abolished following removal of CD8+ cells and thereby consistent with the appearance of CTL activities. Perhaps the most significant observation to come out of these studies was the consistent finding that the magnitude of the CTL response was greater in the NYVAC/gp160 and ALVAC/gp160-stimulated cultures than in those which were stimulated with the fully replication competent vPE16 infected PBMC. It is not known whether this apparent enhancement in CTL stimulation by NYVAC/gp160 and ALVAC/gp160 was due to differences in expression by the recombinants as compared to vPE16 or to the attenuation characteristics of the NYVAC and ALVAC vectors.

Extensive flow cytometric analyses of the various stimulated cultures was also performed in order to more thoroughly identify the effector cell phenotype which was elicited. When compared to either unstimulated or control vector stimulated cultures, generation of anti-gp160 cytolytic reactivities generally resulted in a decline in $CD3^+$/$CD4^+$ subpopulations and a compensatory rise in $CD3^+$/$CD8^+$ cells. Significant increases in $CD3^+$/$CD25^+$, $CD3^+$/$HLA-DR^+$, $CD8^+$/$S6F1^+$, $CD8^+$/$CD38^+$, and $CD3^+$/$CD69^+$ cells were also noted. When the cytolytic activities of each culture were plotted against increases in particular cell subpopulations, a linear relationship was found between cellular anti-gp160 reactivity and increases in the $CD8^+$/$S6F1^+$ population. This cellular phenotype broadly defines CTL (Morinoto et al., 1987).

These early pre-clinical studies with cells from HIV-1 infected patients clearly illustrate the capacity of NYVAC and ALVAC/HIV-1 vectors to elicit potent CTL activities from precursor populations which are contained within the PBMC pool of patients. Furthermore, these studies strongly exemplify the potential clinical utility of these vectors in the context of a therapeutic vaccine strategy. This could take the form of simple immunization with these vectors or could involve an ex vivo component of either cellular targeting and re-infusion or ex vivo CTL generation followed by large scale adoptive transfer. In either case, the combined safety of the non-replicating vectors and their inherently strong cellular immunogenicity make them ideal candidates for immune-based therapy in man.

Having thus described in detail preferred embodiments of the present invention, it is to be understood that the invention defined by the appended claims is not to be limited to the particular details set forth in the above description as many apparent variations thereof are possible without departing from the spirit or scope of the present invention.

REFERENCES

1. Autran, B., Plata, F. and Debre, P., J. AIDS, 4, 361–367 (1991)
2. Behbehani, A. M., Microbiological Reviews 47, 455–509 (1983).
3. Bertholet, C., Drillien, R. and Wittek, R., Proc. Natl. Acad. Sci. 82, 2096–2100 (1985).
4. Borysiewicz, I., Graham, S., Hickling, J., Mason, P. D., and Sissons, J. P. G., Eur. J. Immunol. 18, 269–275 (1988)
5. Chakrabarti, S., Robert-Guroff, M., Wong-Staal, F., Gallo, R. C., and Moss, B., Nature 320, 535–537 (1986).
6. Cianciolo, G. J., Copeland T. D., Oroszlan S., and Snyderman, R., Science 230, 453–456 (1985).
7. Clewell, D. B., and Helinski, D. R., Proc. Natl. Acad. Sci. USA 62, 1159–1166 (1969).
8. Clewell, D. B., J. Bacteriol 110, 667–676 (1972).
9. Colinas, R. J., Condit, R. C., and Paoletti, E., Virus Research 18, 49–70 (1990).
10. Derosiers, R. C., M. S., Wyand, T. Kodama, T. J. Ringler, L. O. Arthur, P. K. Seghal, N. L. Letvin, N. W. King, and M. D. Daniel Proc. Natl. Acad. Sci. USA 86, 6353–6357 (1989).
11. Dreyfuss, G., Adam, S. A., and Choi, Y.-D., Mol. Cell. Biol. 4, 415–423 (1984).

12. Engelke, D. R., Hoener, P. A., and Collins, F. S., Proc. Natl. Acad. Sci. USA 85, 544–548 (1988).
13. Franchini, G., Gurgo, C., Guo, H.-G., Gallo, R. C., Collati, E., Fargnoli, K. A., Hall, L. F., Wong-Staal, F., and Reitz, Jr., M. S., Nature (London) 328, 539–543 (1987).
14. Franchini, G., Fargnoli, K. A., Giomnini, F., Jagodzinski, L., DeRossi, A., Bosch, M., Biberfield, G., Fenyo, E. M., Albert, J., Gallo, R. C., and Wong-Staal, F., Proc. Natl. Acad. Sci. USA 86, 2433–2437 (1989).
15. Francis, M. J., Hastings, G. Z., Syred, A. D., McGinn, B., Brown, F., and Rowlands, D. J., Nature 330, 168–170 (1987).
16. Gillard, S., Spehner, D., Drillien, R., and Kirn, A., Proc. Natl. Acad. Sci. USA 83, 5573–5577 (1986).
17. Goebel, S. J., Johnson, G. P., Perkus, M. E., Davis, S. W., Winslow, J. P., and Paoletti, E., Virology 179, 247–266 (1990a).
18. Goebel, S. J., Johnson, G. P., Perkus, M. E., Davis, S. W., Winslow, J. P., and Paoletti, E., Virology 179, 517–563 (1990b).
19. Good, M. F., Maloy, W. L., Lunde, M. N., Margalit, H., Cornette, J. L., Smith, G. L., Moss, B., Miller, L. H., and Berzofsky, J. A., Science 235, 1059–1062 (1987).
20. Guo, H.-G., Veronese, F., Tschachler, E., pal, R., Kalyanaraman, V. S., Gallo, R. C., and Reitz, Jr., M. S., Virology 174, 217–214 (1990).
21. Guo, P., Goebel, S., Davis, S., Perkus, M. E., Taylor, J., Norton, E., Allen, G., Lanquet, B., Desmettre P., and Paoletti, E., J. Virol. 64, 2399–2406 (1990).
22. Guo, P., Goebel, S., Davis, S., Perkus, M. E., Lanquet, B., Desmettre, P., Allen, G., and Paoletti, E., J. Virol. 63, 4189–4198 (1989).
23. Gurgo, C., Guo, H.-G., Franchini, G., Aldovini, A., Collalti, E., Farrell, K., Wong-Staal, F., Gallo, R. C., and Reitz, M. S., Jr., Virology 164, 531 (1988).
24. Haffar, O., Garrigues, J., Travis, B., Moran, P., Zarling, J., and Hu, S.-L., J. Virol. 64, 2653–2659, (1990).
25. Ho, P. C., Mutch, D. A., Winkel, K. D., Saul, A. J., Jones, G. L., Doran, T. J., and Rzepczyk, C. M., Eur. J. Immunol. 20, 477–483 (1990).
26. Hosmalin, A., Nara, P. L., Zweig, M., Lerche, N. W., Cease, K. B., Gard, E. A., Markham, P. D., Putney, S. D., Daniel, M. D., Desrosiers, R. C., and Berzofsky, J. A. J. Immunol. 146, 1667–1673 (1991).
27. Hu, S.-L., Fultz, P., McClure, H., Eichberg, J., Thomas, E., Zarling, J., Singhal, M., Kosowski, S., Swenson, R., Anderson, D., and Todaro, G., Nature 328, 721–723 (1987).
28. Hu, S.-L., Travis, B. M., Garrigues, J., Zarling, J. M., Eichberg, J. W. and Alpers, C. E., In Vaccine 90, eds. Chanock, R. M., Lerner, R. A., Brown, F., and Ginsberg, H., (Cold Spring Harbor Press, Cold Spring Harbor, N.Y.) pp. 231–236 (1990).
29. Hu, S.-L., Kosowski, S., and Dalrymple, J., Nature 320, 535–537, (1986).
30. Hu, S. L., Zarling, J. M., Chinn, J., Travis, B. M., Moran, P. A., Sias, J., Kuller, L., Morton, W. R., Heidecker, G., and Benveniste, R. E., Proc. Natl. Acad. Sci. USA 86, 7213 (1989).
31. Javeherian, K., Langlois, A. J. MCDanal, C., Ross, K. L., Eckler, L. I., Jellib, C. L., Profy, A. T., Rusche, J. R., Bolognesi, D. P., Putney, S. D., and Matthews, T. J. Proc. Natl. Acad. Sci. USA 86, 6768–6772 (1989).
32. Karacostas, V., Nagashima, K., Gonda, M. A., and Moss, B. Proc. Natl. Acad. Sci. USA 86, 8964–8968 (1989).
33. Klasse, P. J., Pipkorn, R., and Blomberg, J., Proc. Natl. Acad. Sci. USA 85, 5225–5229 (1988).
34. Knauf, V. C. and Nester, E. W., Plasmid 8, 45–54 (1982).
35. Kodama, T., Wooley, D. P., Naidu, Y. M., Kestler III, H. W., Daniel, M. D., Li, Y., and Derisiers, R. C. J. Virol. 63, 4709–4714 (1989).
36. Koff, W. C. and Fauci, A. S., AIDS 1, 5125–5129 (1989).
37. Koup, R. A., Sullivan, J. L., Levine, P. H., Brettler, D., Mahr, A., Mazzara, G., McKenzie, S., and Panicali, D. Blood 73, 1909–1919 (1989).
38. Kunkel, T. A., Proc. Natl. Acad. Sci. USA 82, 488–492 (1985).
39. Laemmli, U. K., Nature (London) 227, 680–685 (1970).
40. Lane, J. M., Ruben, F. L., Neff, J. M., and Millar, J. D. New Eng. J. Med. 281, 1201–1208 (1969).
41. LaRosa, G. J., Davide, J. P., Weinhold, K., Waterbury, J. A., Profy, A. T., Lewis, J. A., Langlois, A. J., Dressman, G. R., Boswell, R. N., Shadduck, P., Holley, L. H., Karpus, M., Bolognesi, D. P., Matthews, T. J., Emini, E. A., and Putney, S. D., Science 249, 932–935 (1990).
42. Letvin, N. L., and King, N. W., J. AIDS, 3, 1023–40 (1990)
43. Mandecki, W., Proc. Natl. Acad. Sci. USA 83, 7177–7182 (1986).
44. Maniatis, T., Fritsch, E. F., and Sambrook, J. In Molecular cloning: a laboratory manual, (Cold Spring Harbor Laboratory, Cold Spring Harbor, N.Y.) (1982). 45. McMichael, A. J., Gotch, F. M., Noble, G. R. and Beare, P. A. S., New Engl. J. Med. 309, 13–17 (1983)
46. Michel, F., Hoffenbach, A., Langlade-Demoyen, P., Guy, B., Lecocq, J.-P., Wain-Hobson, S., Kieny, M.-P., and Plata, F., Eur. J. Immunology 18, 1917–1927 (1988).
47. Moss, D. J., Rickinson, A. B., and Pope, J. H., Int. J. Cancer 22, 662–668 (1978)
48. Murphy-Corb, M., Martin, L. N., Davison-Fairburn, B., Montelaro, R. C., Miller, M., West, M., Ohkawa, S., Baskin, G. B., Zhang, J.-Y., Putney, S. D., Allison, A. C. and Eppstein, D. A., Science 246, 1293–1297 (1989).
49. Nixon, D. F., Townsend, A. R. M., Elvin, J. G., Rizza, C. R., Gallwey, J., and McMichael, A. J., Nature 326, 484–487 (1988).
50. Panicali, D., and Paoletti, E., Proc. Natl. Acad. Sci. USA 79, 4927–4931 (1982).
51. Perkus, M. E., Piccini, A., Lipinskas, B. R., and Paoletti, E., Science 229, 981–984 (1985).
52. Perkus, M. E., Goebel, S. J., Davis, S. W., Johnson, G. P., Limbach, K., Norton, E. K., and Paoletti, E., Virology 179, 276–286 (1990).
53. Perkus, M. E., Limbach K., and Paoletti, E., J. Virol. 63, 3829–3836 (1989).
54. Piccini, A., Perkus, M. E., and Paoletti, E., Methods in Enzymology 153, 545–563 (1987).
55. Plata, F., Autran, B., Martins, L. P., Wain-Hobson, S., Raphael, M., Mayaud, C., Denis, M., Guillon, J.-M., Debre, P., Nature 328, 348–351 (1987).
56. Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, S. R. Jr., Pearson, M. L., Lautenberger, J. A., Papas, T. S., Ghrayeb, J., Chang, N. T., Gallo, R. C., and Wong-Staal, F., Nature 313, 277 (1985).
57. Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petteway, Jr., S. R., Pearson, M. L., Lautenberger, J. A., Papas, T. S., Ghrayeb, J., Chang, N. T., Gallo., R. C., and Wong-Staal F., Nature 313, 277–284 (1985).
58. Rautmann, G., Kieny, M.-P., Brandely, R., Dott, K., Girard, M. Montagnier, L., and Lecocg, J.-P. AIDS Research and Human Retroviruses 5, 147–157 (1989).

59. Riviere Y., Tanneau-Salvadori, F., Regnault, A., Lopez, O., Sansonetti, P., Guy, B., Kieny, M.-P., Fournel, J.-J., and Montagnier, L., J. Virol. 63, 2270–2277 (1989).
60. Ruegg, C. L., Monell, C. R., and Strand, M., J. Virol. 63, 3250–3256 (1989a).
61. Ruegg, C. L., Monell, C. R., and Strand, M., J. Virol. 63, 3257–3260 (1989b).
62. Sanchez-Pascador, R., Power, M. D., Barr, P. J., Steimer, K. S., Stampien, M. M., Brown-Shimer, S. L., Gee, W., Renard, A., Randolph, A., Levy, J. A., Dina, D., and Luciw, P. A., Science 227, 484–492 (1985).
63. Sanger, F., Nickeln, S., and Coulson, A. R., Proc. Natl. Acad. Sci. 74, 5463–5467 (1977).
64. Schmaljohn, C. S., Jennings, G. B., Hay, J., Dalrymple, J. M., Virology 155, 633–43 (1986).
65. Schmitt, J. F. C., and Stunnenberg, H. G., J. Virol. 62, 1889–1897 (1988).
66. Shaffermann, A., Lennox, J., Grosfeld, H., Sadoff, J., Redfield, R. R., and Burke, D. S., AIDS Research and Human Retroviruses 5, 33–39 (1989).
67. Shapira, S. K., Chou, J., Richaud, F. V., and Casadaban, M. J., Gene 25, 71–82 (1983).
68. Shioda, T. and H. Shibuta Virology 175, 139–148 (1990).
69. Starcich et al., Cell 45, 637–648 (1986).
70. Tabor, S., and Richardson, C. C., Proc. Natl. Acad. Sci. USA 84, 4767–4771 (1987).
71. Tartaglia, J. and Paoletti, E., In Immunochemistry of viruses, II, eds. van Regenmortel, M. H. V. and Neurath, A. R., (Elsevier Science Publishers B. V., Amsterdam) pp. 125 (1990).
72. Tartaglia, J., Winslow, J., Goebel, S., Johnson, G. P., Taylor, J., and Paoletti, E. J. Gen. Virol. 71, 1517–1524 (1990).
73. Tartaglia, J. Perkus, M. E., Taylor, J. Norton, E. K., Audonnet, J. C., Cox, W. I., Davis, S. W., VanderHoven, J., Meignier, B., Riviere, M., Languet, B. and Paoletti, E., Virology, 188 (1992).
74. Taylor, J., Weinberg, R., Lanquet, B., Desmettre, P., and Paoletti, E., Vaccine 6, 497–503 (1988a).
75. Taylor, J., Weinberg, R., Kawaoka, Y., Webster, R. G., and Paoletti, E., Vaccine 6, 504–508 (1988b).
76. Taylor, J., Weinberg, R., Tartaglia, J., Richardson, C., Alkhatib, G., Briedis, D., Appel, M., Norton, E., and Paoletti, E., Virology 187, 321–328 (1992).
77. Vos, J. C., and Stunnenberg, H. G., EMBO J. 7, 3487–3492 (1988).
78. Walker, B. D., Flexner, C., Paradis, T. J., Fuller, T. C., Hirsch, M. S., Schooley, R. T. and Moss, B., Science 240, 64–66 (1988).
79. Walker, B. D., Chakrabarti, S., Moss, B., Paradi, T. J., Flynn, T., Durno, A. G., Blumberg, R. S., Kaplan, J. C., Hirsch, M. S., and Schooley, R. T., Nature 328, 345–348 (1987).
80. Walker, B. D., Flexner, C., Birch-Limberger, K., Fisher, L., Paradis, T. J., Aldovini, A., Young, R., Moss, B., and Schooley, R. T., Proc. Natl. Acad. Sci. 86, 9514–9519 (1989).
81. Walker, B. D. and Plata, F., AIDS 4, 177–184 (1990)
82. Weiss, R. A., Clapham, P. R., Cheingsong-Popov, R., Dalgleish, G., Carne, C. A., Weller, I. V., and Tedder, R. S., Nature 316, 69–72 (1985).
83. Yuen, L., and Moss, B., Proc. Natl. Acad. Sci. USA 84, 6417–6421 (1987).
84. Zagury, D., Bernard, J., Cheynier, R., Desportes, I., Leonard, R., Fouchard, I., Reveil, B., Ittele, D., Lurhuma, Z., Mbayo, K., Wane, J., Salaun, J.-J., Goussard, B., Dechazal, L., Burny, A., Nara, P. and Gallo, R. C., Nature 332, 728–731 (1988).
85. Zarling, J. M., Morton, W., Moran, P. A., McClure, J., Kosowski, S. G., and Hu, S.-L., Nature 323, 344–346 (1986).

---

What is claimed is:

1. A recombinant attenuated ALVAC canarypox virus comprising an exogenous DNA segment encoding a lentivirus gene product.

2. The recombinant virus of claim 1 wherein the exogenous DNA segment encodes a human immunodeficiency virus or simian immunodeficiency virus gene product.

3. The recombinant virus of claim 2 wherein the exogenous DNA segment encodes a human immunodeficiency virus gene product.

4. The recombinant virus of claim 2 wherein the exogenous DNA segment encodes a simian immunodeficiency virus gene product.

5. The recombinant virus of claim 1 wherein said exogenous DNA segment further encodes a human T-helper lymphocyte epitope derived from tetanus toxoid fragment C.

6. The recombinant virus of claim 5 wherein said exogenous DNA segment encodes a human immunodeficiency virus or simian immunodeficiency virus gene product.

7. The recombinant virus of claim 6 wherein said exogenous DNA segment encodes a human immunodeficiency virus gene product.

8. The recombinant virus of claim 6 wherein said exogenous DNA segment encodes a simian immunodeficiency virus gene product.

9. A recombinant attenuated ALVAC canarypox virus selected from the group consisting of vCP95, vCP112, vCP60, vCP61, vCP125, vCP124, vCP126, vCP144, vCP120, vCP138, vCP117, vCP130, vCP152, vCP155, vCP156, vCP146, vCP148, vCP154, vCP168, vCP153, and vCP172.

10. The recombinant virus of claim 1 wherein the gene product is selected from the group consisting of: gp160; gp120; Gag and Pol; Gag, Pol and gp120; Gag, Pol and gp160; Gag, Pol and truncated Env; non-cleavable gp160; gp120 anchored with transmembrane; Gag, Pol, and gp120 anchored with transmembrane; signal domain of Env and p24 fused to T1 and V3 loop of Env; p24 fused to T1 and V3 loop of Env; Nef; V3 loop fused to 88 epitope; T1, T2, and TH4.1 epitopes; Env signal domain, T1, T2, and TH4.1 epitopes; and, Gag, Pol protease and gp120 anchored with a transmembrane sequence.

11. An immunogenic composition comprising a recombinant attenuated canarypox virus as claimed in any one of claims 1 to 10 and an adjuvant.

12. A method for expressing a lentiviral gene product comprising infecting a suitable host cell with a recombinant attenuated canarypox virus as claimed in any one of claims 1 to 10.

13. A method of inducing an immunological response to a lentivirus gene product comprising administering a recombinant attenuated canarypox virus as claimed in any one of claims 1 to 10.

14. A method of inducing an immunological response to a lentivirus gene product comprising administering an immunogenic composition as claimed in claim 11.

* * * * *

SEQUENCE LISTING ( 1 ) GENERAL INFORMATION:

( i i i ) NUMBER OF SEQUENCES: 205

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

TAATTAACTA GCTACCCGGG 20

( 2 ) INFORMATION FOR SEQ ID NO:2:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:2:

AATTCCCGGG TAGCTAGTTA ATTACATG 28

( 2 ) INFORMATION FOR SEQ ID NO:3:

( i ) SEQUENCE CHARACTERISTICS:
　　　　( A ) LENGTH: 73 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:3:

```
AGCTTCCCGG GTAAGTAATA CGTCAAGGAG AAAACGAAAC GATCTGTAGT TAGCGGCCGC      60
CTAATTAACT AAT                                                        73
```

( 2 ) INFORMATION FOR SEQ ID NO:4:

( i ) SEQUENCE CHARACTERISTICS:
　　　　( A ) LENGTH: 69 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:4:

```
ATTAGTTAAT TAGGCGGCCG CTAACTACAG ATCGTTTCGT TTTCTCCTTG ACGTATTACT      60
TACCCGGGA                                                             69
```

( 2 ) INFORMATION FOR SEQ ID NO:5:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:5:

```
TTAGTTAATT AGGCGGCCGC                                                 20
```

( 2 ) INFORMATION FOR SEQ ID NO:6:

( i ) SEQUENCE CHARACTERISTICS:
　　　　( A ) LENGTH: 22 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:6:

```
CGATTACTAT GAAGGATCCG TT                                              22
```

( 2 ) INFORMATION FOR SEQ ID NO:7:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:7:

```
AACGGATCCT TCATAGTAAT                                                 20
```

( 2 ) INFORMATION FOR SEQ ID NO:8:

( i ) SEQUENCE CHARACTERISTICS:
　　　　( A ) LENGTH: 41 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:8:

```
CGATTACTAG ATCTGAGCTC CCCGGGCTCG AGGGATCCGT T                         41
```

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AACGGATCCC TCGAGCCGG GGAGCTCAGA TCTAGTAAT                                 39
```

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GATCCGAATT CTAGCT                                                        16
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGCTAGAATT CG                                                            12
```

( 2 ) INFORMATION FOR SEQ ID NO:12:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
TATGAGTAAC TTAACTCTTT TGTTAATTAA AAGTATATTC AAAAAATAAG TTATATAAAT         60
AGATCTGAAT TCGTT                                                         75
```

( 2 ) INFORMATION FOR SEQ ID NO:13:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
AACGAATTCA GATCTATTTA TATAACTTAT TTTTGAATA TACTTTTAAT TAACAAAAGA          60
GTTAAGTTAC TCA                                                           73
```

( 2 ) INFORMATION FOR SEQ ID NO:14:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AAAATGGGCG TGGATTGTTA ACTTATATA ACTTATTTTT TGAATATAC                    49
```

( 2 ) INFORMATION FOR SEQ ID NO:15:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ACACGAATGA TTTTCTAAAG TATTTGGAAA GTTTATAGG TAGTTGATAG AACAAAATAC        60
ATAATTT                                                                67
```

( 2 ) INFORMATION FOR SEQ ID NO:16:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
TCTATCAACT ACCTATAAAA CTTTCCAAAT ACTTTAGAAA ATCATTCGTG T                51
```

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
TGTAAAAATA AATCACTTTT TATACTAAGA TCTCCCGGGC TGCAGC                     46
```

( 2 ) INFORMATION FOR SEQ ID NO:18:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GGCCGCTGCA GCCCGGGAGA TCTTAGTATA AAAAGTGATT TATTTTTACA AAATTATGTA       60
TTTTGT                                                                 66
```

( 2 ) INFORMATION FOR SEQ ID NO:19:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
TTTCTGTATA TTTGCACCAA TTTAGATCTT ACTCAAAATA TGTAACAATA                  50
```

( 2 ) INFORMATION FOR SEQ ID NO:20:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

TGTCATTTAA CACTATACTC ATATTAATAA AAATAATATT TATT 44

( 2 ) INFORMATION FOR SEQ ID NO:21:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GATCCTGAGT ACTTTGTAAT ATAATGATAT ATATTTCAC TTTATCTCAT TTGAGAATAA 60

AAAGATCTTA GG 72

( 2 ) INFORMATION FOR SEQ ID NO:22:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

AATTCCTAAG ATCTTTTTAT TCTCAAATGA GATAAAGTGA AATATATAT CATTATATTA 60

CAAAGTACTC AG 72

( 2 ) INFORMATION FOR SEQ ID NO:23:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

GATCCAGATC TCCCGGGAAA AAAATTATTT AACTTTTCAT TAATAGGGAT TTGACGTATG 60

TAGCGTACTA GG 72

( 2 ) INFORMATION FOR SEQ ID NO:24:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

AATTCCTAGT ACGCATCATA CGTCAAATCC CTATTAATGA AAAGTTAAAT AATTTTTTC 60

CCGGGAGATC TG 72

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

ATGGTAGAAA TTAATTGTAC 20

( 2 ) INFORMATION FOR SEQ ID NO:26:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

ATCATCGAAT TCAAGCTTAT TATTTGCTC TACTAATGTT AC                                42

( 2 ) INFORMATION FOR SEQ ID NO:27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

ATGAATGTGA CAGAAAATTT AACATGTGG AAAAATGTAG AAATTAATTG TACAAGACCC            60

( 2 ) INFORMATION FOR SEQ ID NO:28:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GGGTCTTGTA CAATTAATTT CTACATTTTT CCACATGTTA AATTTTCTG TCACATTCAT            60

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AGTAATGTGA CAGAAAATTT TAAC                                                  24

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

AGGCAAGCTT TCAAAAAAAT ATAAATGATT C                                          31

( 2 ) INFORMATION FOR SEQ ID NO:31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TTTATATTGT AATTATATAT TTTC                                                  24

( 2 ) INFORMATION FOR SEQ ID NO:32:

( i ) SEQUENCE CHARACTERISTICS:

(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:32:

GTTTTAATTG TGGAGGGGAA TTCTTCTACT GTAATTC    37

(2) INFORMATION FOR SEQ ID NO:33:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:33:

ATCATCTCTA GAATAAAAAT TATAGCAAAA TCCTTTC    37

(2) INFORMATION FOR SEQ ID NO:34:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:34:

TGCTACTCCT AATGGTTC    18

(2) INFORMATION FOR SEQ ID NO:35:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:35:

CATATGCTTT AGCATCTGAT G    21

(2) INFORMATION FOR SEQ ID NO:36:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:36:

ATGAAAGAGC AGAAGACAGT G    21

(2) INFORMATION FOR SEQ ID NO:37:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:37:

ATCATCGGTA CCGATTCTTT ATTCTATAC    29

(2) INFORMATION FOR SEQ ID NO:38:

(i) SEQUENCE CHARACTERISTICS:
(A) LENGTH: 19 base pairs
(B) TYPE: nucleic acid ( C ) STRANDEDNESS: single
        ( D ) TOPOLOGY: linear ( x i ) SEQUENCE DESCRIPTION: SEQ ID NO:38:

TACGATACAA ACTTAACGG                                                                                  19

( 2 ) INFORMATION FOR SEQ ID NO:39:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GAATTACAGT AGAAGAATTC CCCTCCACAA TTAAAAC                                                              37

( 2 ) INFORMATION FOR SEQ ID NO:40:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CAATAGATAA TGATACTAC                                                                                  19

( 2 ) INFORMATION FOR SEQ ID NO:41:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GTATTATATC AAGTTTATAT AATAATGCAT ATTC                                                                 34

( 2 ) INFORMATION FOR SEQ ID NO:42:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

GTTGATGATC TGTAGTGC                                                                                   18

( 2 ) INFORMATION FOR SEQ ID NO:43:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

ATCATCTCTA GAATAAAAAT TATGGTTCAA TTTTTACTAC TTTTATATTA TATATTTC                                       58

( 2 ) INFORMATION FOR SEQ ID NO:44:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

CAATAATCTT TAAGCAAATC CTC    23

( 2 ) INFORMATION FOR SEQ ID NO:45:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

AGAGGGGAAT TCTTCTACTG CAATACA    27

( 2 ) INFORMATION FOR SEQ ID NO:46:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:46:

Leu Gln Ala Arg Val Leu Ala Val Glu Arg Tyr Leu Arg Asp Gln Gln
1               5                   10                  15

Leu ( 2 ) INFORMATION FOR SEQ ID NO:47:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

TTGGAAAGGC TTTTGGCATG CCACGCGTC    29

( 2 ) INFORMATION FOR SEQ ID NO:48:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

ACAGTCTGGG GCATCAAGCA GCTAGGGATT TGGGGTTGCT CT    42

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

CCGTTAAGTT TGTATCGTAA TGAAAGTGAA GGGGACCAGG    40

( 2 ) INFORMATION FOR SEQ ID NO:50:

( i ) SEQUENCE CHARACTERISTICS:
        ( A ) LENGTH: 54 base pairs
        ( B ) TYPE: nucleic acid
        ( C ) STRANDEDNESS: single (D) TOPOLOGY: linear (xi) SEQUENCE DESCRIPTION: SEQ ID NO:50:

ATGAGTGGTA AAATTCAGCT GCTTGTTGCC TTTCTGCTAA CTAGTGCTTG CTTA  54

(2) INFORMATION FOR SEQ ID NO:51:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:51:

TAAGCAAGCA CTAGTTAGCA GAAAGGCAAC AAGCAGCTGA ATTTTACCAC TCAT  54

(2) INFORMATION FOR SEQ ID NO:52:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:52:

ATCATCAAGC TTGATTCTTT ATTCTATAC  29

(2) INFORMATION FOR SEQ ID NO:53:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:53:

CAGCTGAATT TTACCACTCA TTACGATACA AACTTAACG  39

(2) INFORMATION FOR SEQ ID NO:54:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:54:

TAAGCAAGCA CTAGTTAG  18

(2) INFORMATION FOR SEQ ID NO:55:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:55:

CCGCCTCTTG ACCAGAC  17

(2) INFORMATION FOR SEQ ID NO:56:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:56:

ATCATCTCTA GAATAAAAAT TACAGGAGGG CAATTTCTG   39

(2) INFORMATION FOR SEQ ID NO:57:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:57:

ATCATCTCTA GAATAAAAAT TATCTCTTAT GTCTCCTGG   40

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:58:

AATTAACTTT ACAGCACC   18

(2) INFORMATION FOR SEQ ID NO:59:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:59:

CGATATCCGT TAAGTTTGTA TCGTAATGGG ATGTCTTGGG AATC   44

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:60:

CAAGGCTTTA TTGAGGTCTC   20

(2) INFORMATION FOR SEQ ID NO:61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:61:

CCTGGCCTTG GCAGATAG   18

(2) INFORMATION FOR SEQ ID NO:62:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:62:

ATCATCGAAT TCAAAAATAT TACAAAGAGC GTGAGCTCAA GTCCTTGCCT AATCCTCC   58

( 2 ) INFORMATION FOR SEQ ID NO:63:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

CCCCCCAAGC TTTTTTATTC TATACTT   27

( 2 ) INFORMATION FOR SEQ ID NO:64:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

CAAGGCTTTA TTGAGGTCTC   20

( 2 ) INFORMATION FOR SEQ ID NO:65:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CAGTTGGTAC CACTGGTATT TTATTTCAG   29

( 2 ) INFORMATION FOR SEQ ID NO:66:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

TATCTGAATT CCTGCAGCCC GGGTTTTAT AGCTAATTAG TCAAATGTGA GTTAATATTA   60

G   61

( 2 ) INFORMATION FOR SEQ ID NO:67:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

TCGCTGAATT CGATATCAAG CTTATCGATT TTTATGACTA GTTAATCAAA TAAAAAGCAT   60

ACAAGC   66

( 2 ) INFORMATION FOR SEQ ID NO:68:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

TTATCGAGCT CTGTAACATC AGTATCTAAC  30

( 2 ) INFORMATION FOR SEQ ID NO:69:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

TCGAGTGAGA TAAAGTGAAA ATATATATCA TTATATTACA AGTACAATTA TTTAGGTTTA  60

ATCATGGGCG  70

( 2 ) INFORMATION FOR SEQ ID NO:70:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

CCCATGATTA AACCTAAATA ATTGTACTTT GTAATATAAT GCTATATATT TTCACTTTAT  60

CTCAC  65

( 2 ) INFORMATION FOR SEQ ID NO:71:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

AATCAGAGAG CAGGCT  16

( 2 ) INFORMATION FOR SEQ ID NO:72:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

TTGGATCCCT ATGCCACCTC TCT  23

( 2 ) INFORMATION FOR SEQ ID NO:73:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

AGACCAACAG CACCATCTAG CGGCAGAGGA GGAAATTACT AATTTTATT CTAGAG  56

( 2 ) INFORMATION FOR SEQ ID NO:74:

( i ) SEQUENCE CHARACTERISTICS:
        ( A ) LENGTH: 58 base pairs
        ( B ) TYPE: nucleic acid
        ( C ) STRANDEDNESS: single ( D ) TOPOLOGY: linear ( x i ) SEQUENCE DESCRIPTION: SEQ ID NO:74:

GATCCTCTAG AATAAAAATT AGTAATTTCC TCCTCTGCCG CTAGATGGTG CTGTTGGT 58

( 2 ) INFORMATION FOR SEQ ID NO:75:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

TAGACAAAAT TGAAAATATA TAATTACAAT ATAAATGCC AGTACAACAA ATAGGTGGTA 60

ACTATGTCCA CCTGCCATT 79

( 2 ) INFORMATION FOR SEQ ID NO:76:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

GCTTAATGGC AGGTGGACAT AGTTACCACC TATTTGTTGT ACTGGCATTT TATATTGTAA 60

TTATATATTT TCAATTTTGT 80

( 2 ) INFORMATION FOR SEQ ID NO:77:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

TGGATGTACA GACAAC 16

( 2 ) INFORMATION FOR SEQ ID NO:78:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

AAGGATCCGA ATTCTTACAT TAATCTAGCC TTC 33

( 2 ) INFORMATION FOR SEQ ID NO:79:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( x i ) SEQUENCE DESCRIPTION: SEQ ID NO:79:

```
Cys Asn Thr Arg Lys Arg Ile Arg Ile Gln Arg Gly Pro Gly Arg Ala
 1               5                  10                  15
    Phe Val Thr Gly Lys
                20
```

( 2 ) INFORMATION FOR SEQ ID NO:80:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:80:

```
Cys Asn Lys Arg Lys Arg Ile His Ile Gly Pro Gly Arg Ala Phe Tyr
 1               5                  10                  15

Thr Thr Lys Asn
            20
```

( 2 ) INFORMATION FOR SEQ ID NO:81:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( x i ) SEQUENCE DESCRIPTION: SEQ ID NO:81:

```
Cys Asn Thr Arg Lys Ser Ile Tyr Ile Gly Pro Gly Arg Ala Phe His
 1               5                  10                  15

Thr Thr Gly Arg
            20
```

( 2 ) INFORMATION FOR SEQ ID NO:82:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

GGGTTATTAA TGATCTGTAG                                                                           20

( 2 ) INFORMATION FOR SEQ ID NO:83:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

ATCATCGAGC TCTGTTCCTT GGGTTCTTAG                                         30

( 2 ) INFORMATION FOR SEQ ID NO:84:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

ATCATCTCTA GAATAAAAAT TATAGCAAAG CCCTTTCCAA GCC                    43

( 2 ) INFORMATION FOR SEQ ID NO:85:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

ATCATCGAGC TCCTATCGCT GCTC  24

( 2 ) INFORMATION FOR SEQ ID NO:86:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

AGCTTCTTTA TTCTATACTT AAAAAGTGAA AATAAATACA AAGGTTCTTG AGGGT  55

( 2 ) INFORMATION FOR SEQ ID NO:87:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

TGTGTTAAAT TGAAAGCGAG AAATAATCAT AAATTATTTC ATTATCGCGA TATCCGTTAA  60

GTTTGTATCG TAC  73

( 2 ) INFORMATION FOR SEQ ID NO:88:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

TTATTAGTAT TTAATAAAGT AATAGCGCTA TAGGCAATTC AAACATAGCA TGAGCT  56

( 2 ) INFORMATION FOR SEQ ID NO:89:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

AGAAATAAGA TATGAATTTT TCACTTTTAT TTATGTTCC AAGAACTCCC AACACAATTT  60

AACTTTCGCT CT  72

( 2 ) INFORMATION FOR SEQ ID NO:90:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

ATCATCGAAT TCTGAATGTT AAATGTTATA CTTTG  35

( 2 ) INFORMATION FOR SEQ ID NO:91:

( i ) SEQUENCE CHARACTERISTICS:
        ( A ) LENGTH: 28 base pairs
        ( B ) TYPE: nucleic acid ( C ) STRANDEDNESS: single
( D ) TOPOLOGY: linear ( x i ) SEQUENCE DESCRIPTION: SEQ ID NO:91:

GGGGGTACCT TTGAGAGTAC CACTTCAG     28

( 2 ) INFORMATION FOR SEQ ID NO:92:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:92:

ATCATCCTGC AGGTATTCTA AACTAGGAAT AGATG     35

( 2 ) INFORMATION FOR SEQ ID NO:93:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:93:

ATCATCCTGC AGGTATTCTA AACTAGGAAT AGATG     35

( 2 ) INFORMATION FOR SEQ ID NO:94:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:94:

AATACGACTC ACTATAG     17

( 2 ) INFORMATION FOR SEQ ID NO:95:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:95:

ATCATCTCTA GAATAAAAAT TATCTTTTTT CTCTCTGCAC CACTC     45

( 2 ) INFORMATION FOR SEQ ID NO:96:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:96:

GAAATAATAA AACAATAATC     20

( 2 ) INFORMATION FOR SEQ ID NO:97:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:97:

GCTCCTATTC CCACTGCAGT TTTTCTCTC TGCAC    35

( 2 ) INFORMATION FOR SEQ ID NO:98:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:98:

GTCCTGCAGG ATGGAAAAGA ATGCCCCAAG C    31

( 2 ) INFORMATION FOR SEQ ID NO:99:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:99:

GGGGGAGGCA AACTACCAAG G    21

( 2 ) INFORMATION FOR SEQ ID NO:100:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

ATCATCTCTA GAATAAAAAT TAGAGTTTCA AAGGC    35

( 2 ) INFORMATION FOR SEQ ID NO:101:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:101:

CGCCAGCATG CAGAAGCAGC    20

( 2 ) INFORMATION FOR SEQ ID NO:102:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

ATCATCTCTA GAATAAAAAT TATAGGAAAG CCCTTTCCAA GCC    43

( 2 ) INFORMATION FOR SEQ ID NO:103:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

GTGCAGAGAA AAAACTGCAG TGGGAATAGG AGC 33

( 2 ) INFORMATION FOR SEQ ID NO:104:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

ATCATCTCTA GAATAAAAAT TACAAACTTG CCCATTTATC CAATTCC 47

( 2 ) INFORMATION FOR SEQ ID NO:105:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

ATCATCTCTA GAATAAAAAT TACAAACTTG CCCATTTATC TAATTCC 47

( 2 ) INFORMATION FOR SEQ ID NO:106:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

GCCTCCTACT ATCATTATGA ATAATCTTTT TCTCTCTG 38

( 2 ) INFORMATION FOR SEQ ID NO:107:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

TTATTCATAA TGATAGTAGG AGGCTTGGTA GGTTTAAGAA TAGTTTTTGC TGTACTCTCT 60

GTAGTGAATA GAGTTAGGCA GGGATAA 87

( 2 ) INFORMATION FOR SEQ ID NO:108:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

TTATCCCTGC CTAACTCTAT TCACTACAGA GAGTACAGCA AAAACTATTC TTAAACCTAC 60

CAAGCCTCCT ACTATCATTA TGAATAA 87

( 2 ) INFORMATION FOR SEQ ID NO:109:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

ATCATCTCTA GAATAAAAAT TATCCCTGCC TAACTCTATT CAC 43

( 2 ) INFORMATION FOR SEQ ID NO:110:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

GTACGTGACT AATTAGCTAT AAAAGGATC CGGTACCCTC GAGTCTAGAA TCGATCCCGG 60

GTTTTTATGA CTAGTTAATC AC 82

( 2 ) INFORMATION FOR SEQ ID NO:111:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

GGCCGTGATT AACTAGTCAT AAAAACCCGG GATCGATTCT AGACTCGAGG GTACCGGATC 60

CTTTTTATAG CTAATTAGTC AC 82

( 2 ) INFORMATION FOR SEQ ID NO:112:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:112:

GATCTTAATT AATTAGTCAT CAGGCAGGGC GAGAACGAGA CTATCTGCTC GTTAATTAAT 60

TAGGTCGACG 70

( 2 ) INFORMATION FOR SEQ ID NO:113:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

GATCCGTCGA CCTAATTAAT TAACGAGCAC ATAGTCTCGT TCTCGCCCTG CCTGATGACT 60

AATTAATTAA 70

( 2 ) INFORMATION FOR SEQ ID NO:114:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

GGTCGACGGA TCCT 14

( 2 ) INFORMATION FOR SEQ ID NO:115:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:115:

GATCAGGATC CGTCGACCTG CA  22

( 2 ) INFORMATION FOR SEQ ID NO:116:

( i ) SEQUENCE CHARACTERISTICS:
  ( A ) LENGTH: 16 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:116:

TGTGGCAAAG AAGGGC  16

( 2 ) INFORMATION FOR SEQ ID NO:117:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:117:

TTGGATCCTT ATTGTGACGA GGGGTC  26

( 2 ) INFORMATION FOR SEQ ID NO:118:

( i ) SEQUENCE CHARACTERISTICS:
  ( A ) LENGTH: 106 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:118:

GATCTTGAGA TAAAGTGAAA ATATATATCA TTATATTACA AAGTACAATT ATTTAGGTTT  60

AATCATGGGT GCGAGAGCGT CAGTATTAAG CGGGGAGAA TTAGAT  106

( 2 ) INFORMATION FOR SEQ ID NO:119:

( i ) SEQUENCE CHARACTERISTICS:
  ( A ) LENGTH: 104 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:119:

CGATCTAATT CTCCCCCGCT TAATACTGAC GCTCTCGCAC CCATGATTAA ACCTAAATAA  60

TTGTACTTTG TAATATAATG ATATATATTT TCACTTTATC TCAA  104

( 2 ) INFORMATION FOR SEQ ID NO:120:

( i ) SEQUENCE CHARACTERISTICS:
  ( A ) LENGTH: 68 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:120:

CTGACACAGG ACACAGCAAT CAGGTCAGCC AAAATTACTA ATTTTATCT CGAGGTCGAC  60

AGGACCCG                                                                                               68

(2) INFORMATION FOR SEQ ID NO:121:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:121:

GATCCGGGTC CTGTCGACCT CGAGATAAAA ATTAGTAATT TTGGCTGACC TGATTGCTGT          60

GTCCTGTGTC AG                                                             72

(2) INFORMATION FOR SEQ ID NO:122:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:122:

AAGAAAATTA TAGGAC                                                         16

(2) INFORMATION FOR SEQ ID NO:123:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:123:

TTGGATCCCT AATCCTCATC CTGT                                                24

(2) INFORMATION FOR SEQ ID NO:124:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:124:

AAAGTCGACC CATATCACCT AGAAC                                               25

(2) INFORMATION FOR SEQ ID NO:125:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:125:

TTTGGATCCT TACAAAACTC TTGCCTTAT                                           29

(2) INFORMATION FOR SEQ ID NO:126:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO:126:

| | |
|---|---|
| TCGAGCAAAA TTGAAAATAT ATAATTACAA TATAAAATGC CTATAGTGCA GAACATCCAG | 60 |
| GGGCAAATGG TACATCAGGC CATATCACCT AGAACTTTAA ATGCA | 105 |

( 2 ) INFORMATION FOR SEQ ID NO:127:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:127:

| | |
|---|---|
| TTTAAAGTTC TAGGTGATAT GGCCTGATGT ACCATTTGCC CCTGGATGTT CTGCACTATA | 60 |
| GGCATTTTAT ATTGTAATTA TATATTTTCA ATTTTGC | 97 |

( 2 ) INFORMATION FOR SEQ ID NO:128:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:128:

| | |
|---|---|
| GCCTCCTACT ATCATTATGA ATAAACTGAT GGGAGGGGCA TAC | 43 |

( 2 ) INFORMATION FOR SEQ ID NO:129:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:129:

| | |
|---|---|
| GGCCGCAAC | 9 |

( 2 ) INFORMATION FOR SEQ ID NO:130:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:130:

| | |
|---|---|
| TCGAGTTGC | 9 |

( 2 ) INFORMATION FOR SEQ ID NO:131:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:131:

| | |
|---|---|
| GGCCAAAC | 8 |

( 2 ) INFORMATION FOR SEQ ID NO:132:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:132:

TCGAGTTT 8

( 2 ) INFORMATION FOR SEQ ID NO:133:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:133:

CCCCCCAAGC TTACATCATG CAGTGGTTAA AC 32

( 2 ) INFORMATION FOR SEQ ID NO:134:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:134:

GATTAAACCT AAATAATTGT 20

( 2 ) INFORMATION FOR SEQ ID NO:135:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:135:

ACAATTATTT AGGTTAACTG CA 22

( 2 ) INFORMATION FOR SEQ ID NO:136:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:136:

GTTAACCTAA ATAATTGT 18

( 2 ) INFORMATION FOR SEQ ID NO:137:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

TAATCATGAA ACAAATTATT AATATGTGGC AAGAAGAGGA AAAGCTATGT ACGCTTGACT 60

AGTTAATCAC TCGAG 75

( 2 ) INFORMATION FOR SEQ ID NO:138:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:138:

```
GATCCTCGAG TGATTAACTA GTCAAGCGTA CATAGCTTTT CCTACTTCTT GCCACATATT      60

AATAATTTGT TTCATGATTA                                                  80
```

( 2 ) INFORMATION FOR SEQ ID NO:139:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

```
ATCCGTTAAG TTTGTATCGT AATGCACGAA GATATTATTT CTTTGTGGGA TCAATCTTTA      60

AAATGACTAG TTAATCAG                                                    78
```

( 2 ) INFORMATION FOR SEQ ID NO:140:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

```
GATCCTGATT AACTAGTCAT TTTAAAGATT GATCCCACAA AGAAATAATA TCTTCGTGCA      60

TTACGATACA AACTTAACGG AT                                               82
```

( 2 ) INFORMATION FOR SEQ ID NO:141:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

```
AATTAATTAG CTGCAGCCCC GGGTCAAAAA AATATAAATG                            40
```

( 2 ) INFORMATION FOR SEQ ID NO:142:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

```
CCTTGTACTA CTTCAATTAC TCTATCCATT TTATATTGTA ATTATATATT TTC             53
```

( 2 ) INFORMATION FOR SEQ ID NO:143:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

```
TCAAAAAAAT ATAAATGATT CACCATCTGA TAGAAAAAAA ATTTATTGGG AAGAATATGA      60

TAATATTTTG GGATTTCAAA ATTGAAAATA TATAATTACA ATATAAA                   107
```

( 2 ) INFORMATION FOR SEQ ID NO:144:

( i ) SEQUENCE CHARACTERISTICS:
    ( A ) LENGTH: 73 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:144:

```
ATGGATAGAG TAATTGAAGT AGTACAAGGA GCTTATAGAG CTATTAGATG ACTAGTTAAT      60

CACTCGAGGA TCC                                                        73
```

( 2 ) INFORMATION FOR SEQ ID NO:145:

( i ) SEQUENCE CHARACTERISTICS:
    ( A ) LENGTH: 73 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:145:

```
GGATCCTCGA GTGATTAACT AGTCATCTAA TAGCTCTATA AGCTCCTTGT ACTACTTCAA      60

TTACTCTATC CAT                                                        73
```

( 2 ) INFORMATION FOR SEQ ID NO:146:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:146:

```
ATCATCGGAT CCTCGAGTGA TTAAACTAGT CATCTAATAG CTC                       43
```

( 2 ) INFORMATION FOR SEQ ID NO:147:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:147:

```
TTAATCAGGA TCCTTAATTA ATTAGTTATT AGACAAGGTG AAAACGAAAC TATTTGTAGC      60

TTAATTAATT AGCTGCAGCC CGGG                                            84
```

( 2 ) INFORMATION FOR SEQ ID NO:148:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:148:

```
CCCGGGCTGC AGCTAATTAA TTAAGCTACA AATAGTTTCG TTTTCACCTT GTCTAATAAC      60

TAATTAATTA AGGATCCTGA TTAA                                            84
```

( 2 ) INFORMATION FOR SEQ ID NO:149:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:149:

```
TTAATCAGGA TCCTTAATTA ATTAGTTATT AGAC                                    34
```

( 2 ) INFORMATION FOR SEQ ID NO:150:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:150:

```
ATCATCGGAT CCTCGAGTGA TTAACTAGTC ATCTAATAGC TC                           42
```

( 2 ) INFORMATION FOR SEQ ID NO:151:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:151:

```
AATTGCGGCC GC                                                            12
```

( 2 ) INFORMATION FOR SEQ ID NO:152:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:152:

```
AGAAAAATCA GTTAGCTAAG ATCTCCCGGG CTCGAGGGTA CCGGATCCTG ATTAGTTAAT        60

TTTTGT                                                                   66
```

( 2 ) INFORMATION FOR SEQ ID NO:153:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:153:

```
GATCACAAAA ATTAACTAAT CAGGATCCGG TACCCTCGAG CCCGGGAGAT CTTAGCTAAC        60

TGATTTTCT                                                                70
```

( 2 ) INFORMATION FOR SEQ ID NO:154:

( i ) SEQUENCE CHARACTERISTICS:
        ( A ) LENGTH: 51 amino acids
        ( B ) TYPE: amino acid
        ( C ) STRANDEDNESS: single
        ( D ) TOPOLOGY: linear ( x i ) SEQUENCE DESCRIPTION: SEQ ID NO:154:

```
Met Lys Glu Gln Lys Thr Val Ala Met Arg Val Lys Glu Lys Tyr Gln
 1               5                  10                  15

His Leu Trp Arg Trp Gly Trp Arg Trp Gly Thr Met Leu Leu Gly Met
                20                  25                  30

Leu Met Ile Cys Ser Ala Thr Glu Lys Leu Trp Val Thr Val Tyr Tyr
                35                  40                  45

Gly Val Pro
```

( 2 ) INFORMATION FOR SEQ ID NO:155:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( x i ) SEQUENCE DESCRIPTION: SEQ ID NO:155:

```
Pro Phe Arg Lys Gln Ile Ile Asn Met Trp Gln Glu Val Gly Lys Ala
 1               5                  10                  15

Met Tyr Ala Pro Pro Phe Arg Lys His Glu Asp Ile Ile Ser Leu Trp
            20                  25                  30

Asp Gln Ser Leu Lys Pro Pro Phe Arg Lys Asp Arg Val Ile Glu Val
             35              40                  45

Val Gln Gly Ala Tyr Arg Ala Ile Arg Pro Pro Phe Arg Lys
         50                  55                  60
```

( 2 ) INFORMATION FOR SEQ ID NO:156:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( x i ) SEQUENCE DESCRIPTION: SEQ ID NO:156:

```
Leu Phe Ile Met Ile Val Gly Gly Leu Val Gly Leu Arg Ile Val Phe
 1               5                  10                  15

Ala Val Leu Ser Val Val Asn Arg Val Arg Gln Gly
            20                  25
```

( 2 ) INFORMATION FOR SEQ ID NO:157:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

ACTACTAAGC TTCTTTATTC TATACTTAAA AAGTG          35

( 2 ) INFORMATION FOR SEQ ID NO:158:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:158:

CATATTAATT TGTTTTCTAA AAGGAGGTAC CCCATAATAG ACTGTG      46

( 2 ) INFORMATION FOR SEQ ID NO:159:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

GCTCCTCCTT TTAGAAAACA CGAAGATATT ATTTCTTTGT GGGATCAATC TTTAAAACCT    60

CCTTTTAGAA AAGATAGAGT AATTGAAGTA GTAC 94

( 2 ) INFORMATION FOR SEQ ID NO:160:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

GTACTACTTC AATTACTCTA TCTTTCTAA AAGGAGGTTT TAAAGATTGA TCCCACAAAG 60

AAATAATATC TTCGTGTTTT CTAAAAGGAG GAGC 94

( 2 ) INFORMATION FOR SEQ ID NO:161:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:161:

AAACAAATTA TTAATATGTG GCAAGAAGTA GGAAAAGCTA TGTACGCTCC TCCTTTTAGA 60

AAACACGAAG 70

( 2 ) INFORMATION FOR SEQ ID NO:162:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:162:

ACTACTTCTA GATTATCTAA TAGCTCTATA AGCTCCTTGT ACTACTTCAA TTACTC 56

( 2 ) INFORMATION FOR SEQ ID NO:163:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:163:

TACTATCATT ATGAATAATT TTCTAAAAGG AGGTCTAATA GCTCTATAAG CTCCTTGTAC 60

TACTTCAATT ACTC 74

( 2 ) INFORMATION FOR SEQ ID NO:164:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:164:

ATCATCGGAT CCAAGCTTAC ATCATGCAGT GG 32

( 2 ) INFORMATION FOR SEQ ID NO:165:

( i ) SEQUENCE CHARACTERISTICS:
        ( A ) LENGTH: 49 base pairs
        ( B ) TYPE: nucleic acid ( C ) STRANDEDNESS: single
        ( D ) TOPOLOGY: linear ( x i ) SEQUENCE DESCRIPTION: SEQ ID NO:165:

CGTTTTGACC ATTTGCCACC CATGATTAAA CCTAAATAAT TGTACTTTG 49

( 2 ) INFORMATION FOR SEQ ID NO:166:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:166:

AGTACAATTA TTTAGGTTTA ATCATGGGTG GCAAATGGTC AAAACG 46

( 2 ) INFORMATION FOR SEQ ID NO:167:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:167:

ATCATCGGAT CCTAACACTT CTCTCTCCGG 30

( 2 ) INFORMATION FOR SEQ ID NO:168:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:168:

ATCATCGGAT CCTAACACTT CTCTCTCCGG GTCATCCATC CATGCTGGCT CATAG 55

( 2 ) INFORMATION FOR SEQ ID NO:169:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:169:

AATTAACCCG GGATCCAAGC TTCTAGCTAG CTAATTTTA TAGCGGCCGC TATAATCGTT 60

AACTTATTAG 70

( 2 ) INFORMATION FOR SEQ ID NO:170:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:170:

GCTAGAAATC TCTTAGTTTT TATAGTTG 28

( 2 ) INFORMATION FOR SEQ ID NO:171:

( i ) SEQUENCE CHARACTERISTICS:
        ( A ) LENGTH: 28 base pairs
        ( B ) TYPE: nucleic acid -continued (C) STRANDEDNESS: single
(D) TOPOLOGY: linear (xi) SEQUENCE DESCRIPTION: SEQ ID NO:171:

GTTACATATG TACAGAATCT GATCATAG                                   28

(2) INFORMATION FOR SEQ ID NO:172:

(i) SEQUENCE CHARACTERISTICS:
    (A) LENGTH: 67 base pairs
    (B) TYPE: nucleic acid
    (C) STRANDEDNESS: single
    (D) TOPOLOGY: linear (xi) SEQUENCE DESCRIPTION: SEQ ID NO:172:

CTAGCTAGAA GCTTGGATCC CGGGTTAATT AATTAATAAA AAGCGGCCGC GTTAAAGTAG   60

AAAAATG                                                            67

(2) INFORMATION FOR SEQ ID NO:173:

(i) SEQUENCE CHARACTERISTICS:
    (A) LENGTH: 67 base pairs
    (B) TYPE: nucleic acid
    (C) STRANDEDNESS: single
    (D) TOPOLOGY: linear (xi) SEQUENCE DESCRIPTION: SEQ ID NO:173:

CGCCCATGAT TAAACCTAAA TAATTGTACT TTGTAATATA ATGATATATA TTTTCACTTT   60

ATCTCAC                                                            67

(2) INFORMATION FOR SEQ ID NO:174:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO:174:

ATGGCAGTTC ATTGCAT                                                 17

(2) INFORMATION FOR SEQ ID NO:175:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (xi) SEQUENCE DESCRIPTION: SEQ ID NO:175:

TTCCCGGGAG ATCTCTATGC CATTTCTCCA T                                 31

(2) INFORMATION FOR SEQ ID NO:176:

(i) SEQUENCE CHARACTERISTICS:
    (A) LENGTH: 5 base pairs
    (B) TYPE: nucleic acid
    (C) STRANDEDNESS: single
    (D) TOPOLOGY: linear (xi) SEQUENCE DESCRIPTION: SEQ ID NO:176:

GGTTG                                                              5

(2) INFORMATION FOR SEQ ID NO:177:

(i) SEQUENCE CHARACTERISTICS:

(A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:177:

AATTCAACCG C    11

( 2 ) INFORMATION FOR SEQ ID NO:178:

( i ) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:178:

CTAGCTAAGT TAAGGCAGGG GTATAGGCCA GTGTTCTCTT CCCCACCCTC TTATTCCAG    60

CAGACTCATA CCCAACAG    78

( 2 ) INFORMATION FOR SEQ ID NO:179:

( i ) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:179:

GTCCTGTTGG GTATGAGTCT GCTGGAAATA AGAGGGTGGG GAAGAGAACA CTGGCCTATA    60

CCCCTGCCTT AACTTAG    77

( 2 ) INFORMATION FOR SEQ ID NO:180:

( i ) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:180:

AAAGGATCCC CCGGGTTAAA AATTTAAAGT GCAACC    36

( 2 ) INFORMATION FOR SEQ ID NO:181:

( i ) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:181:

CGATAAACCG C    11

( 2 ) INFORMATION FOR SEQ ID NO:182:

( i ) SEQUENCE CHARACTERISTICS:
        (A) LENGTH: 7 base pairs
        (B) TYPE: nucleic acid
        (C) STRANDEDNESS: single
        (D) TOPOLOGY: linear (xi) SEQUENCE DESCRIPTION: SEQ ID NO:182:

GGTTTAT    7

( 2 ) INFORMATION FOR SEQ ID NO:183:

( i ) SEQUENCE CHARACTERISTICS:
( A ) LENGTH: 7 base pairs
( B ) TYPE: nucleic acid
( C ) STRANDEDNESS: single
( D ) TOPOLOGY: linear ( x i ) SEQUENCE DESCRIPTION: SEQ ID NO:183:

GGGAAAG                                                                                                7

( 2 ) INFORMATION FOR SEQ ID NO:184:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( x i ) SEQUENCE DESCRIPTION: SEQ ID NO:184:

GATCCTTTCC C                                                                                           11

( 2 ) INFORMATION FOR SEQ ID NO:185:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO:185:

CTAGAAAACC GC                                                                                          12

( 2 ) INFORMATION FOR SEQ ID NO:186:

( i ) SEQUENCE CHARACTERISTICS:
( A ) LENGTH: 6 base pairs
( B ) TYPE: nucleic acid
( C ) STRANDEDNESS: single
( D ) TOPOLOGY: linear ( x i ) SEQUENCE DESCRIPTION: SEQ ID NO:186:

GGTTTT                                                                                                 6

( 2 ) INFORMATION FOR SEQ ID NO:187:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO:187:

CAGAAGTAGC ATATATGT                                                                                    18

( 2 ) INFORMATION FOR SEQ ID NO:188:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( x i ) SEQUENCE DESCRIPTION: SEQ ID NO:188:

GCCTCCTACT ATCATTATGA ATAATCTCTT ATGTCTCCCT GGAGC                                                      45

( 2 ) INFORMATION FOR SEQ ID NO:189:

( i ) SEQUENCE CHARACTERISTICS:

( A ) LENGTH: 55 amino acids
( B ) TYPE: amino acid
( C ) STRANDEDNESS: single
( D ) TOPOLOGY: linear ( x i ) SEQUENCE DESCRIPTION: SEQ ID NO:189:

| Met | Lys | Glu | Gln | Lys | Thr | Val | Ala | Met | Arg | Val | Lys | Glu | Lys | Tyr | Gln |
|---|---|---|---|---|---|---|---|---|---|---|---|---|---|---|---|
| 1 | | | | 5 | | | | | 10 | | | | | 15 | |

| His | Leu | Trp | Arg | Trp | Gly | Trp | Arg | Trp | Gly | Thr | Met | Leu | Leu | Gly | Met |
|---|---|---|---|---|---|---|---|---|---|---|---|---|---|---|---|
| | | | 20 | | | | 25 | | | | | | 30 | | |

| Leu | Met | Ile | Cys | Ser | Ala | Thr | Glu | Lys | Leu | Trp | Val | Thr | Val | Tyr | Tyr |
|---|---|---|---|---|---|---|---|---|---|---|---|---|---|---|---|
| | | 35 | | | | | 40 | | | | | 45 | | | |

| Gly | Val | Pro | Pro | Phe | Arg | Lys |
|---|---|---|---|---|---|---|
| 50 | | | | | | 55 |

( 2 ) INFORMATION FOR SEQ ID NO:190:

( i ) SEQUENCE CHARACTERISTICS:
( A ) LENGTH: 89 amino acids
( B ) TYPE: amino acid
( C ) STRANDEDNESS: single
( D ) TOPOLOGY: linear ( x i ) SEQUENCE DESCRIPTION: SEQ ID NO:190:

| Pro | Phe | Arg | Lys | Gly | Pro | Lys | Glu | Pro | Phe | Arg | Asp | Tyr | Val | Asp | Arg |
|---|---|---|---|---|---|---|---|---|---|---|---|---|---|---|---|
| 1 | | | | 5 | | | | | 10 | | | | | 15 | |

| Phe | Tyr | Lys | Pro | Pro | Phe | Arg | Lys | Val | Gln | Ile | Asn | Cys | Thr | Arg | Pro |
|---|---|---|---|---|---|---|---|---|---|---|---|---|---|---|---|
| | | | 20 | | | | 25 | | | | | 30 | | | |

| Asn | Tyr | Asn | Lys | Arg | Lys | Arg | Ile | His | Ile | Gly | Pro | Gly | Arg | Ala | Phe |
|---|---|---|---|---|---|---|---|---|---|---|---|---|---|---|---|
| | | 35 | | | | | 40 | | | | | 45 | | | |

| Tyr | Thr | Thr | Lys | Asn | Ile | Ile | Gly | Thr | Ile | Arg | Gln | Ala | His | Cys | Asn |
|---|---|---|---|---|---|---|---|---|---|---|---|---|---|---|---|
| | 50 | | | | | 55 | | | | | 60 | | | | |

| Ile | Ser | Arg | Ala | Lys | Pro | Pro | Phe | Arg | Lys | Gln | Ile | Ile | Asn | Met | Trp |
|---|---|---|---|---|---|---|---|---|---|---|---|---|---|---|---|
| 65 | | | | | 70 | | | | | 75 | | | | | 80 |

| Gln | Glu | Val | Glu | Lys | Ala | Met | Tyr | Ala |
|---|---|---|---|---|---|---|---|---|
| | | | | 85 | | | | |

( 2 ) INFORMATION FOR SEQ ID NO:191:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:191:

AGGTCCCTTC CTGAATGGAG GTACCCCATA ATAGACTG        38

( 2 ) INFORMATION FOR SEQ ID NO:192:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( x i ) SEQUENCE DESCRIPTION: SEQ ID NO:192:

CCATTCAGGA AGGGACCTAA AGAACCTTTT AGAGATTATG TAGATAGATT TTATAAACCA        60

CCTTTTAGAA AA        72

( 2 ) INFORMATION FOR SEQ ID NO:193:

( i ) SEQUENCE CHARACTERISTICS:

( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:193:

TTTCTAAAA GGTGGTTTAT AAAATCTATC TACATAATCT CTAAAAGGTT CTTTAGGTCC        60

CTTCCTGAAT GG        72

( 2 ) INFORMATION FOR SEQ ID NO:194:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:194:

GTACAATTAA TTTGTACTTT TCTAAAAGGT GGTTTATAAA ATC        43

( 2 ) INFORMATION FOR SEQ ID NO:195:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:195:

GGTGGTTTAT AAAATCTATC TACATAATCT CTAAAAGGTT CTTTAGGTCC CATTACGATA        60

CAAACTTAAC GG        72

( 2 ) INFORMATION FOR SEQ ID NO:196:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

AAACCACCTT TTAGAAAAGT ACAAATTAAT TGTAC        35

( 2 ) INFORMATION FOR SEQ ID NO:197:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:197:

CTGCTTACGG AACGGTGGTT TTGCTCTACT AATGTTACAA TG        42

( 2 ) INFORMATION FOR SEQ ID NO:198:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:198:

CCACCGTTCC GTAAGCAGAT AATAAACATG TGGCAAGAAG TAGAAAAGC TATGTATGCT        60

TAA        63

( 2 ) INFORMATION FOR SEQ ID NO:199:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:199:

```
TTAAGCATAC ATAGCTTTTT CTACTTCTTG CCACATGTTT ATTATCTGCT TACGGAACGG      60

TGG                                                                   63
```

( 2 ) INFORMATION FOR SEQ ID NO:200:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

```
TCATCAAAGC TTCTCGAGAA AAATTAAGCA TACATAGCTT TTTC                      44
```

( 2 ) INFORMATION FOR SEQ ID NO:201:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

```
ATCATCGAGC TCGCGGCCGC CTATCAAAAG TCTTAATGAG TT                        42
```

( 2 ) INFORMATION FOR SEQ ID NO:202:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

```
GAATTCCTCG AGCTGCAGCC CGGGTTTTTA TAGCTAATTA GTCATTTTTT CGTAAGTAAG     60

TATTTTTATT TAA                                                        73
```

( 2 ) INFORMATION FOR SEQ ID NO:203:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

```
CCCGGGCTGC AGCTCGAGGA ATTCTTTTTA TTGATTAACT AGTCAAATGA GTATATATAA     60

TTGAAAAGT AA                                                          72
```

( 2 ) INFORMATION FOR SEQ ID NO:204:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:204:

GATGATGGTA CCTTCATAAA TACAAGTTTG ATTAAACTTA AGTTG    45

( 2 ) INFORMATION FOR SEQ ID NO:205:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:205:

TTAACGGATA TCGCGATAAT G    21